United States Patent
Serdarevic

(10) Patent No.: US 11,974,945 B2
(45) Date of Patent: May 7, 2024

(54) DEVICES AND METHODS FOR NOVEL RETINAL IRRADIANCE DISTRIBUTION MODIFICATION TO IMPROVE AND RESTORE VISION WITHOUT PRODUCING CORNEAL VITRIFICATION

(71) Applicant: Aperture in Motion, LLC, Phoenix, AZ (US)

(72) Inventor: Olivia N. Serdarevic, Goshen, NY (US)

(73) Assignee: Aperture in Motion, LLC, Phoenix, AZ (US)

( * ) Notice: Subject to any disclaimer, the term of this patent is extended or adjusted under 35 U.S.C. 154(b) by 770 days.

(21) Appl. No.: 17/119,617

(22) Filed: Dec. 11, 2020

(65) Prior Publication Data

US 2021/0100685 A1    Apr. 8, 2021

Related U.S. Application Data

(60) Continuation-in-part of application No. 17/071,106, filed on Oct. 15, 2020, now Pat. No. 11,766,354, (Continued)

(51) Int. Cl.
*A61F 9/007* (2006.01)
*A61F 2/16* (2006.01)
*A61F 9/008* (2006.01)

(52) U.S. Cl.
CPC ............ *A61F 9/007* (2013.01); *A61F 2/1627* (2013.01); *A61F 2/1637* (2013.01);
(Continued)

(58) Field of Classification Search
CPC ...... A61F 9/007; A61F 2/1613; A61F 2/1627; A61F 2/1635; A61F 2/1637; A61F 2/1648; A61F 2/1654; A61F 2009/00863
See application file for complete search history.

(56) References Cited

U.S. PATENT DOCUMENTS 6,155,682 A * 12/2000 Steinberg ................. G02C 7/14
                                                        623/6.35
6,387,088 B1    5/2002 Shattuck et al.
(Continued)

FOREIGN PATENT DOCUMENTS

WO        2017046358 A1    3/2017

OTHER PUBLICATIONS

Alio et al., "Phakic Intraocular Lens Implantation for Treatment of Anisometripia and Amblyopia in Children; 5-year Follow Up," Slack Incorporated, Feb. 1, 2011 (9 pages).
(Continued)

*Primary Examiner* — William H Matthews
(74) *Attorney, Agent, or Firm* — Duane Morris LLP

(57) ABSTRACT

Methods and apparatus to improve or restore vision by causing a rebooting of the visual system of an eye with modification of visual search, sampling and stimulation away from the preferred retinal locus of fixation of an eye to enhance neural integration and perception of visual information from within the field of view are described herein. Some embodiments cause transient, reversible or repeatable redirection of environmental light away from the preferred retinal locus of fixation of an eye to multiple retinal locations that are not the preferred retinal locus of fixation. Some embodiments reduce exposure of environmental light at the preferred retinal locus of fixation of an eye for a determinable interval at a determinable rate. Some embodiments cause a defocusing of environmental light at the preferred retinal locus of fixation in an eye with a visual impairment or loss.

7 Claims, 24 Drawing Sheets

Related U.S. Application Data which is a continuation of application No. 16/593,269, filed on Oct. 4, 2019, now Pat. No. 10,835,417, which is a division of application No. 15/693,208, filed on Aug. 31, 2017, now abandoned.

(52) U.S. Cl.
CPC .......... *A61F 2/1648* (2013.01); *A61F 2/1654* (2013.01); *A61F 9/0079* (2013.01); *A61F 9/008* (2013.01); *A61F 2009/00842* (2013.01); *A61F 2009/00853* (2013.01); *A61F 2009/00863* (2013.01); *A61F 2009/00872* (2013.01)

(56) References Cited

U.S. PATENT DOCUMENTS

| | | | |
|---|---|---|---|
| 9,526,656 | B2 | 12/2016 | Serdarevic et al. |
| 9,532,904 | B2 | 1/2017 | Serdarevic et al. |
| 9,545,339 | B2 | 1/2017 | Serdarevic et al. |
| 10,835,417 | B2 | 11/2020 | Serdarevic |
| 2002/0038134 | A1 | 3/2002 | Greenberg et al. |
| 2011/0306919 | A1 | 12/2011 | Latina et al. |
| 2015/0133901 | A1 | 5/2015 | Serdarevic et al. |
| 2015/0297342 | A1 | 10/2015 | Rosen et al. |
| 2017/0007395 | A1 | 1/2017 | Peyman |
| 2019/0046357 | A1 | 2/2019 | Knox et al. |
| 2019/0271849 | A1 | 9/2019 | Serdarevic et al. |
| 2020/0030082 | A1 | 1/2020 | Serdarevic |
| 2020/0197223 | A1 | 6/2020 | Yu et al. |

OTHER PUBLICATIONS

International Search Report and Written Opinion dated Jan. 7, 2019, in PCT/US2018/048910 (10 pages).
International Search Report and Written Opinion dated Apr. 13, 2021, in PCT/US2020/064620 (12 pages).
Alio et al., "Phakic Intraocular lens Implantation for Treatment of Anisometripia and Amblyopia in Chidren; 5-year Follow Up," Slack Incorporated, Feb. 1, 2011 (9 pages).
International Search report dated Jan. 7, 2019, in PCT/US1848910 (10 pages).

\* cited by examiner

DEVICES AND METHODS FOR NOVEL RETINAL IRRADIANCE DISTRIBUTION MODIFICATION TO IMPROVE AND RESTORE VISION WITHOUT PRODUCING CORNEAL VITRIFICATION

CROSS-REFERENCE TO RELATED APPLICATION

This application is a continuation-in-part of U.S. application Ser. No. 17/071,106, filed Oct. 15, 2020 (now U.S. Pat. No. 11,766,354), which is a continuation of, and claims the benefit of priority to, U.S. application Ser. No. 16/593,269, filed Oct. 4, 2019 (now U.S. Pat. No. 10,835,417), which is a divisional of, and claims the benefit of priority to, abandoned U.S. application Ser. No. 15/693,208, filed Aug. 31, 2017. The disclosures of each of these applications are incorporated herein by reference in their entireties.

TECHNICAL FIELD

The disclosed exemplary embodiments relate to devices and methods for novel retinal irradiance distribution modification (IDM) to improve, stabilize or restore vision. The disclosed exemplary embodiments also relate to devices and methods to reduce vision loss from diseases, injuries and disorders that involve damaged and/or dysfunctional and/or sensorily deprived retinal cells. The applications of the exemplary retinal IDM devices and methods described herein include, but are not limited to, treatment of macular degeneration, diabetic retinopathy and glaucoma. The therapy provided by one or more of the exemplary retinal IDM devices and methods described herein can also be used in combination with other therapies including, but not limited to, pharmacological, retinal laser, gene and stem cell therapies.

BACKGROUND

Conventional devices and methods offer suboptimal solutions for improving vision and/or restoring vision to reduce vision loss from diseases, injuries and disorders that involve damaged and/or dysfunctional and/or sensorily deprived retinal cells. Vision loss is caused by diseases, injuries and disorders including, but not limited to, age-related macular degeneration (AMD), Stargardt disease, Best vitelliform macular dystrophy, light-induced retinal injuries, cone dystrophies, reverse retinitis pigmentosa, myopic macular degeneration, macular scars, diabetic retinopathy (DR), macular edema, macular hole, macular detachment, macular pucker, vascular retinal disorders (including but not limited to retinal vein occlusions and Coats' Disease), retinitis pigmentosa, glaucoma or other neuroretinal or ganglion cell disorders and amblyopia (caused by refractive error, medial opacity or obstruction, or an oculomotor condition, or any combination thereof). AMD, DR and other retinal diseases and disorders are major causes of worldwide vision impairment, including blindness. There are great unmet needs for solutions that provide meaningful vision and vision-related quality of life improvements to patients who suffer from vision loss caused by retinal problems. Conventional devices and methods only offer suboptimal amelioration of, or compensation for, some symptoms of vision loss from such diseases, injuries and disorders.

Conventional devices and methods for amelioration of, or compensation for, symptoms of vision loss, such as telescopes (handheld, in electronic devices, in spectacles, in contact lenses, in intraocular lenses, or in the cornea) or annular multifocal corneal laser treatments, only magnify images within a small area of view. Devices and methods for amelioration of, or compensation for, symptoms of vision loss using prisms or prismatic effects (in spectacles, in contact lenses, or in intraocular lenses) only deviate images from objects within the visual field angularly onto a small area of the retina. The handheld and electronic telescopes require patients to remain stationary and these telescopes magnify a very small area of the patient's visual field. Telescopes in spectacles, contact lenses and intraocular devices require visual training over periods of weeks to months, produce tunnel vision, prevent binocular vision, and result in poor ambulatory vision. Telescopes or prisms in intraocular devices involve surgery with risks of severe intraoperative and postoperative complications and adverse events. Oculomotor training for eccentric fixation requires training over a period of weeks to months with diminishing effects over time and abnormal head positioning, with minimal improvements in reading speed and with minimal or no improvements in visual acuity. Prisms in glasses, contact lenses or intraocular lenses are poorly tolerated and can cause double vision. All optical devices on glasses or contact lenses fail to maintain a constant moment-to-moment visual correction as the eyes move, preventing the full effects of neural adaptation to develop. Retinal prostheses, such as eyeglass-mounted cameras that transmit wirelessly to a microelectrode array implanted intraocularly within or on a patient's retina cannot provide high resolution vision and provide only vague motion detection and shape discernment. Intraocular implants with telescopes, prisms, or microelectrode arrays involve surgery with risks of severe intraoperative and postoperative complications and adverse events, including death, loss of the eye, and complete loss of sight.

Conventional vision aids provide amelioration of, or compensation for, symptoms of visual loss but do not provide restorative benefits including, but not limited to, repair of damaged retinal cells or improvement of functioning of retinal cells.

Conventional drug therapies including, but not limited to, anti-vascular endothelial growth factor (anti-VEGF) agents for neovascular AMD, diabetic macular edema, and other neovascular retinal disorders and the prostaglandin analogs for glaucoma prevent further progression of vision loss but do not provide significant vision restoration for most patients. Conventional device therapies including, but not limited to, retinal laser photocoagulation, photodynamic laser therapy, radiation therapy, photobiomodulation, subthreshold micropulse laser therapy, glaucoma laser therapy and glaucoma surgery with or without shunt implantation do not improve vision significantly. Patients who suffer from dry AMD, marked by retinal dysfunction with drusen formation and eventual retinal atrophy, have no effective treatment options other than lifestyle modification, the use of glasses to block ultraviolet or blue light over the entire visual field, and the use of vitamins and other supplements.

SUMMARY

In some examples, IDM devices and methods may optically modify permanently, temporarily or with variable modifications over time in at least three retinal regions, including a retinal fixation region, spatial, temporal, spatiotemporal, chromatic, achromatic and contrast information distributions of environmental light from an ocular field of view by means of simultaneous light redirections from a retinal fixation region to at least two other spatially separated retinal regions (hereinafter: "IDM devices and methods"). The devices and methods described herein produce novel retinal irradiance distribution modifications (IDMs) to improve vision. One or more of the exemplary IDM devices and methods described herein also provide vision improvements, vision stabilization and/or vision restoration benefits to patients who have visual symptoms from, or have suffered visual loss from, diseases, injuries and disorders including, but not limited to, eyes with damaged and/or dysfunctional and/or sensorily deprived retinal cells. One or more of the exemplary IDM devices and methods described herein also include, but are not limited to, retinal IDM devices and methods for vision improvement and/or vision restoration to overcome vision loss caused by diseases, injuries and disorders including, but not limited to, age-related macular degeneration (AMD), Stargardt disease, Best's vitelliform macular dystrophy, light-induced retinal injuries, cone dystrophies, reverse retinitis pigmentosa, myopic macular degeneration, macular scars, diabetic retinopathy (DR), macular edema, macular hole, macular detachment, macular pucker, vascular retinal disorders (including but not limited to retinal vein occlusions and Coats' Disease), retinitis pigmentosa, nutritional retinal disorders, glaucoma or other neuroretinal or ganglion cell disorders and amblyopia (caused by refractive error, medial opacity or obstruction, or an oculomotor condition, or any combination thereof). In contrast to conventional devices and methods, the IDM devices and methods described herein also provide, without requiring oculomotor or perceptual training, better vision and/or quality of life outcomes, fewer and less severe complications or adverse effects, and greater patient convenience and comfort to patients treated with retinal IDM.

Exemplary embodiments of retinal IDM devices described herein include, but are not limited to, retinal IDM lasers and other light emitting sources to produce photoablation, photodisruption, photoionization, photochemical and/or photothermal keratoplasty, but not producing corneal vitrification; retinal IDM corneal crosslinking devices; retinal IDM radiofrequency transmitting devices; retinal IDM contact lenses; retinal IDM spectacles; retinal IDM corneal inlays; and retinal IDM intraocular lenses, all of which are configured to produce retinal IDM for vision improvement, with or without vision restorative benefits including, but not limited to, retinal cell repair and/or retinal regeneration.

In some examples, retinal IDM devices and methods are combined with non-retinal IDM therapies including, but not limited to, pharmacological agents, including but not limited to, vascular endothelial growth factor antagonists, retinal laser, ionizing radiation, photobiomodulation, stem cell, genetic, epigenetic and optogenetic therapies.

While the description herein shows, describes, and points out novel features as applied to various embodiments, it will be understood that various omissions, substitutions, and changes in the form and details of the device or method illustrated can be made without departing from the spirit of the disclosure. As will be recognized, certain of the exemplary embodiments described herein can be embodied within a form that does not provide all of the features and benefits set forth herein, as some features can be used or practiced separately from others. All changes which come within the meaning and range of equivalency of the claims are to be embraced within their scope.

DETAILED DESCRIPTION

Figure 1:
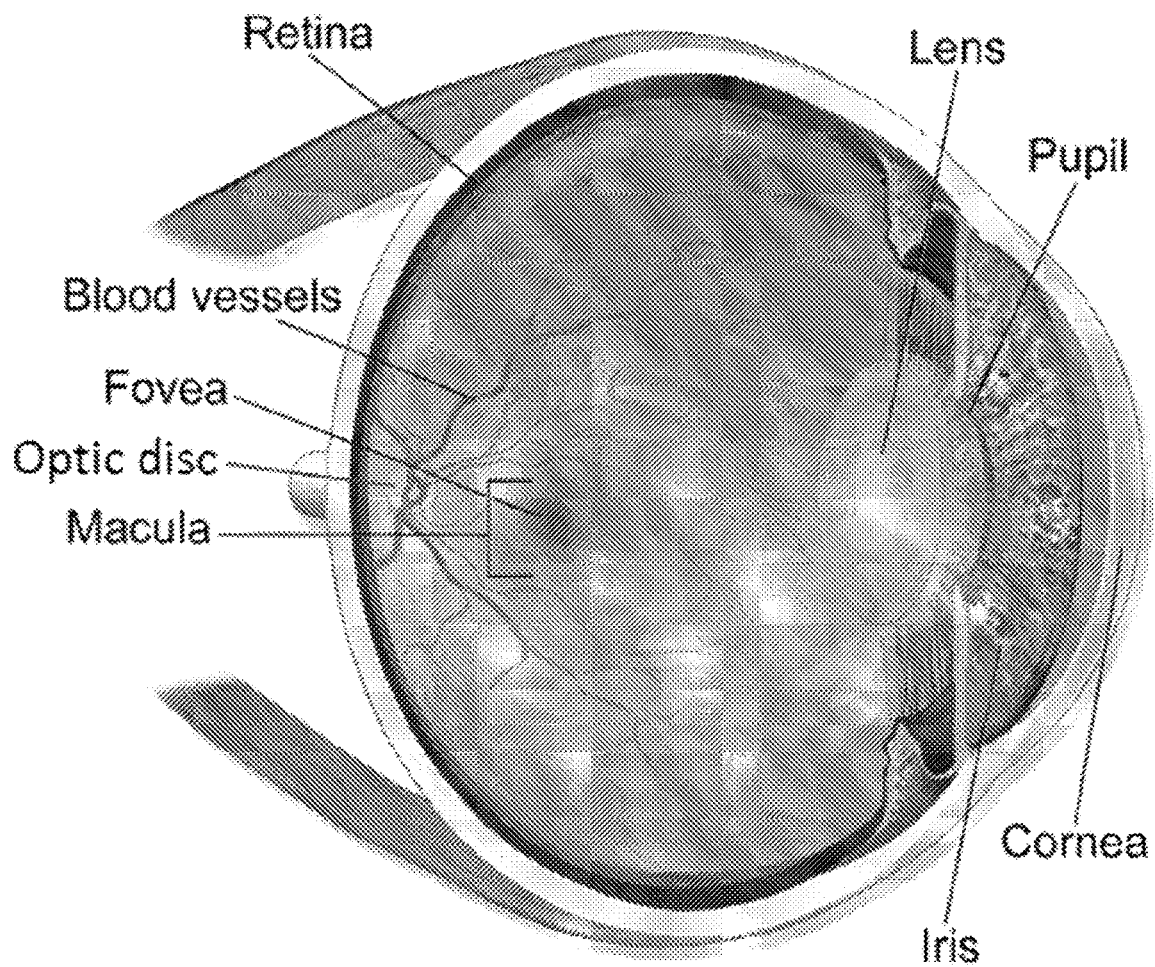
FIG. 1 is a cutaway drawing of an eye showing principal ocular structures.

The exemplary retinal irradiance distribution modification (IDM) devices and methods described herein includes retinal IDM devices and methods that optically modify permanently, temporarily or with variable modifications over time in at least three retinal regions, including a retinal fixation region, spatial, temporal, spatiotemporal, chromatic, achromatic and contrast information distributions of environmental light from an ocular field of view by means of simultaneous light redirections from a retinal fixation region to at least two other spatially separated retinal regions. Retinal IDM devices and methods have applications for vision improvement or stabilization and/or vision restoration and/or amelioration of and/or compensation for visual symptoms from ophthalmic conditions, diseases, injuries and disorders, including, but not limited to, in eyes with visual loss due to diseases, injuries and disorders that involve damaged and/or dysfunctional and/or sensorily deprived retinal cells. The IDM devices and methods reduce visual loss caused by diseases, injuries and disorders including, but not limited to, age-related macular degeneration (AMD), Stargardt disease, Best vitelliform macular dystrophy, light-induced retinal injuries, cone dystrophies, reverse retinitis pigmentosa, myopic macular degeneration, macular scars, diabetic retinopathy (DR), macular edema, macular hole, macular detachment, macular pucker, vascular retinal disorders (including but not limited to retinal vein occlusions and Coats' Disease), retinitis pigmentosa, nutritional retinal disorders, glaucoma or other neuroretinal or ganglion cell disorders and amblyopia (caused by refractive error, medial opacity or obstruction, or an oculomotor condition, or any combination thereof).

Vision processing involves the interaction of the two eyes and the brain through a network of neurons, receptors, and other specialized cells. The first steps in this sensory process include the stimulation of light receptors in the retina, conversion of the light stimuli into neural signals, processing of these neural signals through many kinds of retinal interneurons, and transmission of electrical signals containing spatial, temporal, spatiotemporal and chromatic visual information from each eye to the brain. Processing by retinal interneurons involves chemical and electrical messages sent among retinal cell types including the feedforward pathway from photoreceptors to bipolar cells and on to ganglion cells, along with interactions of these cell types with and among horizontal and amacrine cells. This information is further processed in the brain. Functional vision results when the brain integrates retinal information across space, time, and saccades.

Retinal irradiance is the amount of light power per unit area that is incident on the retina. Irradiance is measured in units of $W/m^2$ where W is the light power in watts and m is a meter of length. An eye with a retinal disorder can have decreased retinal sensitivities of varying magnitudes to light irradiance in retinal regions. Decreased retinal sensitivities can be demonstrated by diagnostic testing, including, but not limited to, microperimetry. There is incorrect and/or impartial visual processing of light rays within the environmental field of view of a retinal region with decreased retinal sensitivities. Following retinal IDM treatment by one or more of the exemplary retinal IDM devices and methods described herein, the distribution of visual information in the environmental field of view of an eye is modified by multiple and spatially separated redirections of the light rays onto multiple retinal regions, including regions with better retinal sensitivities. Retinal IDM, therefore, is distinct from a modification of the total irradiance onto the entire retina and may or may not include a modification of the total irradiance onto the entire retina. Retinal spectral irradiance is the amount of light power per unit area per unit wavelength that is incident on the retina. Detection of light by the retina is different for different wavelengths of light and for photopic, mesopic and scotopic illumination conditions. IDM devices and methods are useful in all illumination conditions including, but not limited to, day vision and night vision illumination conditions. Unless otherwise noted in this application, retinal irradiance is always considered for visible light with a spectral distribution including, but not limited to, sunlight or light with a color rendering index (CRI) similar to sunlight (i.e., CRI>80, with a maximum of 100—a perfect match of the spectral distribution to sunlight) and for photopic illumination conditions including, but not limited to, daylight.

It is understood that retinal irradiance and retinal irradiance distribution can be measured for both model and ex vivo eyes by using photometric instrumentation known to one skilled in the art including, but not limited to, photodiode arrays, charge-coupled device (CCD) sensors and complementary metal oxide semiconductor (CMOS) sensors. It is also understood to one skilled in the art that retinal irradiance and retinal irradiance distribution can be predicted using raytracing computations with model eyes.

The retinal irradiance distribution, together with its spatiotemporal, chromatic, achromatic and contrast information, can be specified on various spatial and temporal scales. Spatial scales include, but are not limited to: A) receptive fields of domains of retinal cells including, but not limited to, spatial scales as small as an individual photoreceptor and including both the center and surround of each cell's receptive field; B) the entire fovea; C) the entire macula; D) the entire central visual field that extends to an eccentricity of ca. 20°; and E) the entire visual field. Locations on the retina with respect to the center of the foveola can be specified in terms of polar coordinates r,θ or r',θ in which r is the distance in mm units or r' is the distance in terms of retinal eccentricity in units of degrees, and θ is the angular coordinate.

Temporal scales include, but are not limited to: A) a moment-to-moment timescale that can be as short as 10 milliseconds, during which irradiance and contrast can be modified from: i) changes in the radiance of objects in visual space, ii) from movements of the eye, including both fixational movements and saccades that cause light (from different objects in the visual space) to irradiate a spatial region of the retina, or iii) any combination of i and ii; B) an intermediate timescale, that extends to several minutes duration, during which processes of retinal adaptation occur; C) a long timescale, that is in the range of days to years duration, during which the overall irradiance on a spatial region of the retina can affect the health of retinal cells; and D) a second long timescale that be in the range of days to years duration, during which processes of neural adaptation occur.

Contrast refers to changes in irradiance across the spatial and temporal scales described above. Contrast can also refer to changes in irradiance on temporal scales that match the dynamics of the light responses in retinal cells. Contrast can also refer to changes in irradiance on spatio-temporal scales that match the dynamics of motion-sensitive cells in the retina. Contrast can also refer to changes in spectral irradiance that match the chromatic sensitivities of retinal cells.

Figure 2:
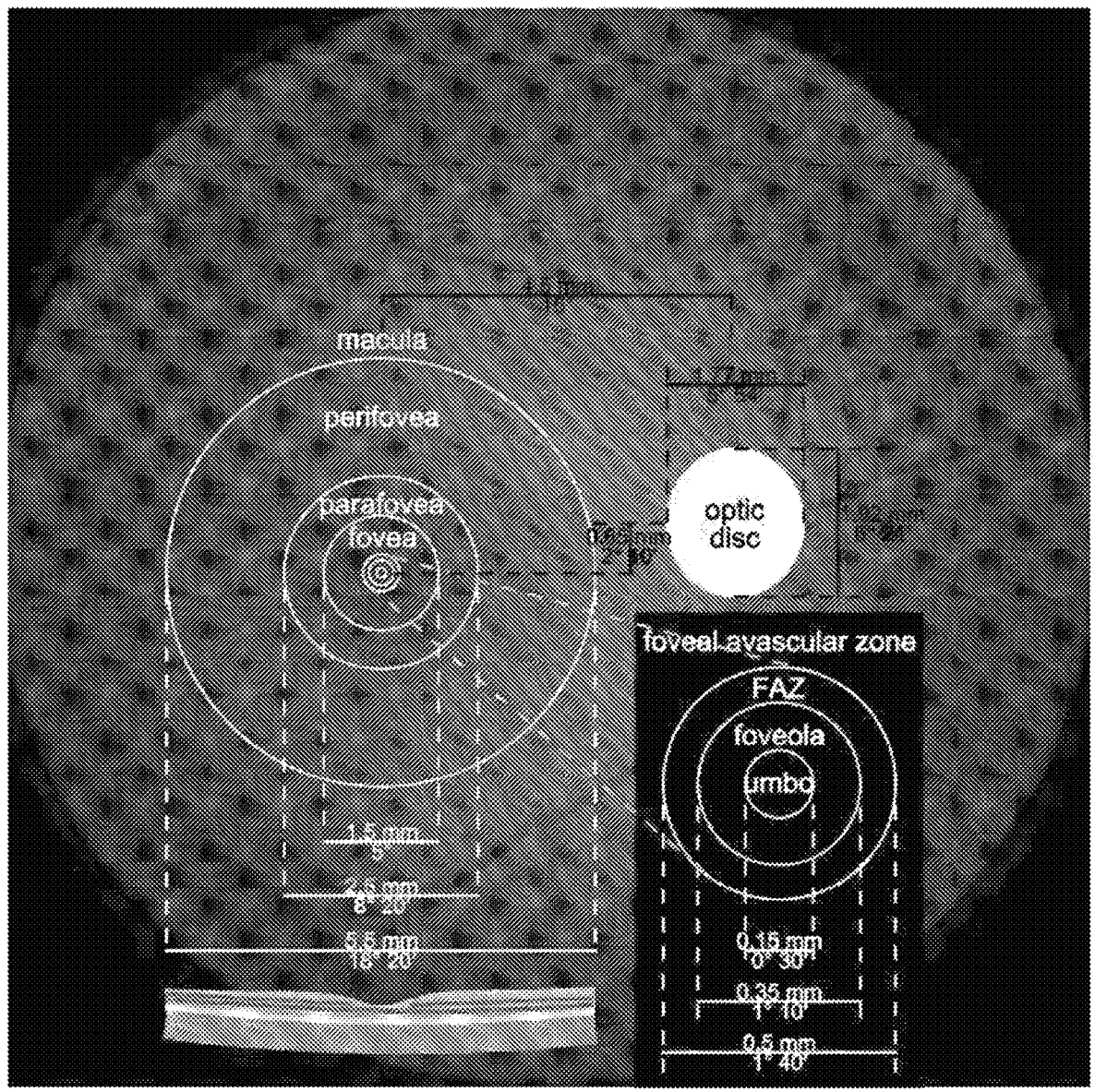
FIG. 2 is a drawing of an eye in the vicinity of the macula showing retinal structures and dimensions.
Figure 3:
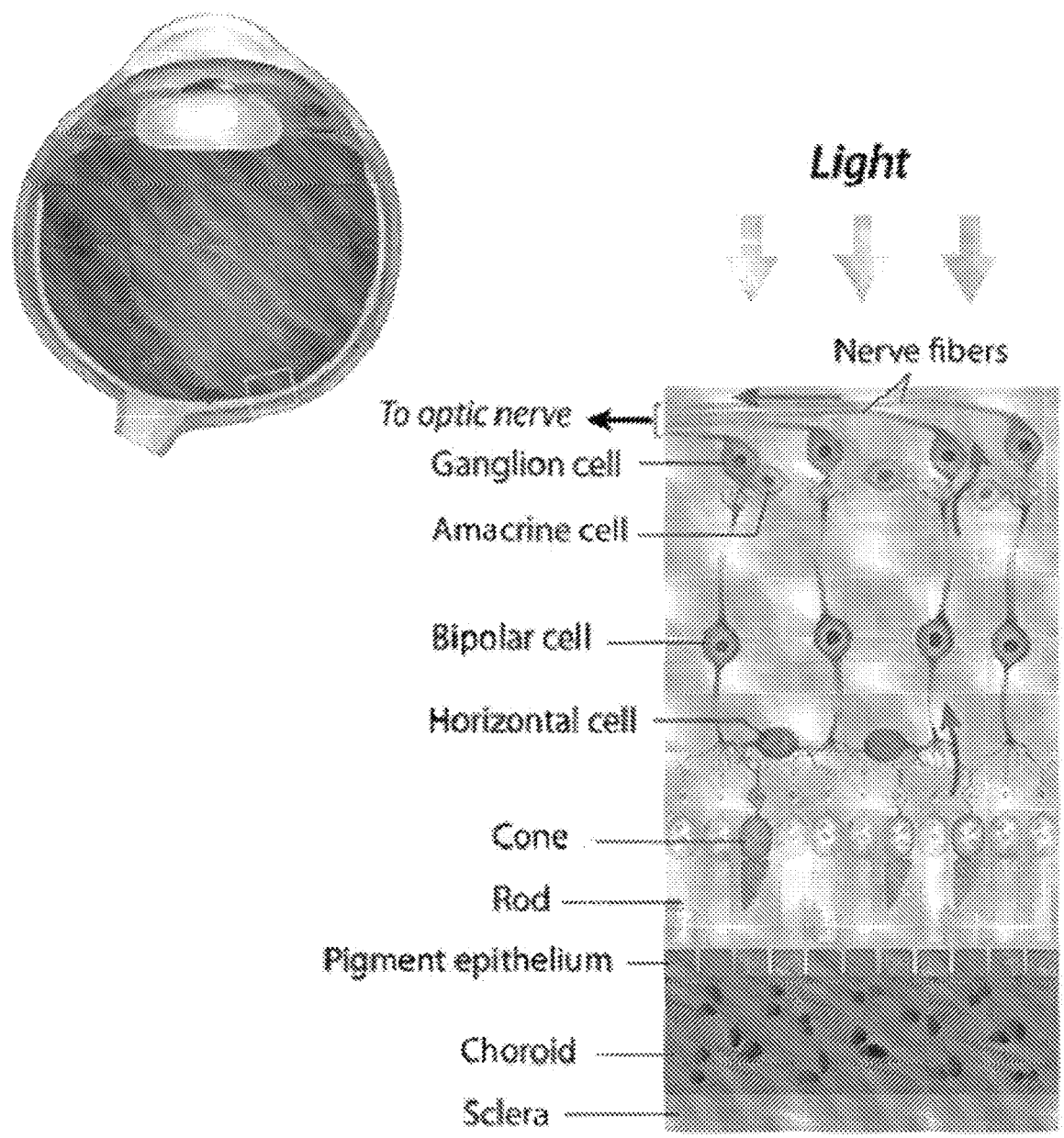
FIG. 3 is a schematic retinal microstructure and vision transduction drawing.

The retina of the eye is illustrated on the cutaway drawing of an eye shown in FIG. 1. Principal ocular structures are the cornea, the iris (defining the pupil aperture), the lens and the retina including the fovea, macula, optic disc and blood vessels. The region of the retina in the vicinity of the macula is shown in FIG. 2, with identification of the fovea and other retinal areas together with their dimensions. A retinal schematic microstructure and vision transduction drawing is shown in FIG. 3, in which light produced by IDM devices and methods irradiates the retinal, producing electrical signals from photoreceptor (cone and rod) cells; these electrical signals are pre-processed by specialized retinal (horizontal, bipolar, amacrine and ganglion) cells leading to action potentials (electrical "spikes") that propagate through the optic nerve (and ultimately to the visual cortex) through axons (nerve fibers) emanating from retinal ganglion cells. The choroid contains capillary blood vessels that provide nutrients to retinal cells and that transport waste products from the retina.

Figure 4:
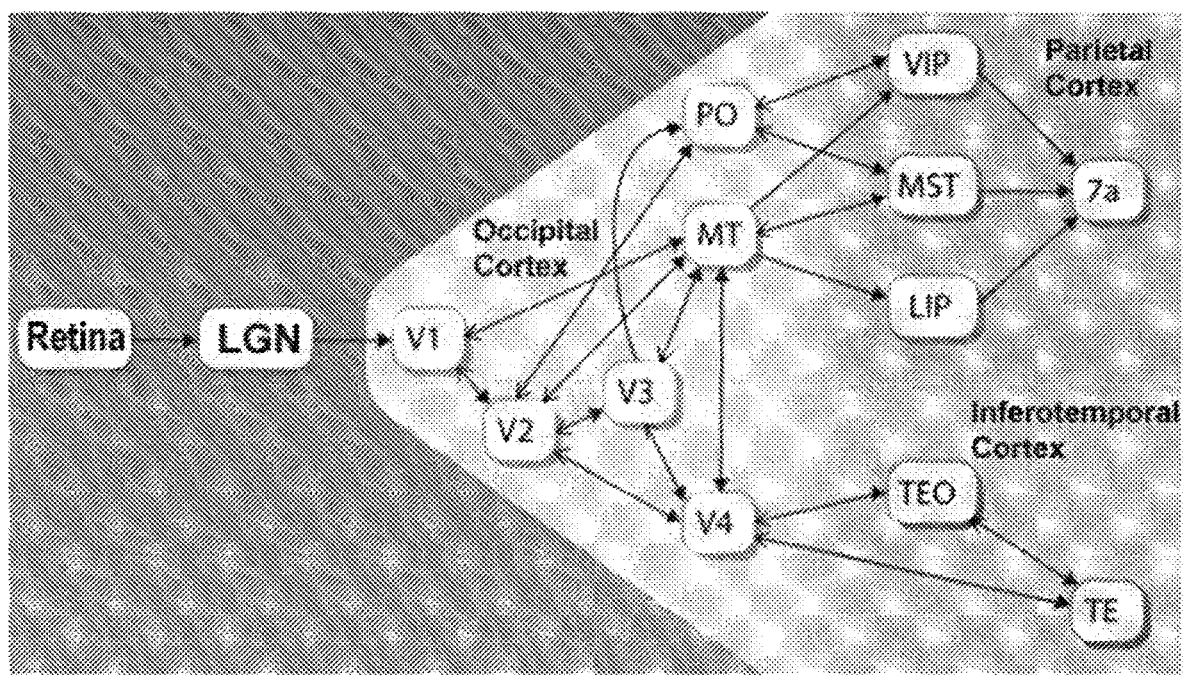
FIG. 4 is a schematic simplified visual pathways drawing.

FIG. 4 shows schematic simplified pathways for the cortical processing of visual information. Retinal ganglion cell axons connect to the lateral geniculate nucleus (LGN) as well as to other subcortical structures including, but not limited to, the superior colliculus that are not shown. LGN relay cells connect to the primary visual cortex (area V1). The primary visual cortex in turn connects to multiple cortical visual areas (including, but not limited to, the ventral stream and the dorsal stream) that process information to provide visual outcomes including, but not limited to, spatial vision, motion perception, depth perception, form perception and color vision. The visual cortex interacts with the thalamus via recurrent loops to produce integrated visual perception. Visual cortical areas also interact with subcortical structures including, but not limited to, the basal ganglia, thalamus, cerebellum, superior colliculus and brainstem to control eye movements. Subcortical visual processing includes, but is not limited to, eye and head movements, pupil sizes and circadian rhythm. It is understood that vision improvement including, but not limited to, neuroadaptation involves the complex interaction of neural processing between and among all the stages of the visual pathway.

Figure 5:
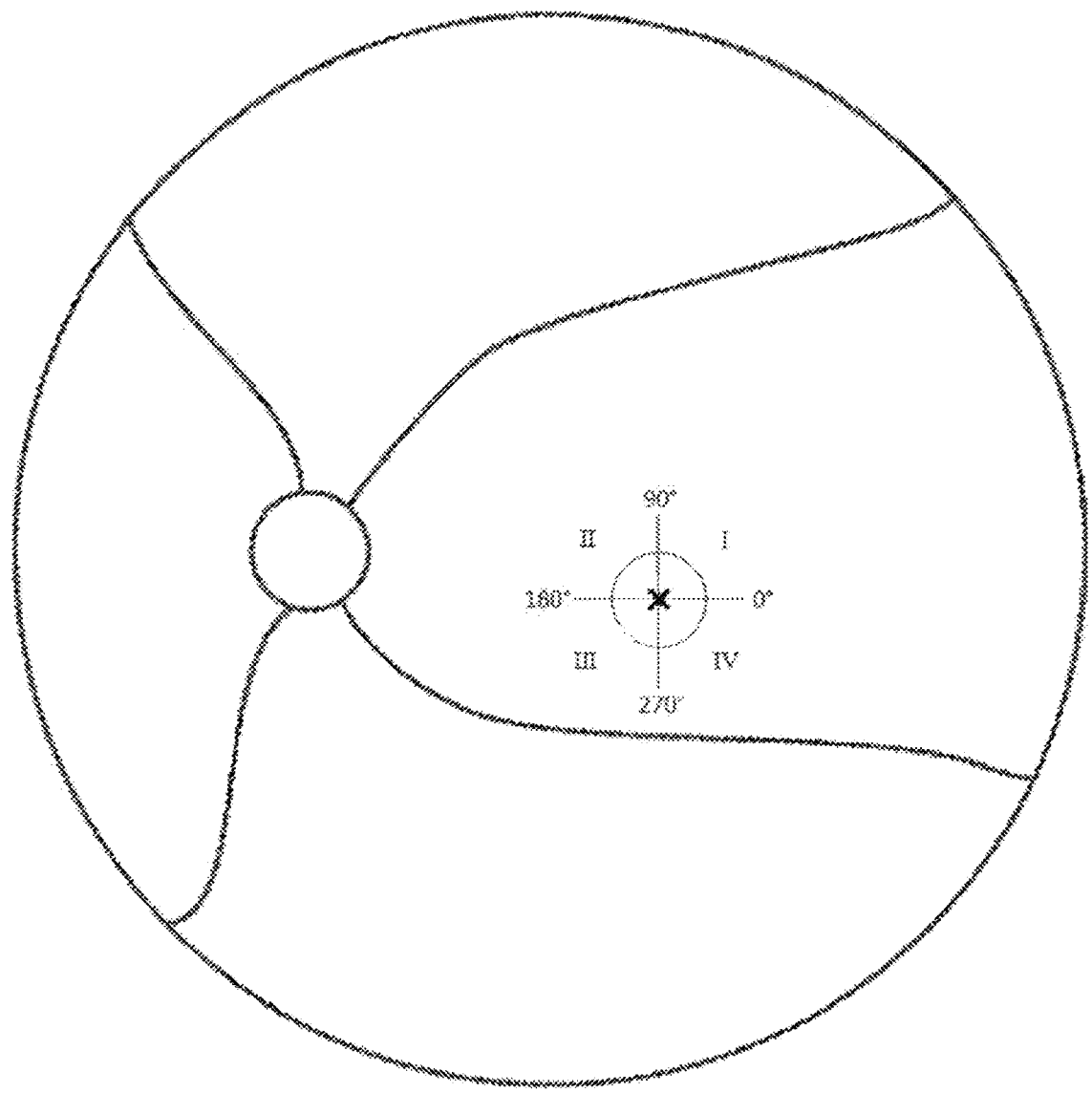
FIG. 5 is a schematic retina drawing showing the fovea (right circle), optic disc (left circle) and retinal vessels (wavy lines extending to the optic disc).

A schematic retina drawing is shown in FIG. 5. The fovea is shown as the circle at the right in FIG. 5 with 0°-180° (temporal-nasal) and 90°-270° (superior-inferior) meridians dividing the retinal area into four quadrants: I (superior-temporal), II (superior-nasal), III (inferior-nasal) and IV (inferior-temporal). Foveal polar coordinates r,θ specify locations on the retina referenced to the foveolar center "X". The fovea is approximately 0.75 mm (2.5° eccentricity) in radius; it contains the highest density of photoreceptors (cones) for the highest spatial resolution of vision. The optic disc is shown as the circle at the left in FIG. 3 with retinal blood vessels represented as wavy lines.

Figure 6:
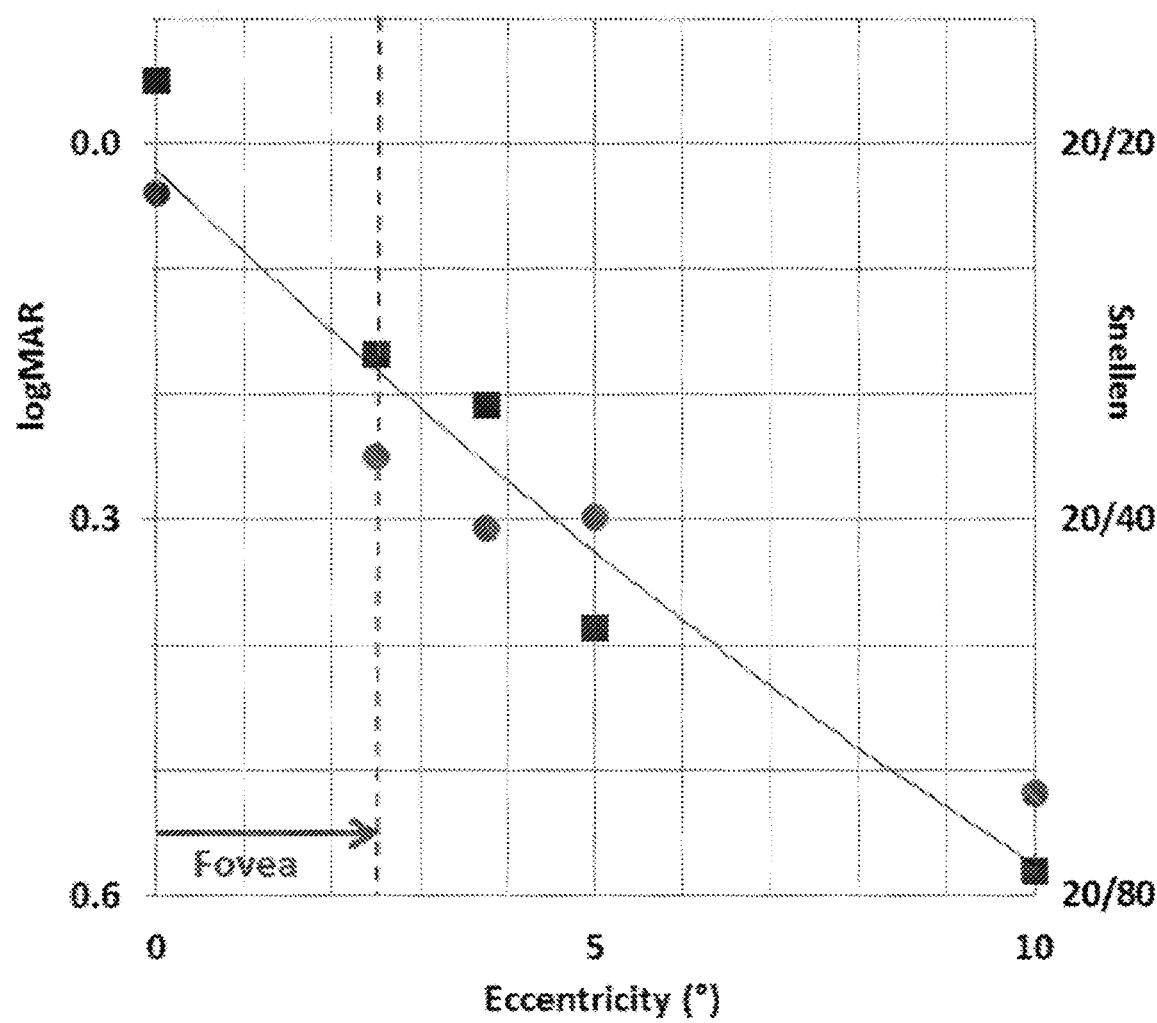
FIG. 6 is a graph of visual acuity vs. retinal eccentricity using the foveolar center as the zero-eccentricity reference.

FIG. 6 shows the variation of visual acuity (both in log MAR and Snellen units) as a function of retinal eccentricity. FIG. 6 is redrawn from Figure 3 of Williams D R and Coletta N J, Cone spacing and the visual resolution limit, J Am Opt Soc A (1987). Measurements are for two subjects (circle and square symbols); a mean value of 0.907 log MAR (20/162 Snellen) was also measured at 20° retinal eccentricity. A quadratic fit to the measurements is shown. Conversion from retinal eccentricity: 1° retinal eccentricity=approximately 0.3 mm. The fovea extends to ca. 2.5° retinal eccentricity. The greatest visual acuity is obtained for light focused onto the foveal center of a fully functional retina. Both defocus and lack of full retinal functionality can reduce visual acuity. Conventional vision aids including, but not limited to, spectacles and contact lenses can improve focus but cannot improve retinal functionality. Although useful vision can be based on using large regions of the retina outside the fovea (i.e., outside approximately 2.5° retinal eccentricity)—see FIG. 6—these regions outside the fovea may be underutilized if higher spatial resolution visual information from the fovea is weighted preferentially in the visual cortex.

The exemplary retinal irradiance distribution modification (IDM) devices and methods described herein includes retinal IDM devices and methods that optically modify permanently, temporarily or with variable modifications over time in at least three retinal regions, including the fovea or another retinal fixation region, spatial, temporal, spatiotemporal, chromatic, achromatic and contrast information distributions of environmental light from an ocular field of view by means of light redirections from the fovea or another retinal fixation region to at least two other spatially separated retinal regions. The retinal regions are defined by ranges of polar coordinates, wherein the spatially separated retinal regions are non-overlapping regions, partly overlapping regions or any combination of non-overlapping and partly overlapping regions and wherein the amount(s) and location(s) of retinal IDM are for predetermined spatial distribution(s) with or without predetermined temporal distributions. The retinal irradiance distribution modifications contain information including, but not limited to, spatial, temporal, spatiotemporal, chromatic, achromatic and contrast information or any combination thereof.

The exemplary retinal IDM devices and methods described herein have applications for both vision improvement and vision restoration in diseased eyes as described herein: A—for vision and quality of life improvement and B—for vision restoration benefits including, but not limited to, retinal cell repair and/or retinal regeneration. It is understood that, in some embodiments, vision improvement can be obtained by retinal IDM treatment using the retinal IDM devices and methods described herein without vision restoration benefits, in that some regions of the retina may remain partly or completely dysfunctional or may even become less functional as time elapses after retinal IDM treatment. It is also understood that, in some other embodiments, both vision improvement and beneficial vision restoration effects, including increased functionality of some regions of the retina that were partly or completely dysfunctional prior to retinal IDM treatment, can be obtained due to retinal IDM treatment.

In some exemplary embodiments described herein that are intended for vision improvement, retinal IDM devices and methods are configured to optically redirect light from one or more partly or completely dysfunctional retinal areas and to redirect that light, in whole or in part, onto two or more retinal areas, including one or more functional retinal areas, wherein the dysfunctional retinal areas include, but are not limited to, at least one of an area of dysfunctional foveal photoreceptors, multiple areas of dysfunctional foveal photoreceptors, a dysfunctional preferred retinal locus (PRL), multiple dysfunctional PRLs, multiple spatially separated dysfunctional retinal areas of photoreceptors or any combination thereof, wherein the functional retinal areas include, but are not limited to, at least one of a retinal area of functional photoreceptors, multiple retinal areas of functional photoreceptors, and multiple spatially, separated functional retinal areas of photoreceptors wherein all the functional retinal areas of photoreceptors have functional signaling to functional ganglion cells.

In some exemplary embodiments described herein, the functional retinal areas include, but are not limited to, a. at least two spatially separated areas in at least two different quadrants (see FIG. 5) and b. at least one spatially separated area in each of the four retinal quadrants (see FIG. 5).

The retinal areas are defined by ranges of polar coordinates, wherein the spatially separated retinal areas are non-overlapping areas, partly overlapping areas or any combination of non-overlapping and partly overlapping areas, wherein the amount(s) and location(s) of retinal IDM are for predetermined spatial distribution(s) with or without predetermined temporal distribution(s), and wherein the retinal irradiance distribution modifications contain information including, but not limited to, spatial, temporal, spatiotemporal, chromatic, achromatic and contrast information or any combination thereof.

In some exemplary embodiments described herein, the spatially separated retinal areas include multiple areas in each of the four retinal quadrants in order to increase the likelihood of redirecting light: a. onto a functional area or areas in eyes with many dysfunctional areas, b. onto multiple functional areas to be used for different visual tasks, and c. onto multiple functional areas that can be used if or as the retinal disease progresses.

In some embodiments of the exemplary retinal IDM devices and methods described herein, the retinal IDM alters the moment-to-moment patterns of light irradiance coming from edges and objects to increase the relative irradiance difference on nearby photoreceptors (i.e., increases the contrast).

In some embodiments of the exemplary retinal IDM devices and methods described herein, the pattern of retinal irradiance distribution modification (IDM): (i) improves neural computation with integration of additional and/or more correctly coded retinal information from macular and peripheral retinal cells—including, but not limited to, photoreceptors, bipolar cells, amacrine cells, horizontal cells, Müller glial cells, ganglion cells or any combination of retinal cells—to enable processing of more complete stimulus patterns and/or (ii) improves functioning of retinal circuitry, including connectivity functions in visual processing involving photoreceptors, ganglion cells, amacrine cells, bipolar cells, horizontal cells, and Müller cells or any combination thereof and/or (iii) triggers processes of neural adaptation, including but not limited to, use of alternate, latent, and/or new visual pathways in the retinal and brain including, but not limited to: a. rerouting of visual information encoded by peripheral areas of the retina to neurons at high levels of the visual cortex with receptive fields normally tasked with encoding objects at the center-of-gaze, permitting beneficial alteration of crowding properties with reduced critical spacing in those peripheral areas and/or b. changing the destination of saccadic eye movements (herein, referred to as a "fixation") to new retinal loci and/or c. beneficially changing the amplitude and/or speed of eye movements within a fixation and/or d. beneficially changing the interaction of the saccadic corollary discharge circuit with the rest of the visual cortex and/or e. producing more effective and spontaneous searching to achieve more effective integration of a greater amount of more correct visual information by searching mechanisms including, but not limited to, spontaneously producing motor learning in the eye movement strategy to both collect information from a greater area of the visual scene and use more functional retinal cells for improved visual information.

In some embodiments of the exemplary retinal IDM devices and methods described herein, retinal IDM re-routes central visual information (typically, but not limited to, information at the center-of-gaze) through alternative retinal pathways, thereby restoring the transmission of high-resolution spatial information from these areas of visual space to the rest of the brain—including but not limited to the cerebral cortex, basal ganglia, thalamus, superior colliculus, and other brainstem nuclei—thereby enhancing global visual processing mechanisms, including, but not limited to: a. enhancing global pooling of contour information and/or b. improving shape discrimination and/or c. improving motion processing and/or d. improving color processing and/or e. improving visually guided behavior or any combination thereof.

In some embodiments of the exemplary retinal IDM devices and methods described herein, retinal IDM triggers processes of neural adaptation in central brain circuits (including, but not limited to, the visual cortex and/or the visual thalamus and/or superior colliculus or any combination thereof), including but not limited to structural and synaptic plasticity that include, but are not limited to:
a. restoring visual perception to areas of visual space corresponding to damaged areas of the retina, which had, prior to treatment, produced little or no visual perception (i.e., were scotomata) by inducing neurons in central brain circuits to develop spatial receptive fields covering these previously scotomata; and/or
b. reducing and/or eliminating distortions of the visual field in the areas of visual space around the scotomata by incorporating these new spatial receptive fields into local spatial maps and by reorganizing them into a continuous, undistorted map of visual space (i.e., counteracting inaccurate perceptual filling-in).

In some embodiments of the exemplary retinal IDM devices and methods described herein, retinal IDM improvement of visual perception occurs by the formation of new visual pathways from functional areas of the retina that encode high fidelity information about regions of visual space, which were, prior to treatment, within scotomata. For example, the distortion of the visual field perceived by patients with macular degeneration can result from an incorrect remapping of the spatial receptive fields of neurons in the central brain. In this remapping, the receptive fields of neurons covering the dysfunctional region of the retina expand and shift to include areas of visual space corresponding to functional regions of the retina. This causes neurons farther away to remap in a similar fashion, and so on. Taken together, these processes induce a global distortion in the receptive field map, with the clinical symptom of straight line objects such as letters, telephone poles and signs becoming wavy, also known as metamorphopsia. After treatment by some embodiments of the exemplary retinal IDM devices and methods described herein, the newly formed receptive fields covering areas of visual space that were, prior to treatment, within scotomata become incorporated into the spatial map within each visual area. This incorporation induces a process of reorganization that reverses the distortion caused by the macular degeneration and thereby restores a continuous, undistorted map of visual space within each visual area. The wavy letters, poles and signs become straight again.

In some embodiments of the exemplary retinal IDM devices and methods described herein, retinal IDM enables beneficial cortical reorganization including, but not limited to, altered crowding properties with smaller critical spacing in the retinal periphery, wherein retinal IDM directs attention to new eccentric preferred loci or other retinal viewing area/s. The altered crowding properties include, but are not limited to, a loss of the radial-tangential anisotropy of the crowding zone. Retinal IDM permits, after spontaneous repeated use of the new preferred retinal location ("PRL") and/or PRLs and/or retinal viewing areas, decreases in the sizes of the crowding zones around the new PRL or PRLs or retinal viewing areas because of cortical plasticity. The plasticity causes the spatial properties at the PRL/PRLs/ retinal viewing areas to become more fovea-like. Both the magnitude and extent of crowding are decreased to the amounts normally found around the fovea. Reduction in the extent of crowding along the major axis contributes to the less elliptical shape of the crowding zone at the PRL/PRLs/ retinal viewing areas, which decreases the detrimental effects of crowding, thereby improving visual acuity and visual function.

Some embodiments of the exemplary retinal IDM devices and methods described herein, unlike conventional devices and methods, improve vision by y awakening, without requiring oculomotor or perceptual training, residual functional vision pathways, thereby enabling patients to discover and use the resulting vision immediately or within days or within weeks and with additional improvement over months.

In some embodiments of the exemplary retinal IDM devices and methods described herein, vision improvement is greatly enhanced by having a pattern of retinal IDM that is stable across time on a moment-to-moment basis as the eyes move naturally in vision.

Some exemplary embodiments, described herein, produce, without requiring perceptual or oculomotor training, natural awareness in a treatment subject of one or more alternate functional visual pathways and natural sensorimotor learning without causing tunnel vision, polyopia or binocular diplopia in a treated subject.

Some exemplary embodiments of the retinal IDM devices and methods described herein stabilize vision and/or reduce, compared to an untreated control group, the rate of vision loss and/or improve vision after a vision loss from a disease, injury or disorder involving retinal cell damage, retinal cell dysfunction, retinal cell sensory deprivation or any combination thereof. The vision improvement includes, but is not limited to, visual acuity (including both uncorrected and best spectacle-corrected visual acuity for distance, intermediate and near visual acuity), hyperacuity, stereoacuity, vernier acuity, contrast sensitivity, depth of focus, color vision, peripheral vision, night vision, face recognition, light adaptation, dark adaptation, vision-related quality of life, or any combination thereof.

In some embodiments of the exemplary retinal IDM devices and methods described herein, retinal IDM enables sustained and/or transient attention. When spatial covert attention is directed to a target location, sustained attention enhances sensitivity strictly via contrast gain, whereas transient attention involves a mixture of both contrast gain and response gain.

In some embodiments of the exemplary retinal IDM devices and methods described herein, retinal IDM improves visual functioning, including, but not limited to, connectivity functions in visual processing of retinal tertiary network cells, including, but not limited to, ganglion cells, amacrine cells, bipolar cells, Müllner cells or any combination thereof.

In some embodiments of the exemplary retinal IDM devices and methods described herein, retinal IDM improves visual field deficits on perimetry and/or microperimetry examination and/or preferential hyperacuity perimetry and/or restores electroretinogram (ERG) amplitudes and/or visually evoked potentials.

Some embodiments of the exemplary retinal IDM devices and methods described herein enable preferred retinal locus or loci relocation to more functional location or locations on an ongoing basis and for different binocular visual tasks.

Some embodiments of the exemplary retinal IDM devices and methods described herein, unlike conventional devices and methods: (i) enable unilateral or bilateral treatment of patients with visual loss from disorders damaging retinal cells and/or decreasing functioning of retinal cells and/or sensorily depriving retinal cells and/or (ii) provide rapid vision improvement continuing over months and years with additional sensory and/or oculomotor neuroadaptation without requiring perceptual or oculomotor control training.

Some embodiments of the exemplary retinal IDM devices and methods described herein, unlike conventional devices and methods with life-threatening or sight-threatening complications or adverse events, provide vision improvement after loss from retinal disorders without complications or adverse events including, but not limited to, clinically significant changes in intraocular pressure, central corneal thickness, corneal endothelial cell density; corneal decompensation, corneal epithelial cell loss, infection or loss of visual functions including, but not limited to, best-corrected distance visual acuity, best-corrected near visual acuity, contrast sensitivity, and stereopsis.

In some embodiments of the exemplary retinal IDM devices and methods described herein that are intended for vision restoration effects including, but not limited to, retinal cell repair and/or retinal regeneration, retinal IDM devices and methods are configured to:

a. decrease by at least 0.1% the retinal irradiance from the field of view on spatially separated retinal areas, including partially or completely dysfunctional retinal areas, wherein the decrease continues over the defined long time scale, and increase by at least 0.1% the retinal irradiance from the field of view on spatially separated (other than those in a.) retinal areas, including more functional retinal areas, wherein the increase continues over the defined long timescale wherein it is understood that retinal irradiance and retinal irradiance distribution can be measured for both model and ex vivo eyes by using photometric instrumentation known to one skilled in the art including, but not limited to, photodiode arrays, charge-coupled device (CCD) sensors and complementary metal oxide semiconductor (CMOS) sensors.

Some embodiments of the exemplary retinal IDM devices and methods described herein improve vision, after loss from disorders damaging retinal cells and/or decreasing functioning of retinal cells and/or sensorily depriving retinal cells, with a single and rapid treatment that is comfortable and pain-free, does not require medication after treatment, and does not require retreatment. By comparison, conventional devices and methods have numerous disadvantages and treatment burdens including, but not limited to, at least one of the following: inconvenience for patients, requirement that the patient remain stationary for usage, limitation to the use of only one eye or only one eye at a time, limitation to treatment only in one eye (or, if the method can be performed in two eyes, only sequential treatment), requirement for a long and/or painful procedure, requirement of post-procedure medications, requirement for constant uncomfortable or difficult insertion, provocation of retinal inflammation, and requirement for multiple/repeat procedures.

Some embodiments of the exemplary retinal IDM devices and methods described herein repair and/or restore retinal cells and/or increase retinal cell functioning and/or decrease progressive damage to retinal cells in addition to significantly improving vision with rapid improvement of neuro-computation and beneficial neuroadaptation continuing long-term (i.e., over a period of time extending from days through years after treatment).

Some exemplary embodiments of the retinal IDM devices and methods described herein compensate for deterioration of the retina caused by photoreceptor or other retinal cell damage with or without repair of retinal cells and/or triggering visual system repair processes, including but not limited to, beneficial modulation of trophic factors and biological repair processes. Biological repair processes include, but are not limited to, regrowth of photoreceptor outer segments, reprogramming of Milner cells, regeneration of retinal cells, and reduction of drusen volume in subjects with diseased photoreceptors, retinal pigment epithelial cells and/or Bruch's membrane.

Some embodiments of the exemplary retinal IDM devices and methods described herein repair and/or restore retinal cells and/or increase retinal cell functioning with fewer adverse effects and more patient convenience. One or more of the exemplary retinal IDM devices and methods described herein overcome drawbacks and deficiencies of the prior art, including conventional devices and methods for repairing retinal cells or increasing retinal cell function or decreasing progressive retinal cell damage by targeting different mechanisms with the novel retinal IDM to produce better treatment outcomes more comfortably and more conveniently with fewer systemic and ocular adverse effects. In some exemplary embodiments, described herein, retinal IDM not only improves vision by altering neurocomputation and neuroadaptation but also by repairing and/or restoring retinal cells. In some embodiments, described herein, retinal IDM also triggers visual system repair processes, including biological repair processes, including, but not limited to, regrowth of photoreceptor outer segments, reprogramming of Müller cells, regeneration of retinal cells and reduction of drusen volume, wherein the retinal IDM a. decreases by at least 0.1% retinal irradiance from the field of view of spatially separated retinal areas within at least one of a foveal area, another PRL, multiple PRLs, a non-PRL retinal area, multiple non-PRL retinal areas or any combination thereof, wherein the decrease continues over the previously defined long timescale, wherein the reduced retinal irradiance decreases deleterious processes including, but not limited to, photo-oxidative stress, metabolic stress or a combination thereof within viable retinal cells, wherein reduction of such deleterious processes includes, but is not limited to, sparing photoreceptors, slowing progression of photoreceptor loss, decreasing drusen volume or any combination thereof; and b. increases by at least 0.1% retinal irradiance from the field of view on retinal areas (other than in a.), including on areas with viable retinal cells, wherein the increase continues over the previously defined long timescale, wherein the increased retinal irradiance increases activation by the viable cells of at least one of cell repair, cell regeneration, or a combination thereof within at least one of damaged retinal cells or retinal areas with non-functional cells; and c. redirects spatial, temporal, spatiotemporal, chromatic, achromatic and contrast information contained in irradiance distributions from one or more dysfunctional to one or more functional areas of the retina.

In some exemplary embodiments, described herein, retinal IDM improves retinal sensitivity, wherein the improved retinal sensitivity includes, but is not limited to, improved sensitivity of viable cone photoreceptors, viable rod photoreceptors, viable ganglion cells, amacrine cells, viable bipolar cells and/or partially or completely regenerated retinal cells. It is understood that retinal sensitivity can be measured by one skilled in the art by using diagnostic instrumentation including, but not limited to, microperimetry instrumentation. In some exemplary embodiments, described herein, retinal IDM produces in a treated eye with a retinal disorder, including, but not limited to, macular degeneration, over a time period of months or years at least one of the following: a. an increase in retinal sensitivity in a retinal region, b. a decrease in the rate of retinal sensitivity loss compared to an untreated control group, c. a decrease in the rate of photoreceptor loss compared to an untreated control group, d. a decrease in the area of photoreceptor loss, e. a decrease in drusen volume, f a regeneration of retinal cells, or g. any combination thereof.

In some exemplary embodiments, described herein, retinal IDM increases retinal absorption of photons in some retinal areas to improve visual processing for vision and retinal image quality while decreasing cumulative photoabsorption and photodamage in other retinal areas, including, but not limited to, the foveal area, other fixation areas, other macular areas, peripheral areas and any combination of retinal areas in which cumulative photoabsorption and photodamage should be reduced.

In some exemplary embodiments, described herein, retinal IDM selectively decreases light irradiance including, but not limited to, on the fovea, on other fixation areas (preferred retinal loci), on other macular areas, on peripheral retinal areas, and on any combination of retinal areas to selectively decrease oxidative stress and/or phototoxicity to retinal structures including, but not limited to, photoreceptors, retinal pigment epithelial cells, Bruch's membrane and choriocapillaris and/or selectively decreases cumulative light damage, by decreasing oxidative stress and/or phototoxicity including, but not limited to, in the fovea, in other fixation area/s (preferred retinal loci), in other macular areas, in peripheral retinal areas, or in any combination of retinal areas.

In some exemplary embodiments, described herein, retinal IDM provides beneficial effects including, but not limited to, selective prevention of photoreceptor loss, selective reduction of the rate of progression of photoreceptor loss, and decrease of photoreceptor loss including, but not limited to, apoptosis and/or necrosis and/or pyroptosis and/or autophagy.

In some exemplary embodiments, described herein, retinal IDM selectively reduces light-induced oxidative stress and reactive oxygen species in the retinal areas where irradiance is decreased in order to produce beneficial effects including, but not limited to, protection of photoreceptor DNA, promotion of DNA repair, decrease of pathophysiological parainflammation, decrease of inflammasome activation, decrease of detrimental autophagy, including but not limited to, chaperone-mediated autophagy (a.k.a. microautophagy), decrease retinal cellular death via apoptosis, decrease activation of proinflammatory and proangiogenic pathways, decrease other deleterious processes associated with oxidative stress and its resultant excessive reactive oxygen species.

In some exemplary embodiments, described herein, retinal IDM selectively decreases photo-oxidation of the retinoid A2E in photoreceptor outer segments. In some exemplary embodiments, described herein, retinal IDM selectively decreases A2E formation and/or promotes A2E reduction in photoreceptor outer segments without the adverse ocular events related to delayed dark adaptation, such as nyctalopia, dyschromatopsia, blurred vision and photophobia, of current investigational drugs that reduce A2E formation.

In some exemplary embodiments, described herein, retinal IDM selectively decreases retinal irradiance and/or cumulative retinal irradiance in retinal areas to decrease oxidative phosphorylation in retinal areas to decrease reactive oxygen species, thereby preventing mitochondrial dysfunction and/or reversing mitochondrial dysfunction. In some exemplary embodiments, described herein, retinal IDM reduces metabolic and/or oxidative stress and/or metabolic instability of retinal structures including, but not limited to, retinal cells (including, but not limited to, photoreceptors, retinal pigment cells, Milner glial cells, and ganglion cells) and Bruch's membrane in some retinal areas to produce beneficial effects including, but not limited to, reduction of damage to and/or repair of and/or regeneration of damaged retinal structures including, but not limited to, retinal cells (including, but not limited to, photoreceptors, retinal pigment cells, Müller glial cells, and ganglion cells) and Bruch's membrane in some retinal areas.

In some exemplary embodiments, described herein, retinal IDM selectively decreases retinal irradiance and/or cumulative retinal irradiance in some retinal areas and/or decreases oxidative stress to produce beneficial effects including, but not limited to, harnessing Milner glial cells for photoreceptor cell protection and/or regeneration and/or increasing Milner glial cell transdifferentiation and/or decreasing Müller glial cell gliosis and/or preventing deleterious retinal remodeling and/or preserving glutamine synthetase expression in Müller cells and/or enabling the retinal microenvironment around Müller cells to support cone function.

In some exemplary embodiments, described herein, retinal IDM selectively decreases retinal irradiance and/or cumulative retinal irradiance in some retinal areas, thereby causing reduction of drusen volume (i.e., the number and/or size of drusen).

In some exemplary embodiments, described herein, retinal IDM selectively decreases retinal irradiance and/or cumulative retinal irradiance in some retinal areas to produce beneficial effects including, but not limited to, beneficial modulation of trophic factors and regeneration and/or rescue of retinal structures including, but not limited to, retinal cells (including, but not limited to, photoreceptors, retinal pigment epithelial cells, Müller glial cells, and ganglion cells) and Bruch's membrane and the external limiting membrane.

Exemplary embodiments described herein include retinal IDM devices and methods based on light sources (including, but not limited, to continuous wave and pulsed lasers, including, but not limited to, lasers for corneal photodisruption, intralenticular photodisruption, corneal photoionization, corneal photodissociation, corneal photoablation, thermal keratoplasty, and photo-welding), corneal crosslinking systems, corneal radiofrequency transmitters, spectacles, contact lenses, corneal inlays, intraocular lenses for insertion in phakic, aphakic or pseudophakic eyes, and combinations thereof configured to produce retinal irradiance distribution patterns utilizing designs, materials, and optics for retinal IDM in many areas of the retina or throughout the retina to stabilize vision, improve vision, restore vision or reduce the rate of vision loss compared to an untreated control group after visual loss from disorders that involve damaged and/or dysfunctional and/or sensorily deprived retinal cells; wherein the retinal IDM devices and methods are configured to optically modify permanently, temporarily or with variable modifications over time in at least three retinal regions, including the fovea or another retinal fixation region, spatial, temporal, spatiotemporal, chromatic, achromatic and contrast information distributions of environmental light from an ocular field of view by means of simultaneous light redirections from the fovea or another retinal fixation region to at least two other spatially separated retinal regions, wherein the retinal regions are defined by ranges of polar coordinates, wherein the spatially separated retinal regions are non-overlapping regions, partly overlapping regions or any combination of non-overlapping and partly overlapping regions and wherein the amount(s) and location(s) of retinal IDM are for predetermined spatial distribution(s) with or without predetermined temporal distributions and wherein the retinal irradiance distribution modifications contain information including, but not limited to, spatial, temporal, spatiotemporal, chromatic, achromatic and contrast information or any combination thereof. In some embodiments of the retinal IDM devices and methods described herein, the retinal devices produce retinal IDM to simultaneously and optically redirect light from partly or completely dysfunctional retinal areas and to redirect that light, in whole or in part, onto one or more functional retinal areas, wherein the retinal irradiance distribution modifications contain information including, but not limited to, spatial, temporal, spatiotemporal, chromatic, achromatic and contrast information or any combination thereof. In some exemplary embodiments of the retinal IDM devices and methods described herein, the retinal devices produce retinal IDM wherein the amount and location of retinal IDM is for spatially separated retinal areas, that are non-overlapping areas, partly overlapping areas or any combination of non-overlapping and partly overlapping areas; the amount and location of such retinal IDM is for a predetermined spatial distribution with or without a predetermined temporal distribution; wherein the amount and location of retinal IDM has a pattern and symmetry distinct from that caused by self-generated image modifications including, but not limited to, i) eye movements that cause a single translation of the entire visual field on the retina, ii) lens accommodation that causes a change in the focus of the entire visual field on the retina and iii) pupil dilation/constriction that causes a rapid brightening/dimming of the entire visual field on the retina, as this prevents the central brain from being able to compensate for, and hence partially cancel, the effects of retinal IDM; wherein retinal IDM, without requiring oculomotor and/or perceptual training, inhibits at least one visual pathway used for fixation and excites at least one alternate functional visual pathway for fixation in an eye; wherein retinal IDM, without requiring oculomotor and/or perceptual training, produces awareness in a treatment subject of at least one or multiple alternate functional visual pathways; wherein retinal IDM also may produce beneficial effects including, but not limited to, reduction of damage to and/or repair of and/or regeneration of damaged retinal structures including, but not limited to, retinal cells (including, but not limited to, photoreceptors, retinal pigment cells, Müller glial cells, and ganglion cells) and Bruch's membrane in some retinal areas; and wherein retinal IDM improves vision after a vision loss from one or more of a disease, injury or disorder involving one or more of retinal cell damage, retinal cell dysfunction, retinal cell sensory deprivation or any combination thereof, wherein the improved vision is configured to result in improvement of vision-related outcomes including, but not limited to, visual acuity (including both uncorrected and best spectacle-corrected visual acuity for distance, intermediate and near visual acuity), hyperacuity, depth of focus, color vision, peripheral vision, contrast sensitivity, stereoacuity, vernier acuity, light adaptation, dark adaptation, vision-related quality of life, or any combination thereof.

Figure 7:
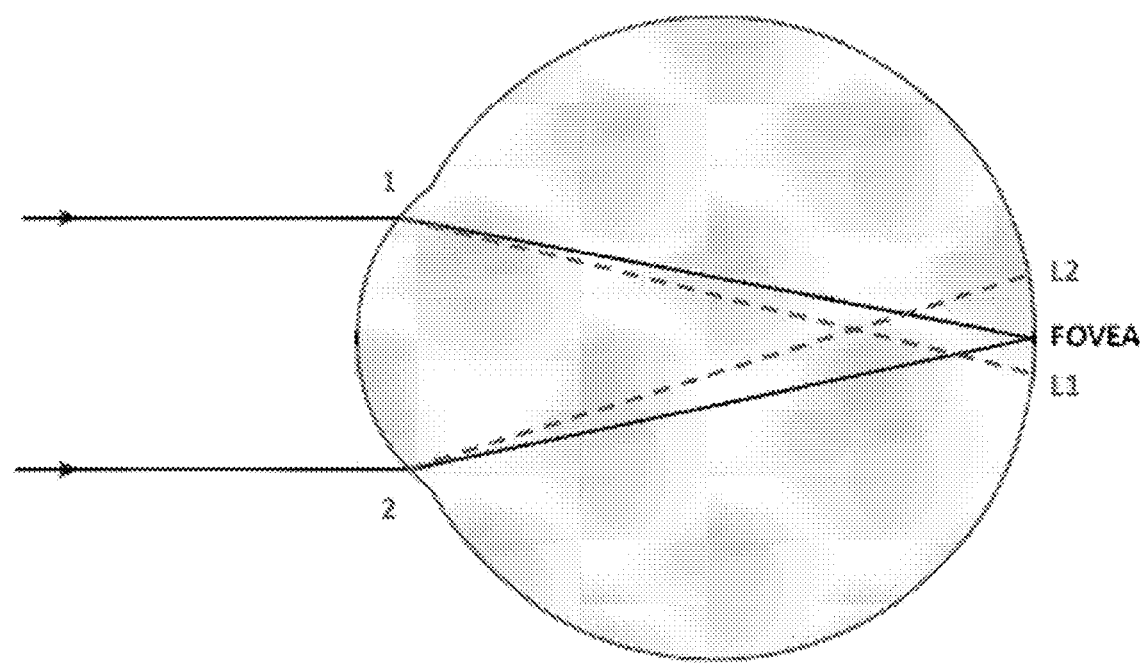
FIG. 7 is a schematic eye drawing with two light rays incident on the paracentral cornea at points 1 and 2.

Some of the exemplary retinal IDM devices and methods described herein alter the cornea of the eye. In some corneal embodiments, a laser retinal IDM device is used to modify radii of curvature (ROCs) of the cornea as schematically shown in FIG. 7. In the unmodified cornea, rays of light incident on points 1 and 2 are focused onto the fovea, as shown by solid lines in FIG. 7. Decreasing the ROCs at points 1 and 2 (not shown in FIG. 7) changes the directions of light rays to irradiate locations L1 and L2 that are outside the fovea. In FIG. 7, the modified ROC at point 2 is decreased by a greater amount compared to the modified ROC at point 1, both of which are decreased relative to the unmodified radius of curvature; in this case, the greater decrease in radius of curvature at point 2 produces a larger redirection of the light ray to irradiate location L2 that is separated by a greater distance from the fovea than the light ray that irradiates location L1. The light ray relocations at any points on the cornea can be produced by corneal modifications including, but not limited to, modifications of corneal radii of curvature, corneal indices of refraction, corneal diffraction, corneal scattering and any combination of corneal modifications thereof. It is understood that the sample light rays shown in FIG. 7 are only representative of the entire set of light rays that are mapped from object space to image space(s) on the retina. In some exemplary embodiments, described herein, retinal IDM includes light ray relocations produced by corneal modifications within two or more corneal regions including, but not limited to, central through paracentral sectors extending to 7 mm or larger optical zone with alternating steeper and flatter sectors within the full 360° angular range on the cornea.

Figure 8:
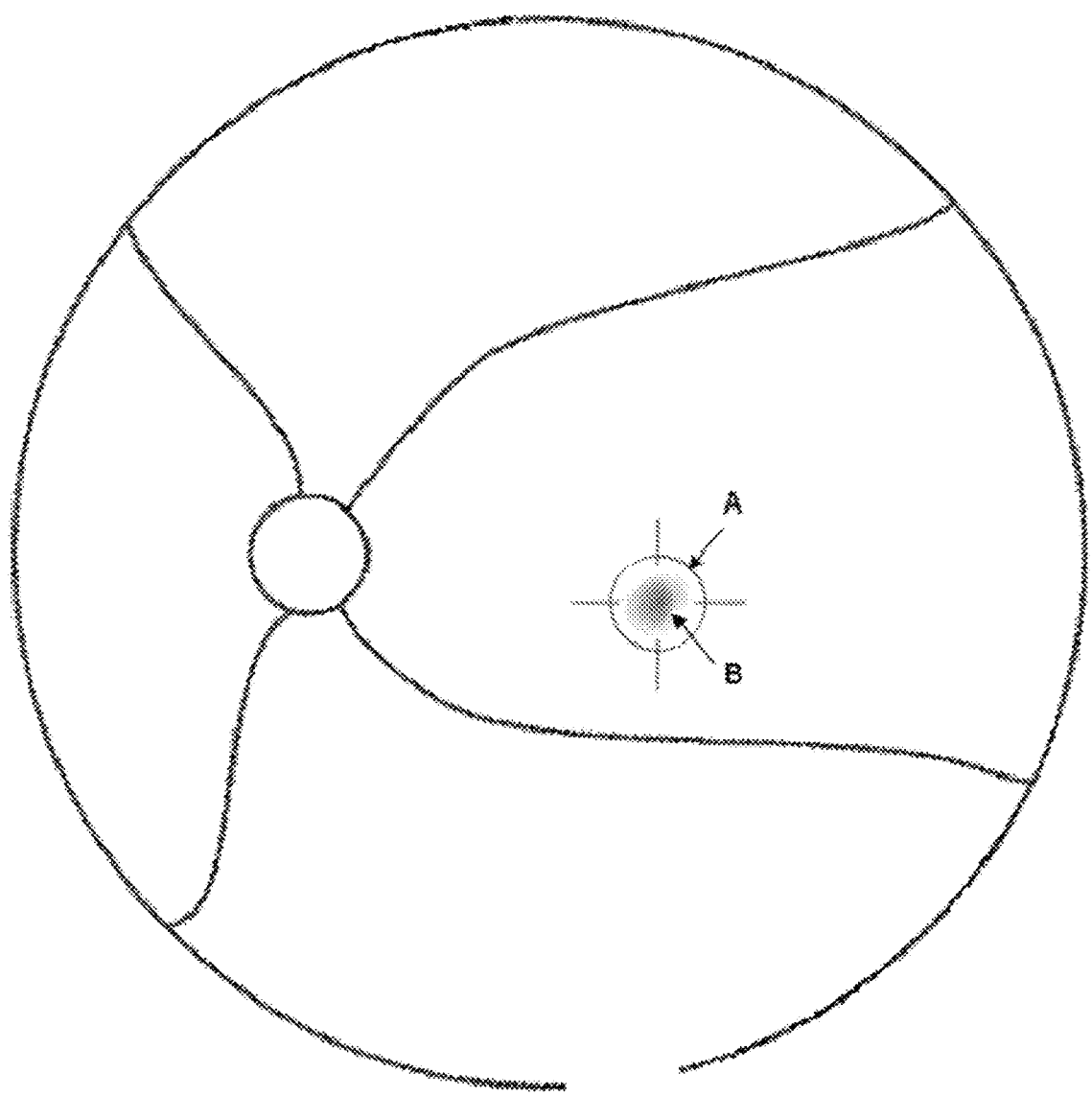
FIG. 8 is a schematic retina drawing showing the fovea A with a central dysfunctional retinal area B.
Figure 9:
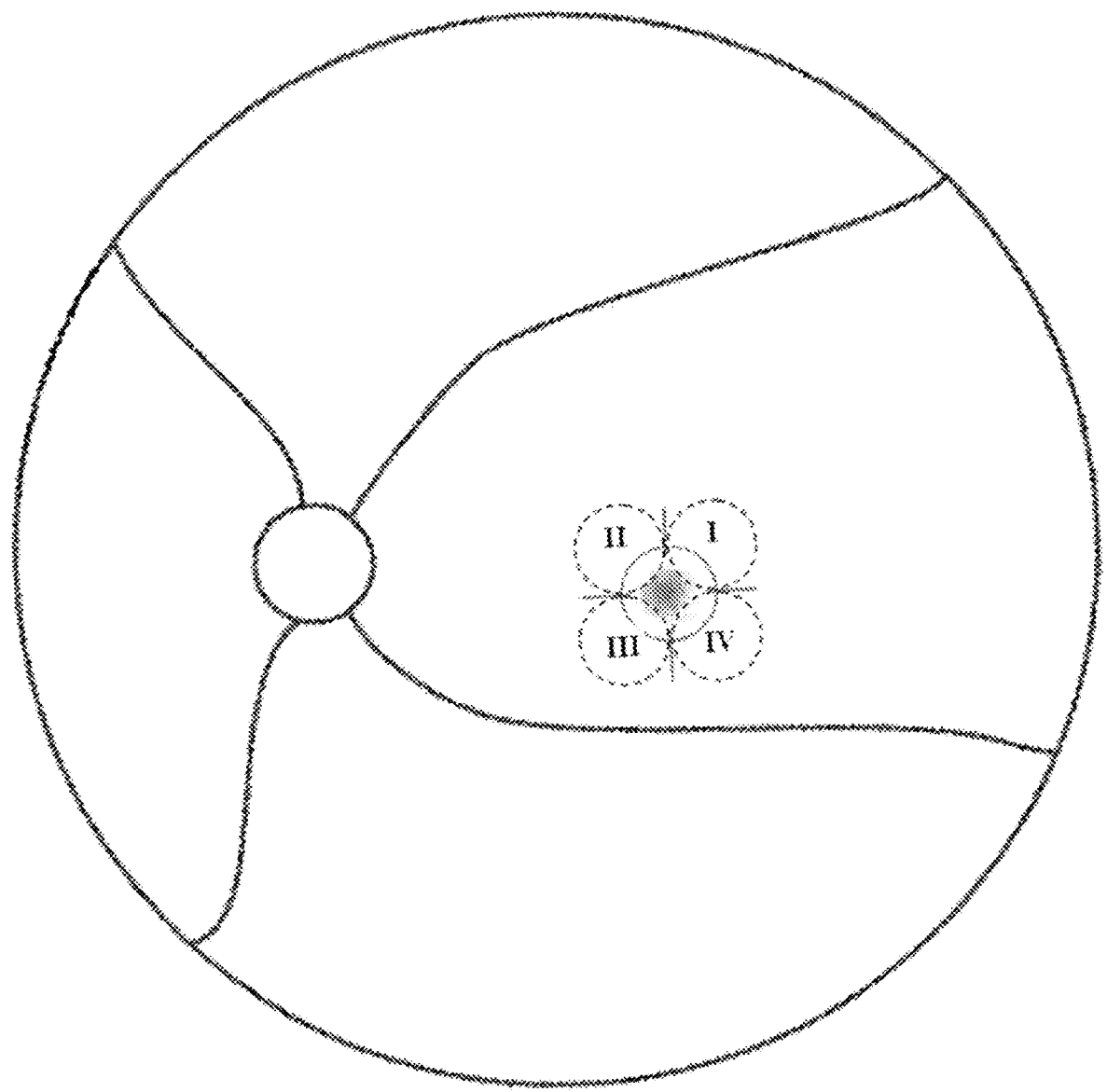
FIG. 9 is a schematic retina drawing showing a four-quadrant retinal irradiance distribution from a central area into quadrants I through IV.

FIG. 8 is a schematic retina drawing showing the fovea A with a central dysfunctional area B. In this case, a retinal IDM device including, but not limited to, a device that modifies the cornea should be designed to redirect light rays, with spatiotemporal, contrast, chromatic and achromatic information, away from the central dysfunctional area B to functional retinal areas including, but not limited to, the functional zone of the fovea outside area B. FIG. 9 is a schematic retina drawing that illustrates a four-quadrant retinal IDM that may be produced by using a retinal IDM device for retinal IDM from the central dysfunctional retinal area into four functional retinal areas.

Figure 10:
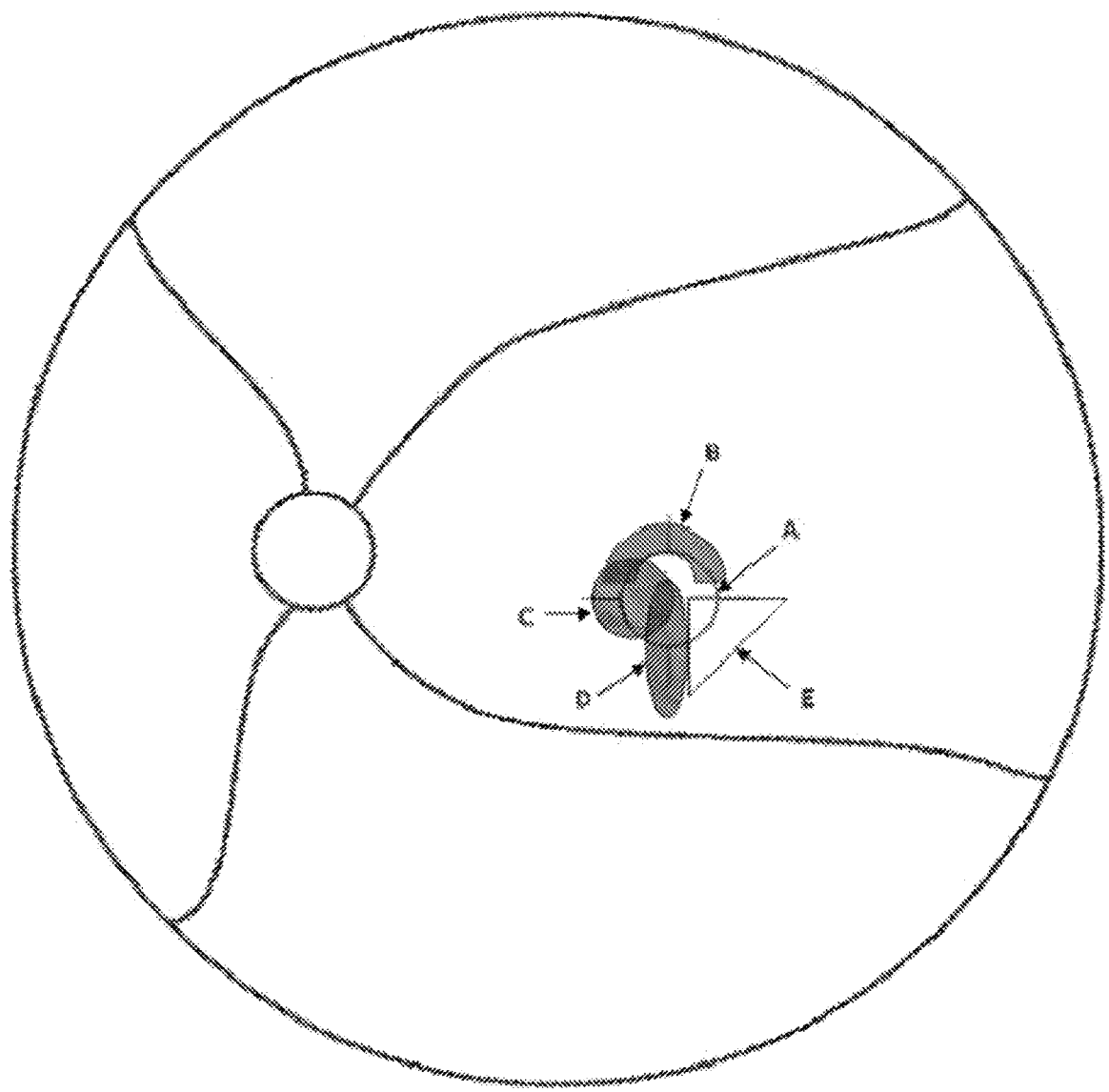
FIG. 10 is a schematic retina drawing showing the fovea A with non-central dysfunctional retinal areas B, C and D and a candidate functional retinal area E into which retinal IDM can increase retinal irradiance by directing irradiance away from B, C and D.

FIG. 10 shows dysfunctional and functional retinal areas with a variety of shapes and locations on the retina. It is understood by anyone skilled in the art that any retinal IDM device should be configured to produce retinal IDM away from dysfunctional retinal areas (B, C and D in the example of FIG. 10) and onto functional retinal areas; in the case of FIG. 10, the functional retinal area E is a candidate area into which retinal IDM can be used for vision and visual function improvements.

Figure 11A:
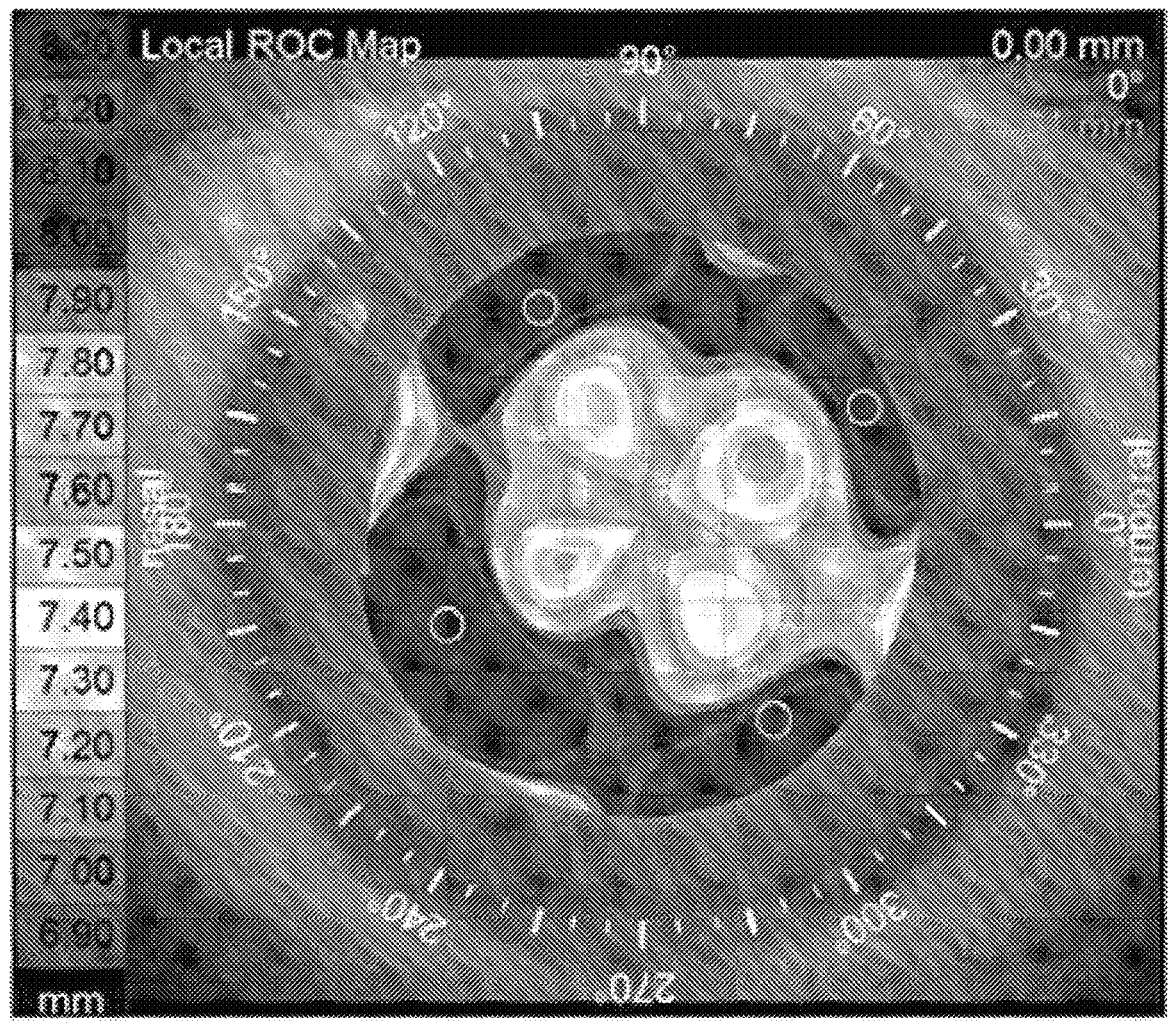
FIG. 11A is a corneal map showing local radii of curvature after an IDM treatment.
Figure 11B:
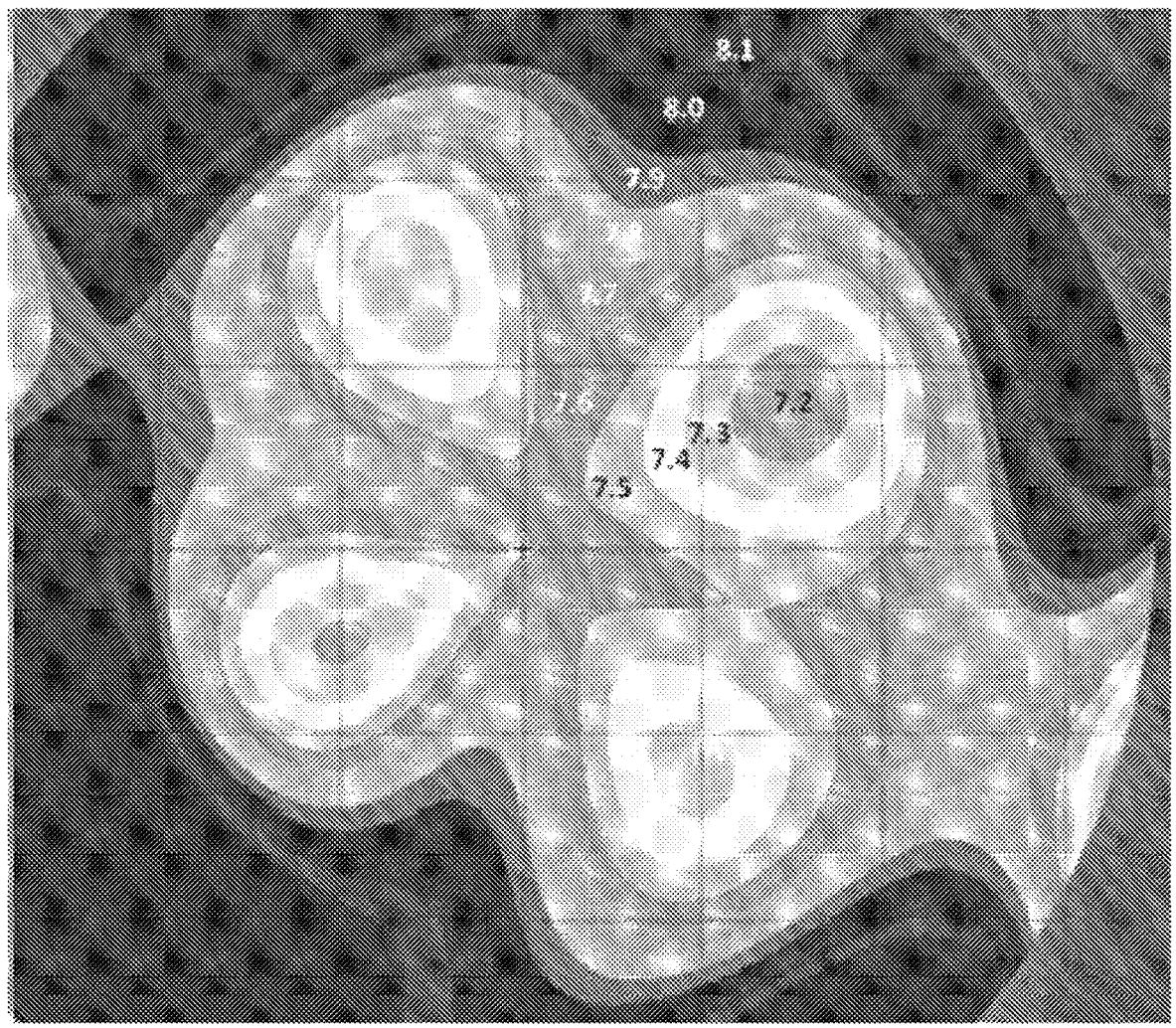
FIG. 11B shows an enlarged central area of FIG. 11A.
Figure 12:
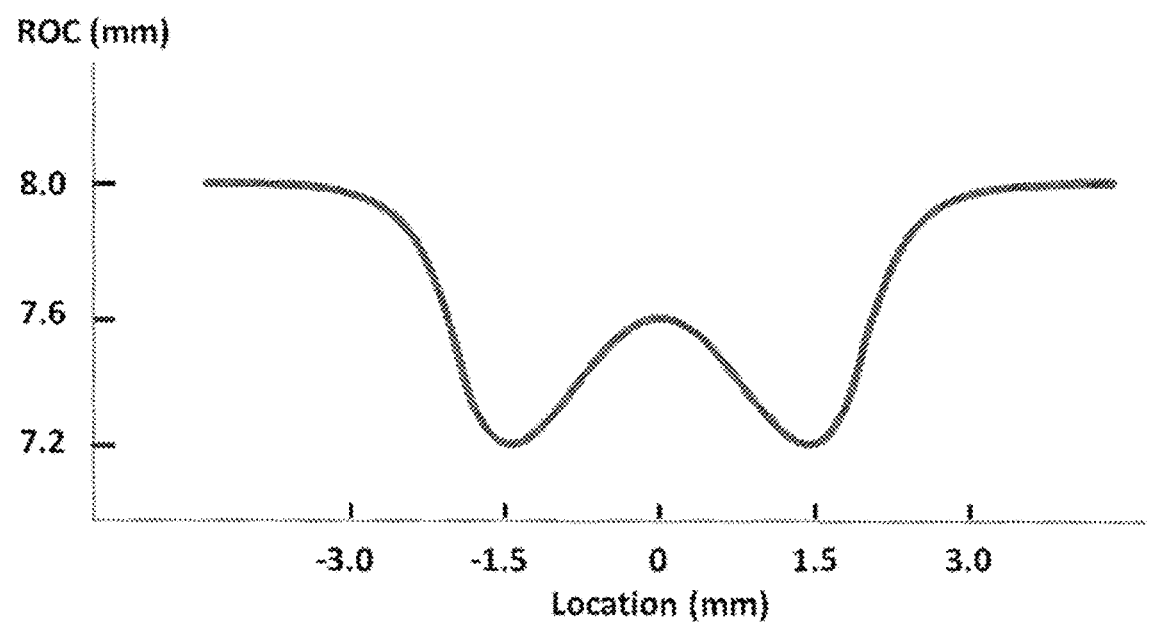
FIG. 12 shows a schematic corneal anterior surface radius of curvature (ROC) profile for retinal IDM.

Some embodiments of a retinal IDM device and method produce the treatment pattern of corneal radii of curvature (ROC) shown in FIG. 11A and the enlarged portion of FIG. 11A shown in FIG. 11B. FIG. 11B shows 0.1 mm incremental boundaries in radii of curvature; the actual ROCs vary continuously from one incremental boundary to another. FIG. 12 shows a continuous ROC profile that approximates the ROC profile along the 30°-210° meridian of the treatment pattern shown in FIG. 11A. The ROCs can be symmetric as shown in FIG. 12 or asymmetric with variable shapes. Locations of minimum ROCs can be centered or decentered with respect to the pupil centroid (or another centration reference). As an example, if an untreated cornea has a ROC of approximately 7.6 mm in the central optical zone (within 3 mm diameter); the treated cornea could have ROCs in the range of 7.2 to 7.8 mm within the same zone. Some embodiments of IDM treatment also produce significant ROC changes throughout the cornea, extending to the peripheral cornea at the 7 mm optical zone. A resultant IDM treatment change, as shown in FIG. 11A, can be approximately described as four sets of alternating steeper/flatter sectors within the central (3 mm diameter) optical zone surrounded by four sets of flatter regions in the paracentral cornea between ca. 5 to 7 mm optical zone. The variations in ROCs produce redirection of light rays from four aspheric extended "lenslets" that redirect retinal irradiance onto functional retinal areas similar to those illustrated in FIG. 9, as well as redirection of light rays from other regions of the cornea. The ROC pattern shown in FIGS. 11A and 11B are produced by a retinal IDM device causing IDM treatment of four small volumes of corneal stromal tissue located underneath the surface treatment areas shown as small white circles on FIG. 11A. Due to the biomechanical properties of the cornea, the highly localized treatments in four small volumes of corneal stromal tissue produce non-local effects that extend from each treated volume toward the corneal center with peak effects approximately midway between the treated volumes and the corneal center. Some embodiments of IDM treatment produce non-local ROC changes over the entire cornea extending from the center of the cornea to at least the 7 mm optical zone.

In some exemplary embodiments, described herein, devices for retinal IDM produce corneal modifications including, but not limited to, modifications of corneal radii of curvature, corneal indices of refraction, corneal diffraction, corneal scattering and any combination of corneal modifications thereof throughout the cornea using various patterns, including but not limited to four circular non-central volume treatments. In corneal radii of curvature modifications, IDM treatment induces various non-central locations and amplitudes of major depressions and/or elevations in the corneal anterior surface with resultant increases and/or decreases in anterior corneal radii of curvature throughout the cornea.

In some exemplary embodiments, described herein, retinal IDM produces changes in radii of curvature that alter the irradiance distribution in all four quadrants of the retina, wherein retinal IDM causes decreased or increased irradiance and/or contrast on retinal regions and/or microregions, wherein the changed ratios of light and dark edges of viewed objects change the irradiance contrast. In some embodiments, exemplary patterns for retinal IDM are centered on the pupil centroid (PC) or corneal vertex (CV) or coaxially sighted corneal light reflex (CSCLR). In some embodiments, patterns for retinal IDM are decentered relative to the PC, CV or CSCLR.

In some exemplary embodiments, described herein, retinal IDM does not produce deleterious retinal effects including, but not limited to, retinal inflammation and retinal wound healing. In contrast to conventional devices and methods of retinal laser therapy (including, but not limited to, laser retinal photocoagulation, laser retinal photodynamic therapy and subthreshold micropulse diode laser therapy) and photobiomodulation therapy, some embodiments of IDM devices and methods do not use laser or light emitting diode (LED) light to irradiate the retina; some IDM embodiments use only natural environmental light to irradiate the retina and therefore are free from deleterious retinal effects associated with exposure of the retina to laser and other unnatural non-environmental light. In some embodiments of IDM treatments f, only "eyesafe" light is used to irradiate the cornea; "eyesafe" light is completely absorbed by the cornea and other pre-retinal ocular structures, thereby preventing direct irradiation of the retina.

In some exemplary embodiments, described herein, retinal IDM continues to compensate for ongoing damage to or decreased functioning of retinal cells from the underlying disease process for months and years after the treatment. In some embodiments, the ongoing neural compensation for ongoing damage to retinal cells or decreased functioning of retinal cells from the underlying disease process is facilitated by ongoing changes in the retinal IDM produced by one or more of the exemplary methods described herein, which, for example, enable changes in corneal anterior surface depressions and/or elevations over days, weeks, months, or years. Some of the curvature of the anterior cornea throughout the cornea, that change gradually over days, weeks, months, or years to continue to compensate for ongoing damage to or decreased functioning of retinal cells.

In some exemplary embodiments, described herein, the amplitudes of the corneal ROC changes from IDM treatment diminish over time. In some exemplary embodiments, described herein, the IDM treatment can be modified by changing the treatment pattern and/or treatment energy density delivered to the cornea in order to make the IDM changes of corneal ROC temporary for different periods of time. Temporary IDM-induced ROC changes are particularly useful for treatment of amblyopia in children, adolescents and young adults. IDM treatment of both eyes of a subject with amblyopia can prevent vision impairment produced by conventional amblyopia treatment with monocular deprivation. IDM treatment of both eyes of a subject with amblyopia can improve binocularity during normal daily functions, in contrast to conventional single eye methods. Binocularity is impeded by monocular deprivation treatment for amblyopia and is not improved during normal daily functions when conventional binocular visual training is performed with or without video games. IDM treatment of both eyes of a subject does not prevent use of both eyes' peripheral vision. The peripheral vision of a subject with amblyopia usually is normal, can be impaired by occlusion therapy, and can contribute to improvements in central vision in the amblyopic eye after IDM treatment.

In an application of some embodiments of the retinal IDM device, IDM treatments on eyes with age-related macular degeneration (AMD) using a treatment pattern similar to that of FIG. 11A produce significant retinal IDM vision improvements in mean best-spectacle corrected distance and near visual acuities (CDVA and CNVA), in contrast sensitivity and other visual functions, and in vision-related quality of life. Distance and near versions of the ETDRS chart are available to measure distance and near visual acuities, respectively. ETDRS measurements are reported in several ways: in terms of Snellen values, log MAR values, decimal values and/or the number of letters correctly read (starting with 0 letters for a Snellen value of 20/1000). Improvements in visual acuity are often reported in terms of letters gained and/or lines gained on the ETDRS chart; there are 5 letters per line on the chart.

It can be appreciated by anyone skilled in the art that individual customized retinal IDM treatments can be performed by one or more of the exemplary retinal IDM devices and methods described herein. These individual customized retinal IDM treatments can be based on diagnostic information including, but not limited to, individual optical coherence tomography, microperimetry, high definition perimetry and fundus autofluorescence examinations.

In some embodiments described herein, retinal IDM treatment patterns can be configured based on the extent of macular damage and visual field loss in order to improve vision of patients with glaucoma. Glaucomatous damage to the macula occurs early in the disease process and is more common in the upper visual field where local and deep arcuate defects can appear near fixation. Early glaucomatous damage produces significant reduction in binocular contrast sensitivity scores and depth perception which may be improved by bilateral retinal IDM.

Figure 13:
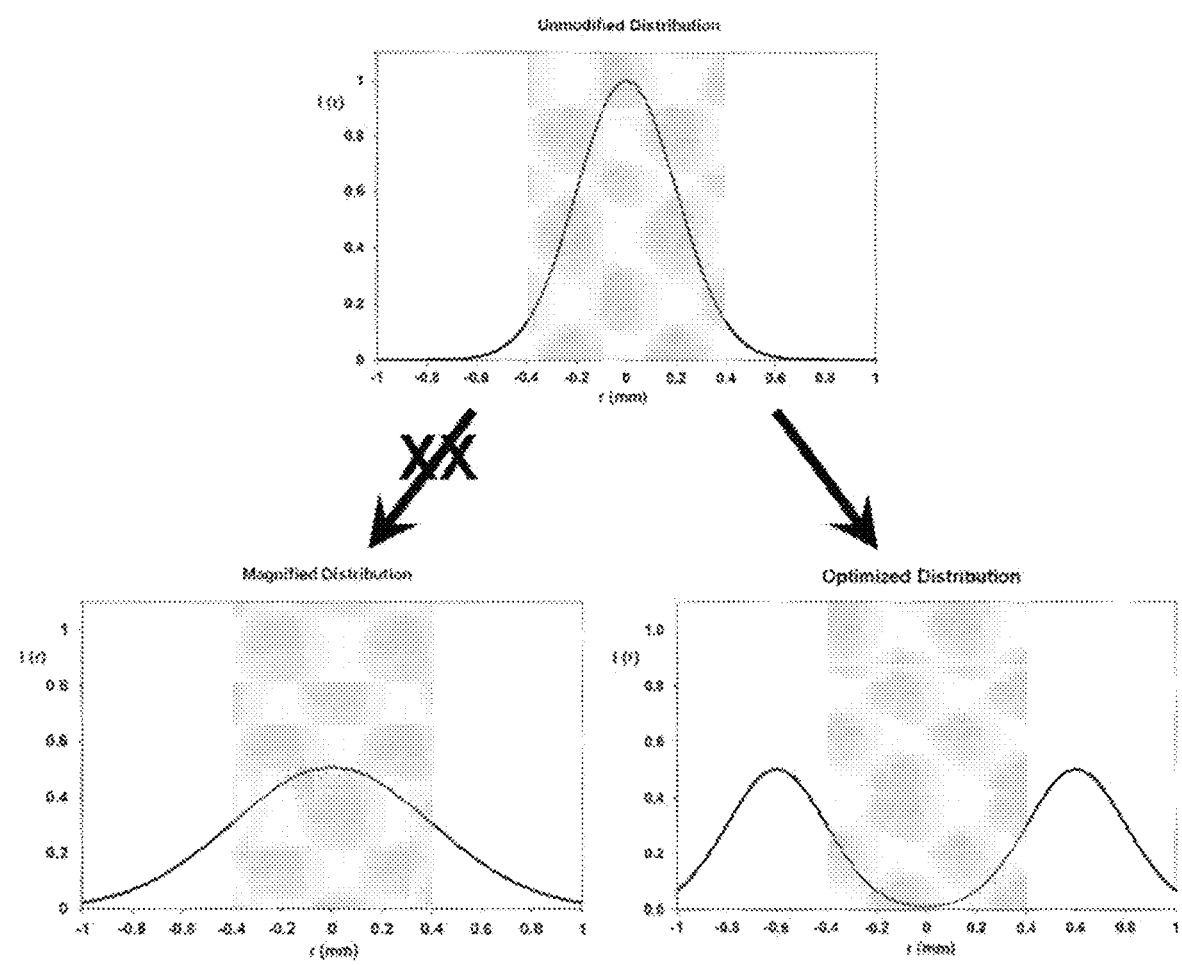
FIG. 13 shows cross-sections through schematic retinal irradiance distributions.

FIG. 13 shows unmodified and modified retinal irradiance distributions with a schematic illustration of the effect of a central dysfunctional retinal area (shaded gray). In the unmodified retinal irradiance distribution (top graph), only a small portion (4.3%) of the light irradiates the functional retinal area that is outside the dysfunctional retinal area. Conventional modification by 2× magnification such as is produced by IMT implantation (bottom left graph) increases the useful retinal irradiance to 30% that is outside the dysfunctional retinal area and inside the functional retinal area. Optimized modification described herein (bottom right graph) produces retinal IDM similar to that shown in FIG. 7, increasing the useful retinal irradiance to 83% that is outside the dysfunctional retinal area and thus inside the functional retinal area. Conventional modification by magnification, the basis of IMT and similar intraocular telescope devices, is always limited in effectiveness to improve vision for eyes with central vision loss. In addition, the IMT device causes "tunnel vision" due to the restricted field of view of the telescope optics. Corneal treatment by some of the exemplary embodiments, described herein, is much more effective in improving vision for eyes with central vision loss and also improves peripheral vision rather than causing "tunnel vision".

Some exemplary embodiments, described herein, involve IDM devices and methods that are configured to produce corneal modifications including, but not limited to, modifications of corneal radii of curvature, corneal indices of refraction, corneal diffraction, corneal scattering and any combination of corneal modifications thereof for light redirections away from the fovea or another retinal fixation region to at least two other retinal regions for retinal IDM. These embodiments include, but are not limited to, corneal devices and methods for corneal photodisruption, corneal photoionization, corneal dissociation, corneal photoablation, photothermal keratoplasty (LTK), corneal photowelding, corneal crosslinking (CXL), conductive keratoplasty (CK), and corneal inlays, all of which are configured for retinal IDM. For optimal retinal IDM, the changes of radii of curvature and/or refractive indices should produce as much retinal IDM as possible outside of dysfunctional retinal areas and inside functional retinal areas. IDM treatment devices and methods can be configured to produce corneal radii of curvature (ROC) changes including, but not limited to those shown in FIGS. 11 and 12, for corneal anterior surface ROC changes for retinal IDM. IDM treatment and devices can be configured to produce lenticular radii of curvature or indices of refraction modifications of the natural crystalline lens for retinal IDM using devices, including, but not limited to, a femtosecond laser for photodisruption. It is understood that corneal modifications can be made initially (the first modification) and at later times (the subsequent modifications).

Figure 14:
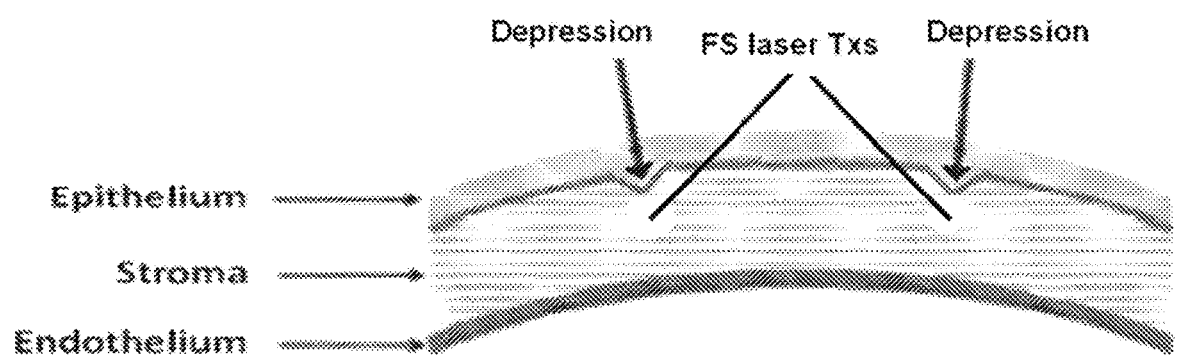
FIG. 14 shows a cross-section of a cornea after femtosecond laser treatments to produce corneal anterior surface radius of curvature (ROC) changes for retinal IDM.

In some exemplary embodiments, described herein, femtosecond (FS) lasers or nanosecond leasers can be used to produce intrastromal photodisruptions or photoionizations or photodissociations or any combination thereof for retinal IDM by means of corneal modifications. FIG. 14 illustrates a schematic cross-section through a cornea that has received a femtosecond (FS) laser treatment (Tx) pattern configured to produce retinal IDM. In the example shown, intrastromal FS laser irradiations are configured to remove intrastromal corneal volumes that lead to depressions (exaggerated in depth in FIG. 14) and, hence, radius of curvature (ROC) changes in the anterior corneal surface; as an alternative, FS laser irradiations can be configured to produce other corneal modifications including, but not limited to, intrastromal index of refraction modification, intrastromal diffraction modification and intrastromal scattering modification for retinal IDM; any combination of corneal modification changes can be used for retinal IDM. FS laser patterns for corneal tissue removal or changes in index of refraction can be spherical as shown in FIG. 14 or can have any volumetric shape. FS treated volumes can be located at any depth within the corneal stroma. Two or more FS treated volumes can be generated centrally (within the 3 mm optical zone), paracentrally (within the 3 to 6 mm optical zone) or peripherally (at >6 mm optical zone), with centration or decentration of the treatment pattern with respect to the pupil centroid or another centration reference. The treated volumes can be equal or unequal in shape and/or depth to produce custom effects. Unlike FS annular intrastromal treatments previously used for other applications such as presbyopia correction, the FS laser modifications are not 360 degree annular volumes and, therefore, do not induce corneal ectasia.

In some exemplary embodiments, described herein, laser tissue removal procedures including, but not limited to, laser photodisruption, photoionization or photodissociation and/or laser photoablation devices and methods [including, but not limited to, Small Incision Lenticule Extraction (SMILE), Laser In-Situ Keratomileusis (LASIK) and PhotoRefractive Keratectomy (PRK) devices and methods] can be used to produce corneal modifications that are useful for retinal IDM. FIG. 12 shows a cross-section through a cornea with an anterior surface ROC profile that is configured to be useful for retinal IDM. Laser tissue removal procedures (including, but not limited to, femtosecond laser treatment to form a corneal lenticule for SMILE treatment, and laser photoablation of the stromal bed for LASIK treatment and for PRK treatment) should be configured to produce corneal modifications that are sufficient to provide retinal IDM.

In some exemplary embodiments, described herein, corneal crosslinking devices, including but not limited to ultraviolet A (UVA) light emitting devices, LTK devices, and other devices that can be combined with a photosensitizer, including, but not limited to, riboflavin, or other photoactivation systems with photoactivation agents, including, but not limited to, glyceraldehyde, glutaraldehyde, genipin, nitroalcohols or formaldehyde-releasing agents, for corneal crosslinking (CXL) procedures are configured to produce focal areas of crosslinking (FCXL) In some embodiments of a FCXL IDM procedure, corneal areas that are not to be treated are masked from UVA light or other light or photoactivator in two or more spatially separated treatment areas of the cornea for the application of retinal IDM. FCXL may be performed with or without removal of the corneal epithelium, in whole or in part, to enhance the penetration of a photosensitizer into the corneal stroma, including, but not limited to, administration of a photosensitizer (including, but not limited to, riboflavin) to the cornea followed by UVA or other light irradiation. FXCL can also be produced by using combined laser thermal keratoplasty plus CXL using photosensitizers including, but not limited to, riboflavin that is activated by high irradiance (10 W/cm$^2$ or greater irradiance) visible or UVA light sources including, but not limited to, GaN diode lasers and diode-pumped solid state (DPSS) lasers operating in the 360 to 460 nm wavelength region. FXCL IDM devices and methods are configured to produce corneal modifications including, but not limited to, corneal radius of curvature modifications shown in FIGS. 11 and 12 using various treatment patterns, including but not limited to two or more non-central treatments to induce various locations and amplitudes of corneal modifications for light redirections away from the fovea to two other retinal regions. Within each treatment pattern, FCXL is configured to produce treatment volumes that are at least 0.1 mm in diameter and that are located paracentrally (within the 3 to 6 mm optical zone) or peripherally (at >6 mm optical zone), with centration or decentration of the treatment pattern with respect to the pupil centroid or another centration reference.

In some exemplary embodiments, described herein, conventional corneal shape changing procedures and devices including, but not limited to, conductive keratoplasty (CK) and devices, including but not limited to radiofrequency emitting devices, are configured to produce corneal modifications in two or more spatially separated treatment areas of the cornea for retinal IDM. CK-produced corneal modifications include, but are not limited to, corneal radius of curvature modifications shown in FIGS. 11 and 12 using various treatment patterns, including but not limited to two or more non-central treatments to induce various locations and amplitudes of ROC modifications. Within each treatment pattern, CK is configured to produce treatment volumes that are at least 0.1 mm in diameter and that are located paracentrally (within the 3 to 6 mm optical zone) or peripherally (at >6 mm optical zone), with centration or decentration of the treatment pattern with respect to the pupil centroid or another centration reference.

Figure 15:
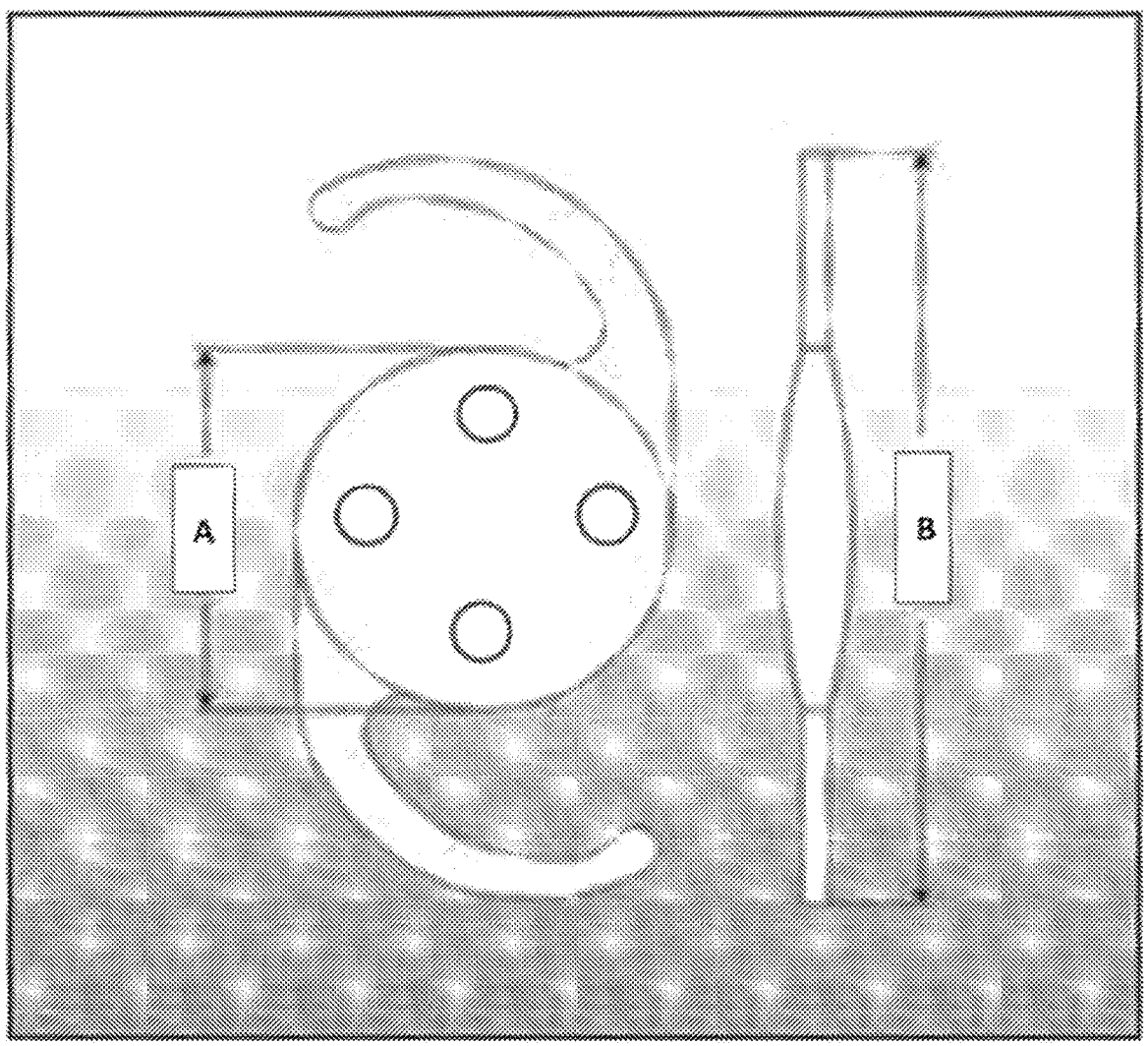
FIG. 15 is an IDM intraocular lens drawing with modifications in paracentral areas.

In some exemplary embodiments, described herein, retinal IDM is produced by insertion of an intraocular lens (IOL) and/or an intraocular lens accessory device (IOLAD) configured to modify the retinal IDM. IOLADs include, but are not limited to, light-steering structures including, but not limited to, refractive structures, diffractive structures or any combination thereof that act in combinations with IOLs to modify the retinal IDM. IOLs and IOLADs for phakic, aphakic or pseudophakic eyes include, but not limited to, IOLs and IOLADs positioned in the sulcus or capsular bag, anterior chambers IOLs and IOLADs, iris-fixated IOLs and IOLADs and transscleral-sutured IOLs and IOLADs. FIG. 15 illustrates an IOL modification suitable for retinal IDM that includes four paracentral regions with IOL modifications including, but not limited to, modifications of IOL radii of curvature, IOL indices of refraction, IOL diffraction, IOL scattering and any combination of IOL modifications thereof compared to the other regions of the IOL. In the case of IOL diffraction modifications, the exemplary modifications described herein are different from annular (ring-like patterns centered of the IOL center) modifications that are used in diffractive multifocal IOLs; for example, FIG. 15 illustrates four separate paracentral regions, one or more of which incorporate modifications of IOL diffraction. Additional IOL modifications include, but are not limited to, inclusion of light-steering structures (including, but not limited to, one or more reflectors, one or more optical fibers, one or more prisms or any combination of light-steering structures) within at least one paracentral region of the IOL. It is understood that two, three or more central, paracentral or peripheral regions that are spatially separated, with or without overlapping of the regions, can be used to produce IOL modifications in any or all of the regions for light redirections away from the fovea or another retinal fixation region to two or more retinal regions. It is also understood that IOL and IOLAD modifications can be configured in the IOL and IOLAD before and/or after IOL and IOLAD insertion; after insertion, a FS laser, another light source and/or electronic means can be used to produce IOL and IOLAD modifications in situ in order to produce adjustments to IOL and IOLAD radii of curvature, IOL and IOLAD indices of refraction, IOL and IOLAD light-steering structures, IOL and IOLAD diffraction, IOL and IOLAD scattering and any combination of adjustments thereof.

Figure 16:
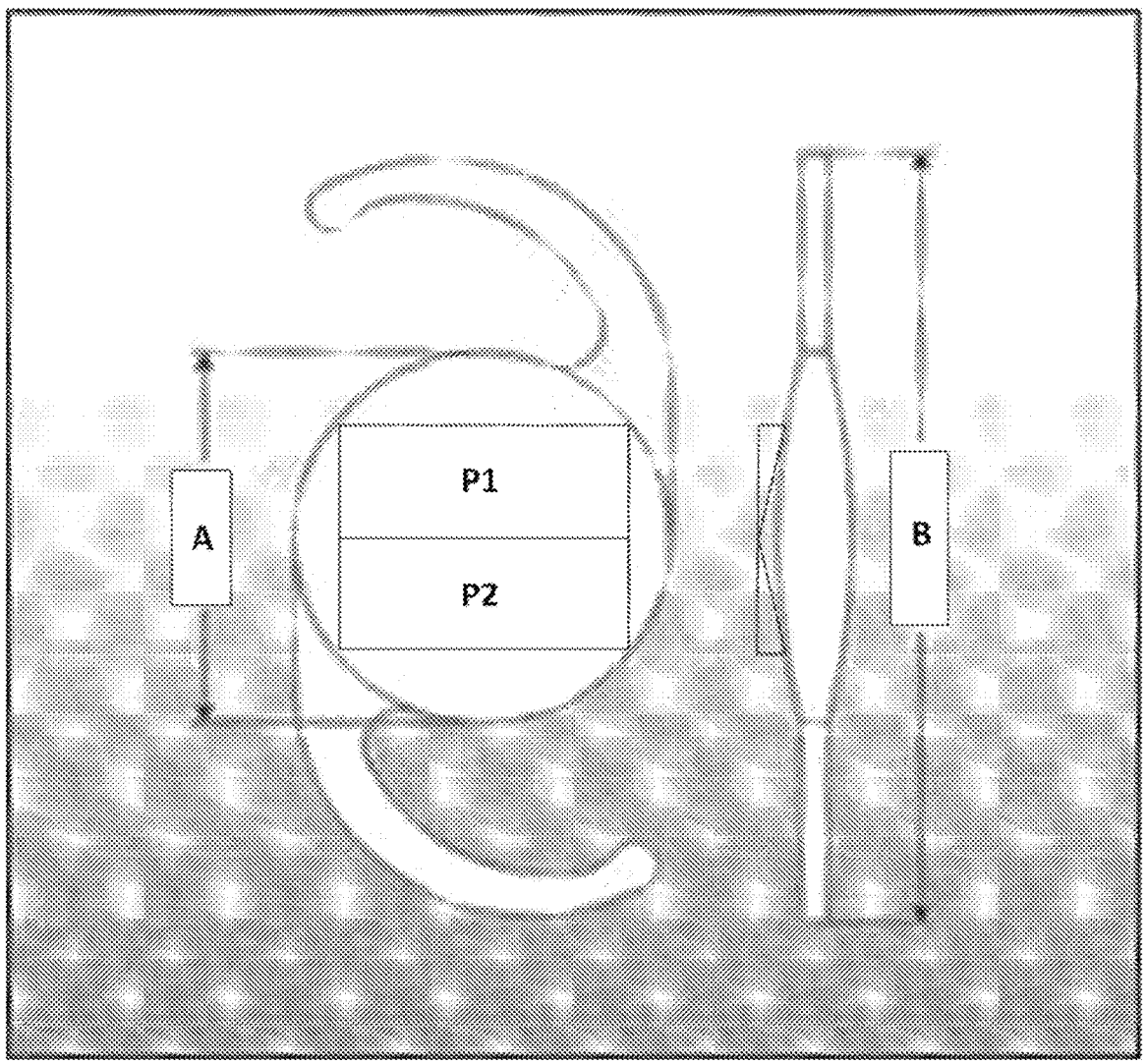
FIG. 16 is an IDM intraocular lens drawing with two prismatic sectors.

FIG. 16 illustrates an IOL modification suitable for retinal IDM that includes two or more prisms that direct irradiance onto functional areas of the retina. In addition, IOLs can be configured to include a combination of at least two central, paracentral or peripheral regions that are spatially separated, with or without overlapping of the regions to modify radii of curvature and/or indices in refraction in any or all of the regions and two or more prisms can be used for retinal IDM. For optimal retinal IDM in eyes with dysfunctional retinal areas, the changes of radii of curvature, changes of refractive indices, prismatic effects, or any combination thereof should produce as much retinal IDM as possible outside of dysfunctional retinal areas and inside functional retinal areas.

Figure 17:
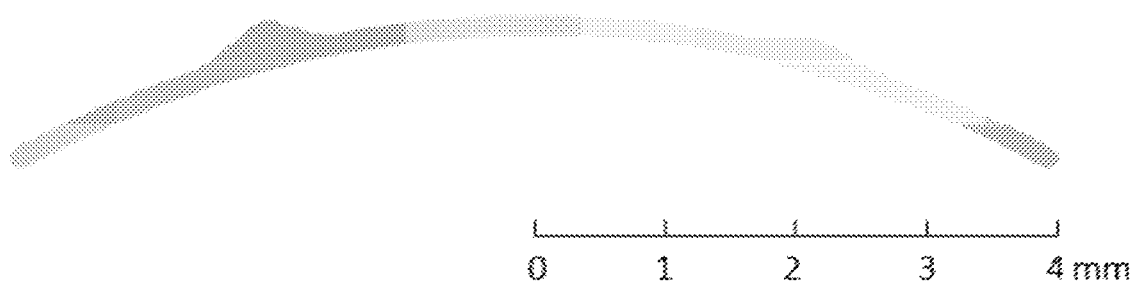
FIG. 17 is a schematic cross-section of an IDM contact lens with paracentral steepened regions.

Some exemplary embodiments, described herein, involve retinal IDM produced by spectacles, contact lenses or any combination thereof, with modifications including, but not limited to, modifications of radii of curvature, indices of refraction, diffraction, scattering and any combination of modifications thereof for light redirection away from the fovea or another retinal fixation region to at least two other retinal regions that are configured to produce retinal IDM. FIG. 17 shows a cross-section of a modified contact lens (CL; dimensions: 8 mm diameter, 0.2 mm thickness, 7.8 mm anterior and posterior radii of curvature) that includes paracentral steepened regions designed to redirect retinal irradiance from dysfunctional to functional retinal areas. CL dimensions may be different from those shown to include smaller or larger diameters, thicknesses and radii of curvature. Spectacle lenses can also be designed for retinal IDM. Spectacle lenses (SLs) and CLs may be fabricated from a single material or multiple materials. CLs may be corneal, scleral or a combination thereof. Modified SL and CL regions may have different or the same radii of curvature, different or the same refractive indices, different or the same diffraction, different or the same scattering or any combination thereof. Additional spectacle modifications include, but are not limited to, inclusion of light-steering structures including, but not limited to, at least one reflector and at least one optical fiber array within one or both spectacle lenses. There may be 1, 2 or more than 2 modified regions that are located centrally, paracentrally or peripherally within the CL diameter and/or within the SL shape. SLs and CLs may be used in one eye, both eyes or in any SL and CL combination. All SL and CL characteristics, dimensions and modifications are designed to direct light rays into an optimal retinal irradiance distribution for patient retinal IDM requirements. SLs and CLs can be configured statically or actively wherein static configuration is completed prior to incorporation within the ocular system and wherein active configuration is accomplished one or more times after incorporation within the optical system by means of adjustments including, but not limited to, electronic and/or photonic adjustments to corneal radii of curvature changes, indices of refraction changes, diffraction changes, scattering changes and any combination of changes thereof.

Some further exemplary embodiments, described herein involve the use of "trial" spectacle lenses (SLs), "trial" contact lenses (CLs), or any combination thereof for screening and/or customization purposes. In the screening application, "trial" lenses may help to determine whether patient eyes are capable of achieving vision and visual function improvements by retinal IDM devices and methods. In the customization application, "trial" lenses may be varied in characteristics to determine the optimal retinal IDM configuration. In both the screening and customization applications, it may be desirable for the patient to use the "trial" lenses for an extended period of days or weeks in order to obtain neuroadaptation benefits.

Figure 18:
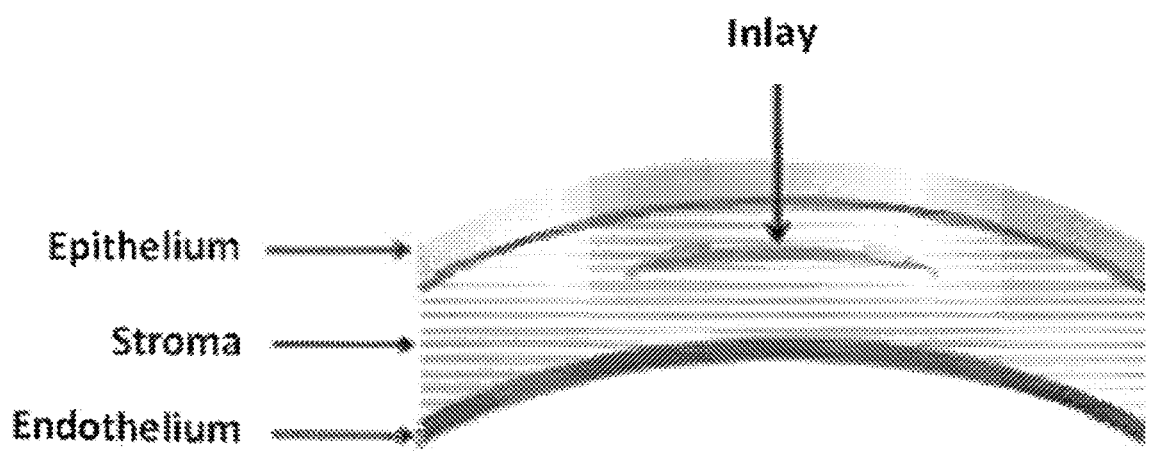
FIG. 18 is a schematic cross-section of an IDM corneal inlay implanted within a cornea.

Some exemplary embodiments, described herein, involve retinal IDM produced by corneal inlays (CIs). FIG. 18 shows a corneal inlay (CI) that is implanted into the cornea; the corneal segment shown is ca. 1.8 mm long with a central thickness of 0.55 mm but the corneal segment can have lengths extending to ca. 11 mm. Two lenses are shown on the inlay; these lenses can have the same or different modifications including, but not limited to, modifications of radii of curvature, indices of refraction, diffraction, scattering and any combination of modifications thereof. CI shapes can be circular or non-circular. The CI dimensions include, but are not limited to, lengths of 1 to 8 mm, widths of 1 to 8 mm, diameters of 3 to 8 mm and uniform or variable thicknesses in the range of 0.01 to 0.5 mm. There can be one, two, or more inlays, each of which can have 0, 1, 2, or more lenses. The inlay(s) can be located centrally as shown in FIG. 18 or can be located eccentrically. The inlay(s) can be implanted at depths from the anterior corneal surface including, but not limited to, depths of 0.05 to 0.5 mm. The lenses on each corneal inlay can be located on any position on each inlay. CIs are composed of materials including hydrogels, biocompatible materials and other materials known to those skilled in the art. Corneal inlays can be configured statically or actively wherein static configuration is completed prior to implantation within the cornea and wherein active configuration is accomplished one or more times after implantation within the cornea by means of adjustments including, but not limited to, electronic and/or photonic adjustments to corneal radii of curvature changes, indices of refraction changes, diffraction changes, scattering changes and any combination of changes thereof.

In some exemplary embodiments, described herein, retinal IDM devices and methods combine retinal IDM teachings with prior art retinal treatments, including pharmacological and/or retinal laser and/or radiation and/or stem cell transplantation and/or epigenetic and/or genetic and/or other therapy (hereafter other therapies) in order to improve treatment of macular degeneration and/or diabetic retinopathy and/or glaucoma and/or other neovascular and/or atrophic and/or inflammatory and/or genetic and/or nutritional and/or age-related retinal diseases (hereinafter "retinal diseases"). The exemplary retinal IDM devices and methods, described herein, overcome drawbacks and deficiencies of prior art by introducing different mechanisms of vision and/or retinal pathology and/or repair processes associated with retinal diseases. The exemplary retinal IDM devices and methods, described herein, overcome drawbacks and deficiencies of prior art therapies by synergistically combining them with retinal IDM with other therapies to improve visual and/or anatomic outcomes, which also improves patient compliance with prior art therapy. The combination therapy can be administered in the same patient visit or sequentially at different times. In some embodiments of combination therapy, retinal IDM treatment is delivered at one time, either before non-retinal IDM therapy or at some time following initiation of non-retinal IDM therapy. In some embodiments of combination therapy, more than one retinal IDM treatment is delivered at separate times, either before other therapies or at variable times following initiation of non-retinal IDM therapy.

In some exemplary embodiments, described herein, retinal IDM treatment is combined with other therapies for retinal diseases, including but not limited to retinal laser therapies, including but not limited to photobiomodulation, laser photocoagulation, laser photodynamic therapy, subthreshold micropulse laser therapy, glaucoma laser therapy, (including, but not limited to, laser trabeculoplasty and cyclophotocoagulation), glaucoma filtration surgery (including, but not limited to, trabeculectomy, microtrabeculectomy, internal or external tube shunt implantation, suprachoroidal shunt implantation), stem cell transplantation, and radiation therapy (including but not limited to focal intraocular strontium 90 beta radiation).

In some embodiments of the exemplary retinal IDM devices and methods described herein, retinal IDM treatment is combined with other therapies for retinal diseases including, but not limited to, genetic, epigenetic and optogenetic therapy.

In some exemplary embodiments, described herein, retinal IDM treatment is combined with pharmacological treatment of retinal diseases, including pharmacologic agents, including nutritional supplements, administered orally, topically to the cornea, via subconjunctival injection, via intravitreal injection, intraretinally, via implants and via iontophoresis.

In some exemplary embodiments, described herein, retinal IDM treatment is combined with antiangiogenesis drug therapy.

In some exemplary embodiments, described herein, retinal IDM provides a method of ameliorating or treating an ocular disorder, including but not limited to macular degeneration, choroidal neovascularization or diabetic retinopathy in a subject comprising treatment by retinal IDM in combination with administering a therapeutically effective amount of any vascular endothelial growth factor (VEGF) antagonist including, but not limited to ranibizumab, bevacizumab, brolucizumab and aflibercept, in combination with administering a therapeutically effective amount of any PDGF antagonist including, but not limited to, volociximab and P200, or in combination with any combination of the above drugs. As used herein, the term "ameliorating" or "treating" or "compensating for" means that the clinical signs and/or symptoms associated with an ocular disorder (e.g., macular degeneration) are lessened as result of the actions performed. The signs or symptoms to be monitored will be characteristic of the ocular disorder and will be well known to physicians skilled in the art, as will the methods for monitoring the signs, symptoms and conditions.

In some exemplary embodiments, described herein, retinal IDM provides a method of ameliorating or treating an ocular disorder, including but not limited to macular degeneration, choroidal neovascularization or diabetic retinopathy in a subject comprising treatment by retinal IDM in combination with administration of a therapeutically effective amount of vetalanib or pazopanib or any other tyrosine kinase inhibitor or any other inhibitor of phosphorylation of VEGF and PDGF receptors.

In some exemplary embodiments, described herein, retinal IDM provides a method of treating an ocular disease in a subject comprising treatment by retinal IDM in combination with administering a therapeutically effective amount of an inhibitor of VEGF activity.

In some exemplary embodiments, described herein, retinal IDM provides a method of treating or ameliorating an ocular disease in a subject comprising treatment by retinal IDM in combination with administering a therapeutically effective amount of an inhibitor of alpha5beta1 integrin activity.

In some exemplary embodiments, described herein, retinal IDM provides a method of treating or ameliorating an ocular disease, including but not limited to a neovascular ocular disease and/or wet macular degeneration, and/or diabetic retinopathy, in a subject comprising treatment by retinal IDM in combination with administering a therapeutically effective amount of an inhibitor of PDGF activity.

In some exemplary embodiments, described herein, retinal IDM provides a method of treating or ameliorating an ocular disease, including but not limited to a neovascular ocular disease and/or wet macular degeneration, and/or diabetic retinopathy, in a subject comprising treatment by retinal IDM in combination with administering a therapeutically effective amount of an inhibitor of tyrosine kinase activity.

In some exemplary embodiments, described herein, retinal IDM provides a method of treating or ameliorating an ocular disease, including but not limited to a neovascular ocular disease and/or wet macular degeneration, and/or diabetic retinopathy, in a subject comprising treatment by retinal IDM in combination with administering a therapeutically effective amount of an inhibitor of mTOR (sirolimus).

In some exemplary embodiments, described herein, retinal IDM provides a method of treating or ameliorating an ocular disease, including but not limited to a neovascular ocular disease and/or wet macular degeneration, and/or diabetic retinopathy, in a subject comprising treatment by retinal IDM in combination with administering a therapeutically effective amount of fluocinolone acetonide or any other anti-inflammatory agent, wherein the anti-inflammatory agent is delivered by intravitreal injection or delivered by an intraocular implant.

In some exemplary embodiments, described herein, retinal IDM provides a method of treating or ameliorating an ocular disease, including but not limited to geographic atrophy and/or dry macular degeneration, in a subject comprising treatment by retinal IDM in combination with administrating a therapeutically effective amount of an inhibitor of complement, including but not limited to complement 3 or 5, activity.

In some exemplary embodiments, described herein, retinal IDM provides a method of treating or ameliorating an ocular disease, including but not limited to geographic atrophy and/or dry macular degeneration in a subject comprising treatment by retinal IDM in combination with administering a therapeutically effective amount of avacincaptad pegol, LEG316, POT-4, eculizumab, JPE-1375, ARC1905 or any other complement inhibitor.

In some exemplary embodiments, described herein, retinal IDM provides a method of treating or ameliorating an ocular disease, including but not limited to geographic atrophy and/or dry macular degeneration in a subject comprising treatment by retinal IDM in combination with administering a therapeutically effective amount of doxycycline.

In some exemplary embodiments, described herein, retinal IDM provides a method of treating or ameliorating an ocular disease, including but not limited to geographic atrophy and/or dry macular degeneration in a subject comprising treatment by retinal IDM in combination with administering a therapeutically effective amount of glatiramer acetate or other T helper 2 inducer or immunomodulator.

In some exemplary embodiments, described herein, retinal IDM provides a method of treating or ameliorating an ocular disease, including but not limited to geographic atrophy and/or dry macular degeneration in a subject comprising treatment by retinal IDM in combination with administering a therapeutically effective amount of OT551, or any other downregulator of overexpression of the protein complex nuclear factor (NF)¬B or any other antioxidant, or combination of antioxidants, including but not limited to combinations of vitamin C, vitamin E, beta-carotene or lutein and zeaxanthin, and omega-3 fatty acids as in for, example, the Age-Related Eye Disease Study (AREDS) and AREDS 2 studies.

In some exemplary embodiments, described herein, retinal IDM provides a method of treating or ameliorating an ocular disease, including but not limited to geographic atrophy and/or dry macular degeneration in a subject comprising treatment by retinal IDM in combination with administering a therapeutically effective amount nicotinamide adenine dinucleotide (NAD) or any precursors of NAD, including but not limited nicotinamide riboside or nicotinamide mononucleotide.

In some exemplary embodiments, described herein, retinal IDM provides a method of treating or ameliorating an ocular disease, including but not limited to geographic atrophy and/or dry macular degeneration in a subject comprising treatment by retinal IDM in combination with administering a therapeutically effective amount of a trophic factor including, but not limited to, pigment epithelium-derived factor (PEDF), fibroblast growth factors (FGFs) and lens epithelium-derived growth factor (LEDGF).

In some exemplary embodiments, described herein, retinal IDM provides a method of treating or ameliorating an ocular disease, including but not limited to geographic atrophy and/or dry macular degeneration in a subject comprising treatment by retinal IDM in combination with administering a therapeutically effective amount of ciliary neurotrophic factor (CNTF) or any other neurotrophic factors or any other inhibitors of photoreceptor apoptosis.

In some exemplary embodiments, described herein, retinal IDM provides a method of treating or ameliorating an ocular disease, including but not limited to geographic atrophy and/or dry macular degeneration in a subject comprising treatment by retinal IDM in combination with administering a therapeutically effective amount of a neuroprotective agent, including but not limited to brimodinine.

In some exemplary embodiments, described herein, retinal IDM provides a method of treating or ameliorating an ocular disease, including but not limited to geographic atrophy and/or dry macular degeneration in a subject comprising treatment by retinal IDM in combination with administering a therapeutically effective amount of a Fas inhibitor or other agent designed to protect retinal cells from cell death.

In some exemplary embodiments, described herein, retinal IDM provides a method of treating or ameliorating an ocular disease, including but not limited to geographic atrophy and/or dry macular degeneration and/or neovascular macular degeneration and/or glaucoma in a subject comprising treatment by retinal IDM in combination with administering a therapeutically effective amount of a statin, including but not limited to atorvastin, lovastation, rosuvastatin, fluvastatin, or simvastatin.

In some exemplary embodiments, described herein, retinal IDM provides a method of treating or ameliorating an ocular disease, including but not limited to glaucoma or ocular hypertension in a subject comprising treatment by retinal IDM in combination with administering a therapeutically effective amount of an intraocular pressure (IOP)—lowering agent, including but not limited to a miotic, an alpha or alpha/beta adrenergic agonist, a beta-blocker, a Ca2+ channel blocker, a carbonic anhydrase inhibitor, chlolinesterase inhibitor, a prostaglandin agonist, a prostaglandin, a prostamide, a cannabinoid, and combinations thereof.

In some exemplary embodiments, described herein, retinal IDM provides a method of treating or ameliorating an ocular disease, including but not limited to glaucoma in a subject comprising treatment by retinal IDM in combination with administering a therapeutically effective amount of a pharmacological agent decreasing retinal ganglion cell dysfunction and/or pathology, related to ischemia or excitotoxicity.

In some exemplary embodiments, described herein, retinal IDM provides a method of treating or ameliorating an ocular disease, including but not limited to glaucoma in a subject comprising treatment by retinal IDM in combination with administering a therapeutically effective amount of a pharmacological agent decreasing excessive excitatory amino acid (EAA) stimulation (EAA permits the bipolar and amacrine cells to communicate with the ganglion cell), including but not limited to a glutamate antagonist and/or any combination of a glutamate antagonist and at least one IOL-lowering agent.

In some exemplary embodiments, described herein, retinal IDM provides a method of treating or ameliorating an ocular disease, including but not limited to glaucoma in a subject comprising treatment by retinal IDM in combination with administering a therapeutically effective amount of a pharmacological agent providing neuroprotection and/or neuroregeneration of retinal ganglion cells, including but not limited to a rho-kinase (ROCK) inhibitor or an adenosine receptor agonist.

A retinal location used by an eye to attempt fixation on a visual target is known as a preferred retinal locus of fixation (e.g., a "PRL"). The PRL of an eye can be determined by fixation, e.g. an eye fixating on a light. The PRL also can be determined by perimetry or microperimetry. For example, the PRL may correspond to the barycenter of the cloud of fixation points on microperimetry. In some instances, the retinal location of the PRL may be described relative to the center of the foveola of the eye, or relative to an estimated center of the foveola, and may be specified in terms of polar coordinates $r, \theta$ or $r', \theta$ in which r is the distance in mm units or r' is the distance in terms of retinal eccentricity in units of degrees, and $\theta$ is the angular coordinate.

The PRL in a normal-sighted eye is located within the fovea, but not always the foveal center. Further, in a normal-sighted eye, the PRL usually is located within the foveolar region. The foveola covers only ≈1° of visual angle, which corresponds to less than 0.1% of the visual field In some instances, the PRL may be displaced from the location of highest foveal cone density by an average of about 10 arc minutes in a normal-sighted eye. Further, in some instances, a correlation may not exist between a magnitude of offset from the PRL and corresponding foveal specialization measurements including, but not limited to, pit volume, FAZ area, and peak cone density.

The PRL is located within the fovea or eccentric to the fovea in an eye with central retinal damage or loss. The visual system includes the elements of the eye and the brain that capture and process visual information, as illustrated in FIGS. 3 and 4. Spatial and temporal characteristics of neural processing within the visual system are factors influencing the location of the preferred retinal locus of fixation. Further, the smallest fixational eye movements are known to have an amplitude between about 0.01° to about 0.1°.

In some examples, described herein, methods and apparatus may cause a redirection of environmental light away from a PRL of an eye to multiple retinal locations that are not the PRL. One or more of these exemplary methods and apparatus may cause a safe and effective redirection of environmental light from within an eye's field of view away from the PRL of the eye and toward multiple retinal locations that are not the PRL. In some instances, one or more of these exemplary methods and apparatus may cause a redirection that shifts the barycenter of the cloud of fixation points of the eye by at least 0.01°, e.g., as measured by microperimetry. In some instances, one or more of these exemplary methods and apparatus may cause a redirection that shifts the barycenter of the cloud of fixation points of the eye by at least 0.1°, e.g., as measured by microperimetry.

Further, in some instances, one or more of the exemplary methods and apparatus described herein may cause a redirection of light away from a PRL of an eye to multiple retinal locations that are not the PRL, and may modify visual search, retinal sampling and stimulation of retinal and brain cells to enhance neural integration and perception of visual information in the field of view and facilitate ongoing neuroadaptation, e.g. to "reboot" a visual system, which includes the eye and the brain.

One or more of the exemplary methods and apparatus described herein may also reboot the visual system to improve and/or restore vision safely and effectively. Vision may include, but is not limited to, discrimination of spatial detail, visual acuity (including uncorrected and/or best spectacle-corrected visual acuity for distance, intermediate and/or near visual acuity), hyperacuity, stereoacuity, vernier acuity, contrast sensitivity, depth of focus, color vision, peripheral vision, night vision, face recognition, light adaptation, dark adaptation, visual fields and/or vision-related quality of life, or any combination thereof.

Further, one or more of the exemplary methods and apparatus may reboot the visual system. Rebooting of the visual system may include, but is not limited to, any or any combination of the following: (i) improving neural computation with integration of additional and/or more correctly coded retinal information from macular and peripheral retinal cells—including, but not limited to, photoreceptors, bipolar cells, amacrine cells, horizontal cells, Müller glial cells, ganglion cells or any combination of retinal cells—to enable processing of more complete stimulus patterns; (ii) improving functioning of retinal circuitry, including connectivity functions in visual processing involving photoreceptors, ganglion cells, amacrine cells, bipolar cells, horizontal cells, and Müller cells or any combination thereof; and/or (iii) triggering processes of neural adaptation, including but not limited to, use of alternate, latent, and/or new visual pathways in the retina and brain including, but not limited to: rerouting of visual information encoded by peripheral areas of the retina to neurons at high levels of the visual cortex with receptive fields normally tasked with encoding objects at the center-of-gaze, permitting beneficial alteration of crowding properties with reduced critical spacing in those peripheral areas; changing the destination of fixational eye movements; beneficially changing the amplitude and/or speed of eye movements; beneficially changing the interaction of the saccadic corollary discharge circuit with the rest of the visual cortex; and/or producing more effective and spontaneous searching to achieve more effective integration of a greater amount of more correct visual information by searching mechanisms including, but not limited to, spontaneously producing motor learning in the eye movement strategy to both collect information from a greater area of the field of view and use more retinal cells for visual perception of the field of view. Additionally, one or more of the exemplary methods and apparatus described herein, which cause redirection of light away from the PRL of an eye to multiple retinal locations that are not the PRL enhance beneficial homeostatic plasticity mechanisms that promote cellular signaling and visual function.

In some instances, one or more of the exemplary methods and apparatus described herein may cause a rebooting of the visual system of an eye by reducing exposure of environmental light from within the field of view of an eye to the PRL. One or more of the exemplary methods and apparatus described herein may cause a rebooting of the visual system of an eye by reducing exposure of environmental light from within a field of view of an eye to the PRL by at least 10%, i.e. by any amount or cumulative amount equal to or greater than 10%. Exposure of environmental light may be reduced at the PRL in order to force the visual system, which includes the eye and the brain, to find and use alternate, latent and/or new visual pathways arising from retinal locations other than the PRL.

One or more of the exemplary methods and apparatus described herein may cause a rebooting of the visual system of an eye by weighting exposure of environmental light from within the field of view of an eye to reduce exposure to a PRL of the eye by at least 10% for a determinable interval. The interval may be defined in milliseconds, seconds, minutes, hours, days, weeks, months, and/or years and may be determined at any time prior to or after initial utilization. The determinable interval may be determined by factors including, but not limited to, individual patient response, a type of disease or disorder of the eye, a progression or regression of the disease or disorder of the eye, pre-treatment visual data, and/or post-treatment visual data. One or more of the exemplary methods and apparatus described herein may cause a weighting of an exposure of environmental light from within a field of view of an eye to reduce exposure to a PRL of the eye by at least 10% for a determinable interval. In some instances, the environmental light within the field of view may be exposed to the retina at a determinable rate up to 50 kilohertz, which may cause a rebooting of processing of environmental light from within the field of view of the eye.

In some instances, the determinable rate, which may be any rate no greater than 50 kilohertz, may be determined by factors including, but not limited to, individual patient response, type of disease or disorder of the eye, progression or regression of the disease or disorder of the eye, pre-treatment visual data and/or post-treatment visual data. Some of the exemplary methods and apparatus described herein may enable an exposure rate at any rate up to 50 kilohertz to enable modulation of light capture from within the entire field of view by retinal photoreceptors to cause altered temporal neural integration within the eye and brain before perception. One or more of the exemplary methods and apparatus described herein may cause altered temporal neural integration within the eye and brain to enable stable and seamless perception after neural processing while causing reduced exposure of environmental light from within the field of view to a PRL of an eye by at least 10% for a determinable interval. Further, some of the exemplary methods and apparatus described herein may cause a weighting of an exposure of environmental light from within a field of view of an eye to reduce exposure to a PRL of the eye by at least 10%, by at least 25%, by at least 50%, by at least 75%, by at least 90%, or by any amount, for a determinable interval to cause a rebooting of processing of environmental light from within the field of view of the eye. Some exemplary embodiments cause weighting of exposure of environmental light from within a field of view of an eye to reduce exposure to a PRL of the eye by at least 10% for a determinable interval to cause an improvement of vision or a restoration of vision.

Some of the exemplary methods and apparatus described herein may be configured to cause a weighting of an exposure of environmental light from within a field of view of an eye to increase exposure to more than one retinal location that it not the preferred retinal locus of centration of the eye by at least 10% for a determinable interval to cause an improvement of vision or a restoration of vision. One or more of the exemplary methods and apparatus described herein may also cause a weighting of an exposure of environmental light from within a field of view of an eye to increase exposure to a plurality of retinal locations that are not the PRL at least 10% more than at the PRL for a determinable interval to cause an improvement of vision or a restoration of vision. Some of the exemplary methods and apparatus described herein may also enable an exposure rate at any rate up to 50 kilohertz to enable modulation of light capture from within an entire field of view by retinal photoreceptors to enable stable and seamless perception after neural processing while causing exposure of environmental light from within the field of view to a PRL of an eye to be increased to a plurality of retinal locations that are not the PRL at least 10% more than at the PRL for a determinable interval.

Further, some of the exemplary methods and apparatus described herein may cause a rebooting of a visual system of an eye by causing a defocusing of environmental light from within a field of view of the eye at a PRL of the eye. Environmental light from within the field of view of the eye may be defocused at the PRL in order to force the visual system, which includes the eye and the brain, to find and use alternate, latent and/or new visual pathways arising from retinal locations other than the PRL. Some of the exemplary methods and apparatus described herein may cause a rebooting of a visual system, which includes an eye and a brain, by causing a focusing at numerous and non-contiguous retinal locations that are not the PRL of the eye. Further, one or more of the exemplary methods and apparatus described herein may also cause a rebooting of a visual system of an eye by causing a defocusing of environmental light from within a field of view of the eye at a PRL of the eye and/or a focusing at a plurality of non-contiguous retinal locations that are not the PRL of the eye, to cause an improvement of vision and/or a restoration of vision in an eye with an impairment and/or loss of central and/or peripheral vision.

Some of the exemplary methods and apparatus described herein may improve vision in an eye with an impairment or loss of central vision by defocusing for determinable distances environmental light from within a field of view of the eye at the PRL. Some of the exemplary methods and apparatus described herein may defocus at the PRL an image(s) of objects located within the field of view of an eye at certain or varying distances from the eye. Further, one or more of the exemplary methods and apparatus described herein may cause a defocusing of environmental light from within a field of view of an eye at a PRL without requiring determination of optical errors or image quality at the PRL. Some of the exemplary methods and apparatus described herein may focus at numerous and non-contiguous retinal locations that are not the PRL an image(s) of objects located within the field of view of an eye at certain or varying distances from the eye. Some of the exemplary methods and apparatus described herein may cause a rebooting of a visual system of an eye by causing a focusing at multiple and non-contiguous retinal locations that are not the PRL of the eye without requiring determination of optical errors or image quality at the non-contiguous retinal locations that are not the PRL.

Some of the exemplary methods and apparatus described herein may also cause a rebooting of a visual system of an eye by causing a focusing at numerous and non-contiguous retinal locations that are not the PRL of the eye. For example, these exemplary methods and apparatus may achieve a random or non-random focus at the numerous and non-contiguous retinal locations by modifying a range of optical and/or mechanical parameters.

Some of the exemplary methods and apparatus described herein may cause redirection of light away from the PRL of an eye to multiple retinal locations that are not the PRL to reboot the visual system immediately upon redirection of the light. For such an immediate rebooting, some of the exemplary methods and apparatus described herein may cause transient redirections of light and/or decreasing numbers of redirections and/or decreasing dimensions of redirections over time to increase efficacy and safety. Some of the exemplary methods and apparatus described herein may include transformable components and/or cause transformable alteration to the eye or structures inserted within an eye to increase the safety and efficacy of redirecting light away from a PRL of the eye to multiple retinal locations that are not the PRL. Some of the exemplary methods and apparatus described herein may cause increasing or decreasing numbers of redirections and/or increasing or decreasing dimensions of redirections and/or changes in retinal portions to which the environmental light is redirected to improve the rebooting of a visual system continuously or intermittently or repeatedly upon redirection of the light for any determinable interval of time for initial and/or repeat utilization. Some of the exemplary methods and apparatus described herein may cause redirection of light away from a PRL of an eye to multiple non-contiguous retinal locations that are not the PRL immediately and/or continuously and/or intermittently and/or repeatedly to reboot the visual system immediately and/or continuously and/or intermittently and/or repeatedly upon redirection of the light for any determinable interval for initial and/or repeat utilization. The determinable interval for initial and/or repeat utilization may be determined by factors including, but not limited to, individual patient response, type of disease or disorder of the eye, progression or regression of the disease or disorder of the eye, pre-treatment visual data and/or post-treatment visual data. Some of the exemplary methods described herein may be reversible to improve safety and/or efficacy and/or to permit another redirection at a determinable interval and/or to facilitate other therapy. Some of the exemplary methods and apparatus described herein may cause reversible redirection of light and/or reversible alterations to ocular tissue and/or reversible alteration of at least one component of the apparatus.

Some of the exemplary methods and apparatus described herein may cause redirection of light away from a PRL of an eye to multiple retinal locations that are disposed within normal portions of a retina, damaged portions of a retina, diseased portions of a retina, genetically altered portions a retina, epigenetically altered portions of a retina, neuroregeneratively altered portions of a retina, or portions of a retina that includes at least one of a retinal transplant, an implanted retinal cell (including, but not limited to retinal epithelial cells, photoreceptors, ganglion cells, retinal progenitor cells), an implanted stem cell, or an implanted prosthesis.

Some of the exemplary methods and apparatus described herein may cause weighting of exposure of environmental light from within a field of view of an eye to reduce exposure to a PRL of the eye by at least 10% for a determinable interval. In some instances, the environmental light within the field of view may be exposed to the retina at a determinable rate up to 50 kilohertz, and the environmental light within the field of view may be exposed to a genetically altered portion of the retina, an epigenetically altered portion of the retina, a neuroregeneratively altered portion of the retina, or a portion of the retina that includes at least one of a retinal transplant, an implanted retinal cell, an implanted stem cell, or an implanted prosthesis.

Some of the exemplary methods and apparatus described herein may improve vision in an eye with an impairment of central vision and cause a defocusing of environmental light from within a field of view of the eye at a PRL of the eye and a focusing of environmental light within at least one of a genetically altered portion of a retina, an epigenetically altered portion of a retina, or a neuroregeneratively altered portion of a retina. Some of the exemplary methods and apparatus described herein may cause a defocusing of environmental light from within a field of view of an eye at a PRL of the eye and a focusing of environmental light within a plurality of portions of a retina that includes at least one of a retinal transplant, an implanted retinal cell, an implanted stem cell, or an implanted prosthesis.

Some of the exemplary apparatus described herein may include transformable components, or may be configured to cause transformable modifications of an eye structure or structures placed within an eye to cause transient or reversible or repeatable redirections of environmental light away from a PRL to multiple retinal locations that are not the PRL in the eye with a progressive retinal disease or degeneration. Some of the exemplary apparatus described herein may also include transformable components, or may be configured to, cause transformable modifications of an eye structure or structures placed within an eye to cause weighting of exposure of environmental light from within the field of view of the eye to reduce exposure to a PRL of the eye by at least 10% for a determinable interval in an eye with a progressive retinal disease or degeneration. Some of the exemplary apparatus described herein may also include transformable components, or may be configured to cause transformable modifications of an eye structure or structures placed within an eye to cause a defocusing of environmental light from within a field of view of the eye at a PRL of the eye and/or a focusing at numerous and non-contiguous retinal locations that are not the PRL in an eye with a progressive retinal disease or degeneration. Some of these exemplary apparatus and methods may permit, after progressive damage to photoreceptors, ganglion cells or other retinal tissue, repeat rebooting of the visual system. Some of these exemplary apparatus and methods may also permit safe and effective rebooting of the visual system to improve vision and/or to enhance retinal repair and/or myelination.

Some of the exemplary methods and apparatus described herein may facilitate a safe and effective increase of an activity in multiple retinal cells and/or stimulate metabolic processes and/or repair mechanisms in viable retinal cells. Further, some of the exemplary methods and apparatus described herein may facilitate a safe and effective reduction in cumulative focal light exposure or cumulative oxidative stress in individual retinal cells in some portions of the retina and/or delay progression of macular and/or peripheral retinal degeneration in inherited and acquired diseases and disorders. For example, unlike currently proposed and investigated, but not yet approved, treatments for delaying progression of macular degeneration, such as selective thermolysis, photobiomodulation, or intravitreal photovoltaic stimulation, that could damage and/or overstimulate retinal cells and/or cause deleterious amounts of complement activation and/or cause premature retinal atrophy, some exemplary methods and apparatus described herein delay macular and/or peripheral degeneration without overstimulation and/or damage to retinal tissue.

Some of the exemplary apparatus described herein may include transformable components or may be configured to cause transformable alterations of an eye structure or structures placed within an eye to cause transient or reversible redirections of environmental light away from a PRL to multiple retinal locations that are not the PRL in genetically or epigenetically altered portions. Some of the exemplary apparatus described herein may cause weighting of exposure of environmental light from within the field of view of an eye in genetically altered portions of a retina or in epigenetically altered portions of the retina. One or more of the exemplary apparatus and methods described herein may permit repeat rebooting of a visual system of an eye by a redirection of environmental light away from a PRL to multiple other retinal locations in genetically altered portions, or by weighting exposure of environmental light or by decreasing focusing at the PRL while focusing at genetically altered portions to increase the number of retinal locations that achieve adequate tissue transduction and trans-gene expression and that can contribute to neural integration and perception.

Some of the exemplary apparatus described herein may include transformable components or may be configured to cause transformable modifications of an eye structure or structures placed within an eye to cause transient or reversible or repeatable redirections of environmental light away from a PRL to multiple retinal locations that are not the PRL in a retina that contains a retinal transplant, implanted retinal cells, an implanted stem cells, or an implanted prosthesis. Some of the exemplary apparatus described herein may cause a weighting of an exposure of environmental light from within a field of view of an eye to portions of a retina that contains a retinal transplant, implanted retinal cells, an implanted stem cells, or an implanted prosthesis. Current diagnostic techniques often fail to provide a reliable assessment of the visual functioning of individual retinal cells or areas and/or prosthetics. Certain of the exemplary apparatus and methods described herein may permit repeatable rebooting of the visual system safely and effectively in a retina that contains a retinal transplant, implanted retinal cells, an implanted stem cells or an implanted prosthesis to enable more retinal areas at which environmental light is focused or to which the light has been redirected or exposed with weighting to contribute to neural integration and perception.

Some of the exemplary methods and apparatus described herein may reboot a visual system safely and effectively in conjunction with natural visual processing. Some of the exemplary methods and apparatus described herein may reboot the visual system without requiring perceptual or oculomotor training. Some of the exemplary methods and apparatus described herein may also reboot the visual apparatus without damage to retinal architecture or natural visual processing mechanisms. As an example of these advantages, and unlike some currently investigated (but not yet approved) strategies for visual loss, such as retinal prosthetic implantation that irreversibly destroys retinal architecture and natural visual processing, some exemplary methods and apparatus described herein do not damage or replace any ocular tissue and do not destroy natural visual processing. As another example of some advantages, and unlike some currently investigated (but not yet approved) strategies for central visual loss, such as electronic retinal remapping that replaces real visual information from the field of view with simulated and distorted information in paracentral areas of the field of view and does not transmit all images within the field of view, some exemplary methods and devices described herein may transmit the actual and full field or view and do not distort visual information within the field of view.

Some of the exemplary methods and apparatus described herein may facilitate a redirection of environmental light away from a PRL of an eye to multiple retinal locations that are not the PRL optically, mechanically, or both optically and mechanically. Some of the exemplary methods and apparatus described herein may facilitate an easy, safe, effective, efficient, and/or timely optical, mechanical, or optomechanical weighting of an exposure of environmental light from within a field of view of an eye to reduce exposure to a PRL of the eye by at least 10% for a determinable interval. In some instances, the environmental light within the field of view may be exposed to the retina at a determinable rate up to 50 kilohertz, the determinable interval may include milliseconds, seconds, minutes, hours, days, weeks, or years, and the exemplary methods and apparatus described herein may determine the determinable interval based on a user's visual response, apparatus configuration, an ocular disease/disorder, and/or a progression of a visual impairment, a visual loss, and/or an ocular disease/disorder. Some of the exemplary apparatus described herein may include optical components and/or mechanical components.

Some of the exemplary methods described herein may be implemented by, or may utilize, an apparatus, and may cause a defocusing of environmental light from within a field of view of an eye at a PRL and may modify an optical property or behavior in a plurality of portions outside an optical zone of a structure positioned anterior to a retina. Some of the exemplary methods described herein may be implemented by, or may utilize, an apparatus, and may cause a defocusing of environmental light from within a field of view of an eye at a PRL of the eye, and may modify a mechanical property or behavior in a plurality of portions outside an optical zone of a structure positioned anterior to a retina. Some of these exemplary methods may improve and/or restore vision in an eye with an impairment and/or loss of central and/or peripheral vision.

Some of the exemplary methods described herein may be implemented by, or may utilize, an apparatus positioned anterior to a retina of an eye. In some instances, the positioning of the apparatus "anterior to a retina" may include a positioning of the apparatus extraocularly, a positioning of the apparatus on the surface of the eye, a positioning of the apparatus intracorneally, and/or a positioning of the apparatus intraocularly. Some of the exemplary apparatus described herein may include glasses and other eye-mountable devices, contact lenses, corneal inlays, intraocular lenses (IOLs), and other intraocular devices.

Some of the exemplary apparatus described herein may be configured to produce programmable transient, reversible, and/or repeatable redirection of environmental light away from a PRL of an eye to a plurality of retinal locations that are not the PRL. In some instances, the exemplary apparatus may include a control unit (e.g., a controller) coupled to a source of electrical energy (e.g., a power source), and the control unit may include one or more processors that, upon execution of software instructions (e.g., locally stored by the control unit or apparatus within a tangible, non-transitory memory or included within a received signal), cause the exemplary apparatus to produce the programmable transient, reversible, and/or repeatable redirection of environmental light.

Further, some of the exemplary methods or apparatus described herein may cause a transient, reversible, and/or repeatable redirection of environmental light away from a PRL of an eye to multiple retinal locations that are not the PRL by guiding light away from the PRL to a plurality of retinal locations mechanically, electromechanically, optically, or optomechanically. In addition, one or more of the exemplary apparatus described herein may be configured to redirect environmental light away from a PRL of an eye to multiple retinal areas that are not the PRL, and may include one or more clear components disposed anterior to a retina of an eye and coupled to controller. As described herein, the controller may be coupled to a power source, and the controller may be configured to generate and route control signals to the clear components (e.g., based on software instructions executed by one or more processors, etc.), which may cause the clear components to redirect environmental light away from the PRL of an eye to a plurality of retinal locations that are not the PRL.

In some examples, one of more of these exemplary apparatus may include one or more clear components, one or more optomechanical components disposed on a surface of, or within, the one or more clear components, and a controller coupled electrically to the one or more optomechanical components via an electrically conductive layer. As described herein, the controller may be configured to generate and route control signals (e.g., based on software instructions executed by one or more processors, etc.) to the one or more optomechanical components, and upon receipt of the control signals, the one or more optomechanical components may cause redirection of environmental light away from the PRL of the eye to a plurality of retinal locations that are not the PRL Some of the exemplary apparatus described herein, which may be configured to redirect environmental light away from a PRL of an eye to multiple retinal locations that are not the PRL, may include one or more clear components disposed anterior to a retina of the eye, and a controller coupled to the one or more clear components via a conductive component. The controller may perform any of the exemplary operations described herein to generate and route control signals via the conductive component to the clear components. For example, the exemplary apparatus may include one or more components disposed on a surface of, or within, the one or more clear components, and upon receipt of the control signals, the one or more components cause the redirection of environmental light away from the PRL to the plurality of retinal locations that are not the PRL. The one or more components may, in some examples, include refractive components, diffractive components, or a combination of diffractive and refractive components, and the control signals may cause a modification of the refractive components, the diffractive components, or the combination of diffractive and refractive components to redirect environmental light away from the PRL of the eye to the plurality of retinal locations that are not the PRL. Further, one or more of the exemplary apparatus described herein may also include at least one lens for correcting a refractive error of an eye.

Some of the exemplary apparatus described herein may include at least one control unit (e.g., a controller), and may be configured (e.g., based on control signals generated by the controller) to produce programmable weighting of exposure of environmental light from within a field of view of an eye to reduce exposure to a PRL of the eye by at least 10% for a determinable interval. Some of the exemplary apparatus described herein may include at least one control unit (e.g., a controller), and may be configured (e.g., based on control signals generated by the controller) to produce programmable weighting of exposure of environmental light from within a field of view of an eye to reduce exposure to a PRL by at least 10% or to increase exposure to retinal locations that are not the PRL more than 10% than at the PRL for a determinable interval at a determinable rate from 0 to 50 kilohertz. Some of the exemplary methods and apparatus described herein may cause transient, reversible, and/or repeatable redirection of environmental light away from a PRL of an eye to multiple retinal locations that are not the PRL by directing light away from the PRL to a plurality of retinal locations mechanically, electromechanically, optically, and/or optomechanically. Further, some of the exemplary methods and apparatus may include, or may perform, mechanical, electromechanical, optical, and/or optomechanical operations that generate a weighting of an exposure of environmental light from within a field of view of an eye to reduce the exposure to a PRL by at least 10%, or to increase the exposure to a plurality of retinal locations that are not the PRL more than 10% than at the PRL, for a determinable interval of time at a determinable rate from 0 to 50 kilohertz.

Figure 19:
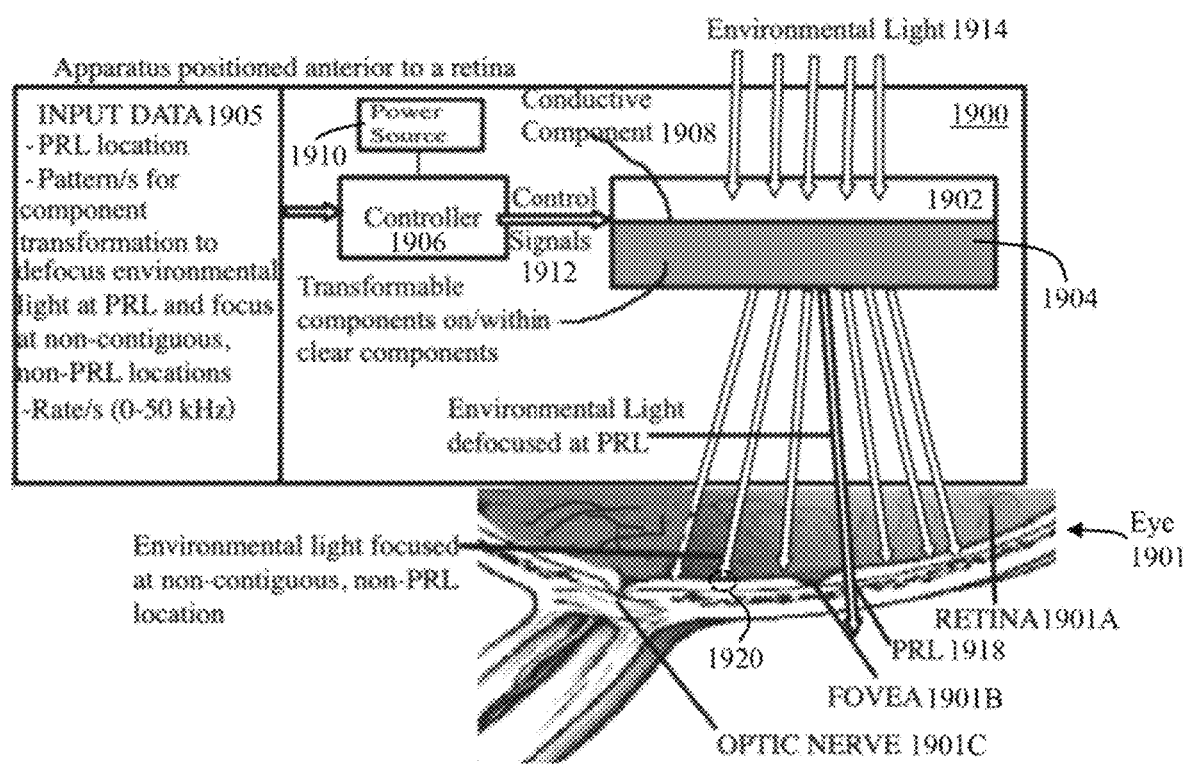
FIG. 19 is a diagram of an exemplary apparatus for improving or restoring vision, in accordance with some exemplary embodiments.

FIG. 19 illustrates an exemplary apparatus 1900 for improving or restoring vision. In some examples, apparatus 1900 may include one or more clear components 1902 positioned anterior to a retina 1901A of an eye 1901 (which also includes a fovea 1901B and an optic nerve 1901C), one or more transformable components 1904 disposed on a surface of, or within, one or more of clear components 1902, and a controller 1906 coupled to transformable components 1904 via a conductive component 1908. Further, controller 1906 may also be coupled to a source of electrical energy, such as power source 1910, and may be configured to generate and route control signals 1912 to transformable components 1904 (e.g., based on electrical energy received from power source 1910).

As illustrated in FIG. 19, controller 1906 may receive one or more elements of input data 1905, and may be configured to process the received elements of input data 1905 and generate and route control signals 1912 to transformable components 1904. In some examples, the elements of input data 1905 may include, but are not limited to, a location of a PRL 1918 of eye 1901, information that characterizes a pattern(s) of component transformation to direct environmental light to cause a defocusing for determinable distances of environmental light at PRL 1918, and a determinable rate (e.g., ranging from zero to 50 kHz). In some examples, controller 1906 may include one or more processors that, upon execution of software instructions (e.g., locally stored by the controller within a tangible, non-transitory memory or included within a received signal), causes the controller to generate and transmit control signals 1912 to transformable components 1904.

In some examples, and upon receipt of control signals 1912, one or more of transformable components 1904 may reorganize at least one pattern of direction of environmental light 1914 to retina 1901A at a determinable rate up to 50 kilohertz. The at least one pattern of direction of environmental light may cause a rebooting of processing of environmental light 1914 by the visual system of the eye 1901 The at least one pattern may, for example, cause a defocusing at a PRL of the eye 1901 (e.g., PRL 1918 of FIG. 19) and/or a focusing at numerous and non-contiguous retinal locations that are not the PRL, such as location 1920. Further, in some examples, the at least one pattern does not generate an aperture.

In some instances, the signal(s) for generating a pattern(s) causing focusing or defocusing of the environmental light may be continued for any number of milliseconds, seconds, minutes, hours, days, months, or years (e.g., by controller 1906 using any of the exemplary processes described herein) to cause and/or maintain and/or repeat a rebooting of processing of environmental light 1914 by the visual system. Further, although not illustrated in FIG. 19, some of the exemplary apparatus described herein, such as apparatus 1900, may include at least one lens, such as, but not limited to, at least one lens for correction of at least one refractive error.

In some instances, transformable components 1904 may include at least one of an optically active component, an optomechanical component, an electromechanical component, or a projection component. Further, some of the exemplary apparatus described herein also may include at least one component with at least one of an isotropic property and an isotropic behavior. For example, at least one of transformable components 1904 may include a transformable component with at least one of an isotropic property and an isotropic behavior. In some instances, and responsive to control signals 1912, transformable components 1904 may reorganize at least one pattern of direction of environmental light 1914 to retina 1901A at a determinable rate up to 50 kilohertz. By way of example, transformable components 1904 may reorganize the pattern of direction of environmental light 1914 to retina 1901A by at least a modification of isotropy.

Further, and by way of example, transformable components 1904 may include one or more transformable components with an isotropic property or behavior, such as an optically isotropic liquid crystal. In some instances, the optically isotropic liquid crystal may provide, in response to control signals 1912, a more rapid switching time and a wider viewing angle than an anisotropic liquid crystal. For example, with an in-plane-switching electrode generating a horizontal electric field, a liquid crystal may appear optically isotropic with voltage off resulting in a dark state and the refractive-index profile may become anisotropic with voltage on with resulting transmission.

In some examples, not illustrated in FIG. 19, transformable components 1904 may be combined with a fixed focus monofocal lens. For instance, transformable components 1904 may be combined with a lens of glass or plastic or any determinable material with curved surfaces. Further, transformable components 1904 may be arranged in a pattern to create an approximately isotropic behavior. For example, transformable components 1904 may include an optically-isotropic polymer layer having a reverse lens shape on a first surface and a lens portion where the surface of the optically-isotropic polymer layer is filled with liquid crystalline polymers in some embodiments. Transformable components 1904 may also include electro-optical components that include, but not limited to, liquid crystals and polymer gels.

Additionally, not illustrated in FIG. 19, apparatus 1900 may include ultra-thin flat lenses, such as, but not limited to, lenses composed of periodic subwavelength dielectric or metal structures and liquid crystal lenses. In some instances, apparatus 1900 may also include Pancharatnam-Berry phase lenses with spatially separated focuses shifting out of the PRL axis. Further, in some instances, transformable components 1904 of apparatus 1900 may include electrically tunable liquid crystal lenses, such as, but not limited to, diffractive, refractive and gradient index lenses. For example, apparatus 1900 may transform pixel arrangement and/or indices of refraction and/or optical axis orientation. Further, and responsive to control signals 1912, one or more of transformable components 1904 may control a length of the generated focused light paths at spatial points consisting of numerous and non-contiguous retinal locations that are not PRL 1918. Further, exemplary apparatus 1900 may also include photoalignment components and/or photopatterning components.

In some instances, and based on control signals 1912 generated by controller 1906 and provisioned to transformable components 1904, apparatus 1900 may perform exemplary processes that include, but are not limited to, light polarization rotation, voltage controllable diffraction or fast switching of the LC refractive index. Further, in some instances, apparatus 1900 may incorporate, or utilize, electro-optical technology, as, for example, a local index of refraction at any given location within an active area of the electro-optical components that is determined by a voltage waveform applied across the electro-optical components at the location and controlled for the reorganization pattern with circuitry coupled to electrodes. Design features relating to index of refraction, voltages and electro-active materials of the transformable components are determinable based on the location of the apparatus, the manufacturer's needs and user's needs.

In some examples, although not illustrated in FIG. 19, apparatus 1900 may include actuating components configured to control independently a position of corresponding ones of optomechanical transformable components 1904, such as micromirrors (e.g., based on control signals generated by controller 1906). The independent control of each of the micromirrors may, for example, modify focal lengths and/or optical axes of lenses to cause a defocusing at PRL 1918 and a focusing at numerous and non-contiguous retinal locations that are not PRL, such as location 1920. In some instances, a modification of one or more of the focal lengths may be controlled by a translation and/or a rotation of corresponding ones of the micromirrors. Further, focal lengths may be modified by apparatus 1900 without requiring a determination of optical errors or image quality at PRL 1918 and/or at the non-contiguous retinal locations that are not the PRL, such as location 1920.

Some of the exemplary methods described herein may transform transiently, reversibly, or repeatedly refractive indices, radii of curvature, and/or diffractions of one or more refractive or diffractive components within at least one of an apparatus or an eye to cause a safe and effective redirection of environmental light away from a PRL of the eye to a plurality of retinal locations that are not the PRL. In some instances, some of the exemplary apparatus described herein may include one or more transformable components that are configured (e.g., via control signals generated by a corresponding controller) to produce transient, reversible, and/or repeatable alterations of indices of refraction and/or radii of curvature and/or diffractions within the apparatus or the eye. Further, some exemplary apparatus described herein may include one or more lenses and/or tunable lenses.

Some of the exemplary apparatus described herein may include one or more transformable components positioned anterior to a retina of an eye, and a controller coupled to the one or more transformable components via a conductive component. In some instances, the controller may be configured to generate and route control signals (e.g., based on executed software instructions, etc.) to the one or more transformable components. Based on a receipt of the control signals by the one or more transformable components, the apparatus may be configured to cause a weighting of an exposure of environmental light from within a field of view of the eye, which may reduce the exposure of environmental light from within the field of view of the eye to a PRL of the eye by at least 10% for a determinable interval. In some examples, the environmental light within the field of view may be exposed to the retina at a determinable rate up to 50 kilohertz.

Further, some of the exemplary methods and apparatus described herein may transform transiently, reversibly, repeatedly, or continuously refractive indices, radii of curvature, and/or diffractions of one or more refractive or diffractive components within at least one of an ophthalmic device and an eye to cause a weighting of an exposure of environmental light from within the field of view of an eye to reduce exposure to a PRL by at least 10% for a determinable interval at a determinable rate from 0 to 50 kilohertz. Some of the exemplary apparatus described herein may include one or more transformable components that, responsive to a receipt of control signals generated by a corresponding controller, may produce transient, reversible, and/or repeatable alterations of indices of refraction, radii of curvature, and/or diffraction within the apparatus or the eye that cause a weighting of an exposure of environmental light from within a field of view of an eye to reduce the exposure to a PRL by at least 10% for a determinable interval of time at a determinable rate from 0 to 50 kilohertz. In some instances, one or more of the exemplary apparatus described herein may include transformable components. For example, these transformable components may include, but are not limited to, electro-optical components, such as, but not limited to, liquid crystals and polymer gels, and/or optomechanical components. In additional, or alternate, examples, the transformable components may include, but are not limited to, photoalignment components and/or photopatterning components. Some of the exemplary methods described herein, which utilize transformable components, may include, but are not limited to, light polarization rotation processes, voltage controllable diffraction processes, and/or processes for fast switching of the LC refractive index.

In some instances, a controller coupled to a power source and to circuitry may be configured to control voltages applied to excitation electrodes to shift an optical axis of a lens (e.g., based on an execution of software instructions by one or more processes, as described herein, etc.). In some exemplary methods, described herein, the controller may receive input data that includes, but is not limited to, an eye's PRL location and/or axis. The controller may perform any of the exemplary processes described herein to process the input data and based on the processes input data, to generate and apply the control voltages to the excitation electrodes, and to control the dimensions and/or locations of initial shifts of optical axis. By controlling the dimensions and/or locations of initial shifts of optical axis, certain of the exemplary methods described herein may cause a rebooting of a visual system by a defocusing at the PRL, a focusing at non-contiguous locations that are not the PRL, and/or a weighting of an exposure of environmental light from within a field of view of an eye to reduce exposure to a PRL by at least 10% for a determinable interval of time at a determinable rate from 0 to 50 kilohertz. Although diagnostic methods, like microperimetry, may determine the location of the PRL, clinically available microperimetric testing cannot yet accurately detect all areas of decreased or increased retinal sensitivities in diseased or damaged retina. Further, clinically available diagnostic tests cannot yet accurately predict which retinal locations contain best functioning photoreceptors connected to best functioning ganglion cells, and do not yet measure an integration and summation potential of multiple areas of functioning retinal cells. If an amount of vision improvement is not satisfactory after an initial rebooting, certain of the exemplary apparatus described herein may modify an initial light defocusing at the PRL, an initial light focusing at non-PRL locations, and/or an initial weighting of exposure reduction at the PRL for repeated rebooting using any of the exemplary operations described herein.

Some of the exemplary methods and apparatus described herein may transform transiently, reversibly, or repeatedly refractive indices, radii of curvature, and/or diffractions of one or more refractive or diffractive components within at least one of the apparatus and an eye to cause a safe and effective redirection of environmental light. In some instances, one or more of the exemplary methods or apparatus described herein may cause a modification of refractive indices, radii of curvature, or diffraction of one or more refractive or diffractive elements within the apparatus or an eye. Some of the exemplary methods or apparatus described herein may cause a modification of refractive indices, radii of curvature, or diffraction of one or more refractive or diffractive elements within the apparatus or an eye, and the modifications may vary over time. Some of the exemplary methods or apparatus described herein may cause a modification(s) of refractive indices, radii of curvature, or diffraction of one or more refractive or diffractive elements within the apparatus or an eye, that may be controlled at any time before, during or after rebooting by the apparatus, the health care provider, or the user of the apparatus.

In some instances, one or more of the exemplary apparatus described herein may determine the PRL location and/or axis prior to use or insertion of the apparatus. In other instances, one or more of the exemplary apparatus described herein may determine the PRL location and/or axis may be determined during use or after insertion of the apparatus. Further, in some instances, the PRL location and/or axis may be determined by a health care provider or user using existing clinical procedures, including, but not limited to fixation or microperimetry.

As described herein, some of the exemplary apparatus described herein may include one or more transformable components coupled to a controller via a corresponding conductive component. The one or more transformable components include, for example, liquid crystals (LC), super-twisted liquid crystals, ferroelectric liquid crystals, surface stabilized ferroelectric liquid crystals (SSFLF), bi-stable liquid crystals, polymer light emitting diodes (PLED), bi-stable liquid crystals, transparent and color-tunable organic light-emitting diodes (OLEDs), or any other appropriate material. The one or more transformable components may be disposed on a surface of, or within, one or more clear components that are flat or curved, and that are composed of glass, plastic, polymers, or any other appropriate material, such as, but not limited to, polysulphones, polyetherimides, and/or other thermo-plastic materials.

As described herein, one or more of the exemplary methods may incorporate diffraction, and may utilize an apparatus having components that include, but are not limited to, at least one of a lens, a diffraction grating, an electroactive material, a deformable material, a deformable polymer, an actuator, and any determinable diffracting component. Further, one or more of the exemplary apparatus described herein may also include optomechanical components such as, but not limited to, polarizers, digital micromirror devices, micromirror arrays, deformable mirrors, and/or lenses.

Some of the exemplary apparatus described herein may include at least one control unit (e.g., a controller), and may be configured (e.g., based on control signals generated by the controller) to produce programmable weighting of exposure of environmental light from within a field of view of an eye to reduce exposure to a PRL by at least 10% or to increase exposure to retinal locations that are not the PRL more than 10% than at the PRL for a determinable interval at a determinable rate from 0 to 50 kilohertz. In some examples, one of more of these exemplary apparatus may include one or more clear components, one or more transformable components disposed on a surface of, or within, the one or more clear components, and a controller coupled electrically to the one or more transformable components via an electrically conductive layer. As described herein, the controller may be configured to generate and route control signals (e.g., based on software instructions executed by one or more processors, etc.) to the one or more transformable components, and upon receipt of the control signals, the one or more transformable components may cause weighting of exposure of environmental light from within a field of view of an eye. In some instances, an exemplary apparatus for improving and/or restoring vision, such as apparatus 2000 of FIG. 20, may include one or more clear components 2002 positioned anterior to a retina 2001A of an eye 2001 (which also includes a fovea 2001B and an optic nerve 2001C), one or more transformable components 2004 disposed on a surface of, or within, clear components 2002, a controller 2006 coupled to the one or more transformable components 2004 via conductive component 2008. Further, controller 2006 may also be coupled to a source of electrical energy, such as power source 2010, and may be configured to generate and route control signals 2012 to transformable components 2004 (e.g., based on electrical energy received from power source 2010).

Figure 20:
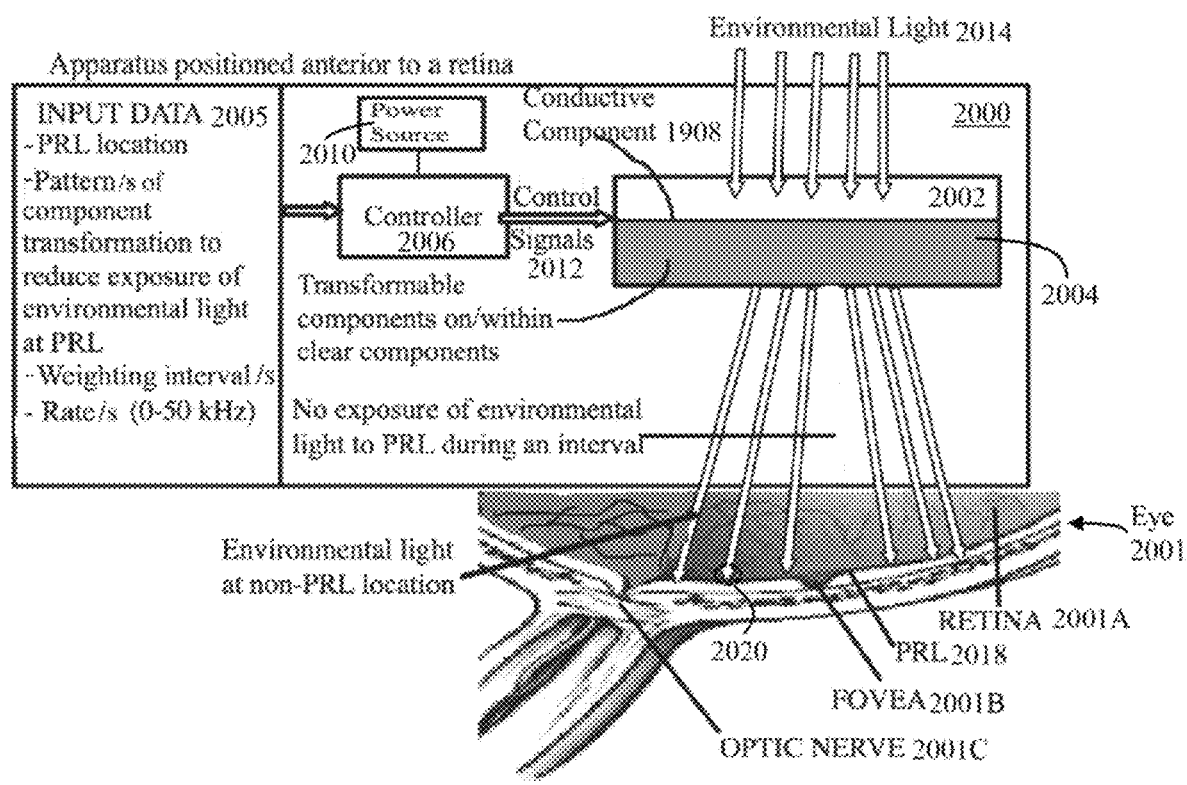
FIG. 20 is a diagram of an exemplary apparatus for improving or restoring vision, in accordance with some exemplary embodiments.

Controller 2006 may include one or more processors that, upon execution of software instructions (e.g., locally stored by the controller within a tangible, non-transitory memory or included within a received signal), causes the controller to generate and transmit control signals 2012 to transformable components 2004. As illustrated in FIG. 20, controller 2006 may receive one or more elements of input data 2005, and may be configured to process the received elements of input data 2005 and generate and route control signals 2012 to transformable components 2004. In some examples, the elements of input data 2005 may include, but are not limited to, a location of a PRL 2018 of eye 2001, information that characterizes a pattern(s) of component transformation to reduce an exposure of environmental light at PRL 2018, a weighting interval(s), and a determinable rate (e.g., ranging from zero to 50 kHz).

In some examples, and upon receipt of control signals 2012, one or more transformable components 2004 may reorganize at least one pattern of exposure of environmental light at a non-PRL location 2020 from within a field of view of eye 2001 to retina 2001A at the determinable rate up to 50 kilohertz for a determinable interval. Further, in some examples, the at least one pattern does not comprise an aperture, Further, in some examples, the determinable interval in milliseconds, seconds, minutes, hours, days, weeks, months, and/or years, may be continuous or intermittent.

Further, and by way of example, the pattern reorganization may cause a weighting of an exposure of environmental light to reduce exposure to PRL 2018 by at least 10% for a determinable interval at the determinable rate, which ranges from zero to 50 kilohertz. The weighting of an exposure of environmental light to reduce exposure to PRL 2018 may cause a rebooting of processing of environmental light 2014 by the visual system of the eye 2001. Although not illustrated in FIG. 20, apparatus 2002 may also include at least one lens. Further, in some examples, exemplary apparatus 2000 may perform any of the operations described herein to reorganize at least one pattern of exposure of environmental light 2014 to retina 2001A based on at least a transformation of an optomechanical component of apparatus 2000. The optomechanical component may include, but is not limited to, polarizers, digital micromirror devices, micromirror arrays, deformable mirrors, and/or lenses.

In some instances, transformable components 2004 may include one or more micromirrors or lenses. For example, the one or more micromirrors within transformable components 2004 may be arranged in determinable arrays of determinable shapes, and the one or more lenses within transformable components 2004 may be of determinable shapes, sizes and positions. Further, although not illustrated in FIG. 20, apparatus 2000 may integrate one or more of transformable components 2004 (e.g., the one or more of the micromirrors or lenses) with microelectronic circuits and/or corresponding micromirror technologies. For example, although not illustrated in FIG. 20, apparatus 2000 may include actuating components configured to control independently a position of corresponding ones of the micromirrors (e.g., based on control signals generated by controller 2006).

Some of the exemplary methods and apparatus described herein may cause a rebooting of a visual system of an eye (e.g., eye 1901 of FIG. 19 or eye 2001 of FIG. 20) and may cause a focusing at numerous and non-contiguous retinal locations that are not the PRL (e.g., PRL 1918 of FIG. 19 or PRL 2018 of FIG. 20). In some instances, focusing may be achieved randomly or nonrandomly by modifying a range of focal lengths and/or optical axes at different retinal locations. In additional instances, some of the exemplary methods and apparatus described herein may cause a defocusing at a PRL of an eye (e.g., PRL 1918 of eye 1901 in FIG. 19, PRL 2018 of eye 2001 in FIG. 20, etc.) by determining the optical axis of the PRL and modifying the optical axes of the lenses.

Some of the exemplary methods and apparatus described herein may cause a rebooting of a visual system to improve or restore vision in an eye through a performance of one or more projection methods. By way of example, one or more of the exemplary apparatus described herein may include one or more projection components, such as a projector, functionally coupled to a controller. The controller may include one or more processors that, upon execution of software instructions (e.g., locally stored by the controller within a tangible, non-transitory memory or included within a received signal), cause the controller to generate and transmit a control signal to the projector. Based on the received control signal, the projector may selectively redirect environmental light away from a PRL of the eye to multiple retinal locations that are not the PRL. Based on the received control signal, the projector may weight an exposure of environmental light to reduce exposure at the PRL by at least 10%. In some instances, the exemplary apparatus may include a projection component and a waveguide, and the exemplary apparatus may be configured to redirect environmental light away from the PRL of the eye to multiple retinal locations that are not the PRL, or to weight exposure of environmental light to reduce exposure at the PRL by at least 10%, utilizing the projection component and the waveguide.

Some of the exemplary methods and apparatus described herein may improve vision by causing a redirection of environmental light away from a PRL of an eye to an adequate number of retinal locations that are not the PRL in an adequate number of retinal quadrants. Some of the exemplary methods and apparatus described herein, which cause a redirection of environmental light away from a PRL of an eye to multiple retinal locations that are not the PRL, may require a determination of the location and/or axis of the PRL prior to use or insertion in the eye. The PRL location and/or axis may be determined by methods that include, but not limited to, fixation or microperimetry. In eyes with low vision, certain of the exemplary processes described herein, which redirect environmental light to multiple locations away from the PRL, may reboot the visual system and enable visual attention by other non-PRL retinal locations.

Although diagnostic methods, like microperimetry, may determine the location of the PRL, clinically available testing, including microperimetry, cannot detect all areas of decreased or increased retinal sensitivities in diseased or damaged retinas. Further, clinically available diagnostic tests cannot yet predict which retinal locations contain photoreceptors and ganglion cells that can most effectively process visual information for integration, summation and perception. Therefore, current clinical procedures cannot accurately target specific retinal locations for improving vision. Certain of the exemplary methods and apparatus described herein, which cause a redirection of environmental light away from a PRL of an eye to multiple retinal locations that are not the PRL, and which are reversible and/or safely repeatable to enable multiple redirections to improve vision, may be implemented in addition to, or as an alternate to, current clinical procedures that lack reversibility and/or repeatability.

In some instances, one or more of the exemplary apparatus described herein may include one or more light directing components positioned anterior to a retina of an eye. Further and in addition to the light directing component(s), one or more of these exemplary apparatus may also include a light source positioned anterior to the retina. The light source does not produce corneal vitrification. For example, some of the exemplary apparatus described herein may include one or more components that direct light from the light source (e.g., at least one of a laser light source and a non-laser light source) to multiple non-contiguous portions of at least one structure anterior to the retina to cause a rebooting of processing of environmental light by the visual system by causing a redirection of environmental light away from the PRL to multiple retinal locations that are not the PRL or a reduction of exposure of environmental light at the PRL during a specified interval or a defocusing environmental light at the PRL and a focusing the light at a plurality of non-contiguous and non-PRL retinal locations or any combination thereof.

Figure 21:
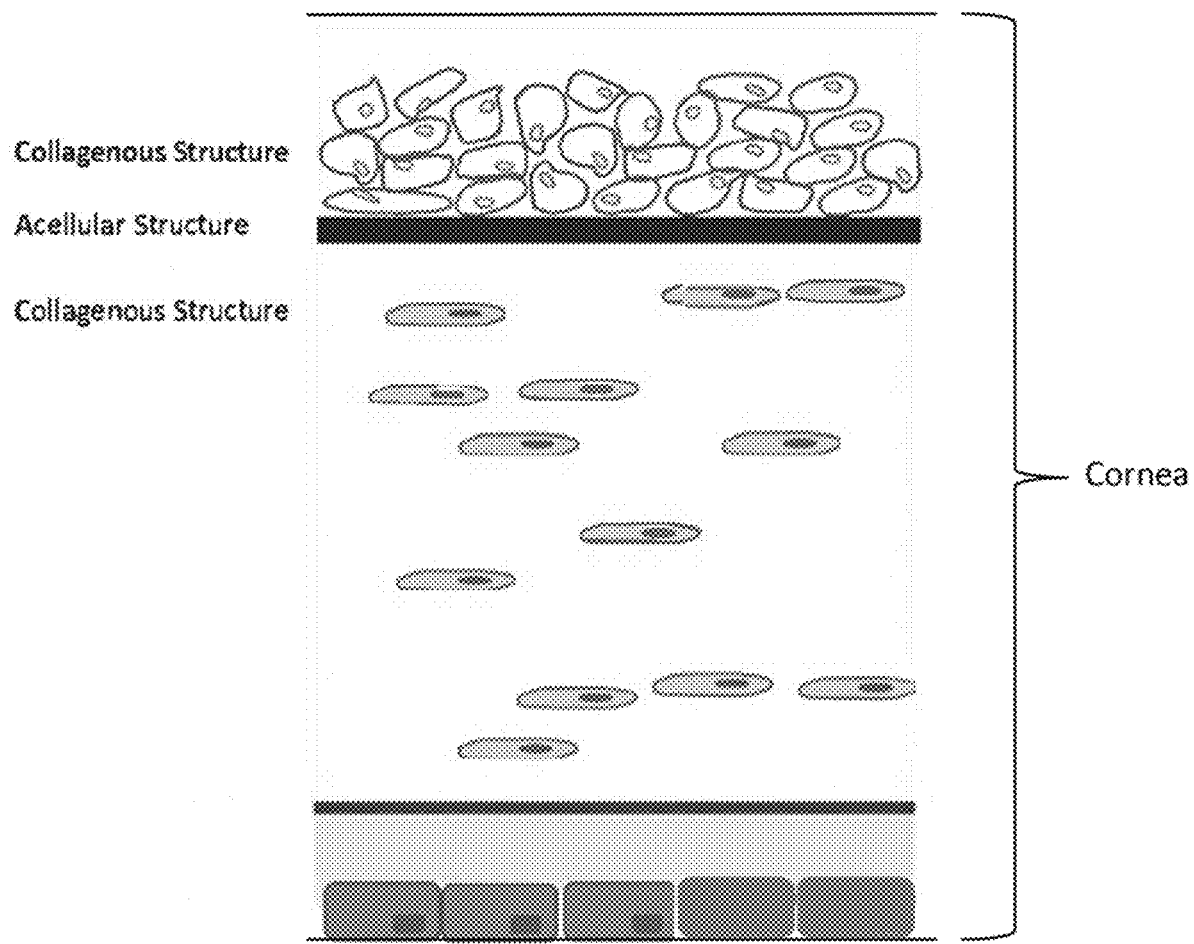
FIG. 21 is a cross-section of the cornea showing acellular and collagenous layers.

Structures to which light is directed from the laser or non-laser light source include, but are not limited to, acellular structures and/or collagenous structures with or without cells within the eye anterior to the retina. The phrase "within the eye", as defined herein, may include, but is not limited to, within the cornea of the eye (e.g., as illustrated in FIG. 21), within an anterior chamber of the eye, within a crystalline lens of the eye, and within a posterior chamber of the eye. Further, acellular structures within the eye, as defined herein, may include structures native to the eye and non-native structures placed within or on the eye. Examples of acellular structures that are non-native to the eye, but within the eye, include, but are not limited to, intraocular lenses, donor acellular corneal lenticules, and biosynthetic collagenous inlays. Further, examples of acellular structures native to the eye include, but are not limited to, corneal layers without cells and acellular portions of the crystalline lens.

In some instances, one or more of the exemplary methods and apparatus described herein, which direct light from the light source to acellular or approximately acellular structures, rather than to cellular structures within the eye, may improve safety and efficacy by decreasing potential wound healing effects, potential deleterious effects or potential reduced efficacy caused by targeting cellular structures. Collagenous structures are structures containing collagen and include structures native to the eye and structures inserted in or on the eye, such as, but not limited to, structures with cells, including but not limited to, biosynthetic collagen, corneal stroma, portions of the sclera and portions of the crystalline lens.

Some of the exemplary methods and apparatus described herein target structures for laser and non-laser light treatment based on their collagen fibril intertwining and collagen fibril dispersion, both of which may alter biomechanical and optical behavior of the structures. In some instances, the targeting of structures or portions of structures with increased fibril intertwining and fibril dispersion may increase the efficacy and efficiency of procedures that cause a redirection of environmental light away from a PRL of an eye to multiple locations that are not the PRL. For example, in the cornea, individual collagen fibrils are intertwined most densely in the anterior acellular layer between the epithelium and stroma. Dense interconnections render those corneal portions more rigid and more mechanically active. Atomic force microscopy has demonstrated that the anterior acellular layer has the greatest elastic modulus in the cornea, e.g., approximately three times greater than the elastic modulus of the anterior stroma (less than 20 μm in depth). In addition, many of the anterior stromal fibrils insert into the anterior acellular layer, as can be demonstrated using second harmonic imaging confocal microscopy. Beneath the anterior acellular layer, fibrils in the anterior stroma are also intertwined, but less densely than in the anterior acellular layer. The densities of fibril branching and fibril inclination from an aligned position decrease exponentially with depth from the anterior to posterior cornea, and the average collagen inclination is predominantly parallel to the tissue surface at all depths. However, in the central cornea, the spread of inclination angles is greatest in the anterior-most stroma (reflecting the increased lamellar intertwining in this region), and decreases with tissue depth. The most anterior part of the stroma (less than 20 μm from the anterior acellular layer) may be characterized by the greatest elastic modulus within the stroma. For example, the rigidity is three times greater in the anterior third of the stroma than in the posterior third.

In addition to second harmonic-generated imaging, fibril dispersion may be measured by X-ray diffraction and scattering studies. Fibrils are more dispersed in the anterior acellular layer than in the underlying stroma. Collagen fibrils are proportionally less dispersed and more aligned in the posterior two thirds of the cornea, while in the anterior third (and, especially, in the anterior sixth with maximal dispersion nearest to the anterior acellular layer) of the central and paracentral cornea, the collagen fibrils are arranged in many directions. In addition, fibril dispersion exhibits a spatial variation over the corneal surface with fibers strongly aligned along the nasal-temporal and superior-inferior meridians and more dispersed in transition zones within the four quadrant regions of the corneal surface, with fibril dispersion maximal in the central section in each quadrant. The amount of dispersion of collagen fibers in the transition zone may vary among individual corneas. Further, it also has been shown by X-ray diffraction that there is variation in the proportion of fibrils oriented within 45° sectors of the nasal-temporal and superior-inferior meridians between different healthy human corneas.

The spatial distribution of fibril dispersion also may differ between healthy and diseased corneas. Regions where fibrils are most fully dispersed are approximately isotropic (i.e., arranged in all directions), and an approximately isotropic portion with almost fully dispersed fibrils exhibits an approximately isotropic biomechanical and/or optical property or behavior (i.e. an approximately equivalent isotropic biomechanical and/or optical property or behavior in all directions). A corneal property, such as an elastic modulus or other property, is anisotropic when, upon testing along one radial meridian of the cornea, the value differs from values obtained along different meridians. For example, Brillouin microscopy measures corneal anisotropy both in vivo and ex vivo, and clinical measurement with en face Brillouin corneal mapping may be used to determine areas of maximal isotropy.

In some instances, a greater amount of surface deformation, a corneal mechanical behavior, may occur in the central section in each quadrant of the cornea than in the nasal-temporal and superior-inferior sections because of the increased degree of fibril dispersion. Some of the exemplary methods and apparatus described herein modify corneal portions with fibril dispersion and/or modify fibril dispersion in corneal portions. For example, the more compliant the portion of the cornea, the easier it is to deform. Modifying portions of areas of intertwined collagen fibers may also alter a rigidity of the anterior stroma, alter a corneal curvature, alter light refraction, alter vision of the eye, or any combination thereof. Some of the exemplary methods and apparatus described herein modify corneal portions with intertwined fibrils/fibers and/or modify fibril/fiber intertwining in corneal portions. Measurement of compliance of a corneal layer or portion can be done, for example, by corneal indentation, estimation of Young's modulus based on a fluid-filled spherical shell model with Scheimpflug imaging, and ultrasound surface wave elastography.

Although clinical techniques for measuring corneal biomechanical responses became available about fifteen years ago, these clinical techniques could not measure localized biochemical behavior until recently. While ex vivo analysis of the corneal surface has been present for decades, it is only recently that methods have been developed to study corneal biomechanics in vivo. Further, although clinical measurement of corneal biomechanical responses has been used diagnostically for glaucoma, keratoconus and other corneal ectatic disorders, localized biomechanical criteria have been not been used to date in planning eye procedures unrelated to abnormal corneas with ectasia. Some of the exemplary methods and apparatus described herein may receive, process, and utilize input from corneal compliance and/or input from mapping of localized corneal compliance and/or input from mapping of corneal anisotropy/isotropy, as illustrated in the corneal anisotropy map in FIG. 22. For example, in FIG. 22, 0 corresponds to an isotropic corneal portion and a value>2 corresponds to a highly anisotropic corneal portion.

In some instances, some of the exemplary methods and apparatus described herein may safely and effectively reboot the visual system of an eye by transforming a property or behavior of structures native or non-native to the eye and positioned on or within the eye through a transformation of approximately isotropic portions of structures within the eye, through a transformation of at least one portion of a structure on or within the eye into an approximately isotropic structure and/or a structure exhibiting at least one property and/or behavior in all directions, through a transformation of isotropy of at least one portion of a structure on or within the eye or through a transformation of at least one portion of a structure on or within the eye based on at least one portion's isotropy or anisotropy.

Further, some of the exemplary methods and apparatus described herein may safely and effectively reboot the visual system of an eye through a transformation of mechanical properties of structures within an eye. For example, the mechanical properties may be transformed efficiently and safely by removing and/or mechanically reinforcing small determinable amounts of mechanically active structures or portions of structures in determinable locations on or within the eye. Additionally, in some instances, the mechanical properties may be transformed efficiently and safely by removing and/or mechanically reinforcing small determinable amounts of approximately mechanically isotropic structures or portions of structures in determinable locations on or within the eye.

Figure 22:
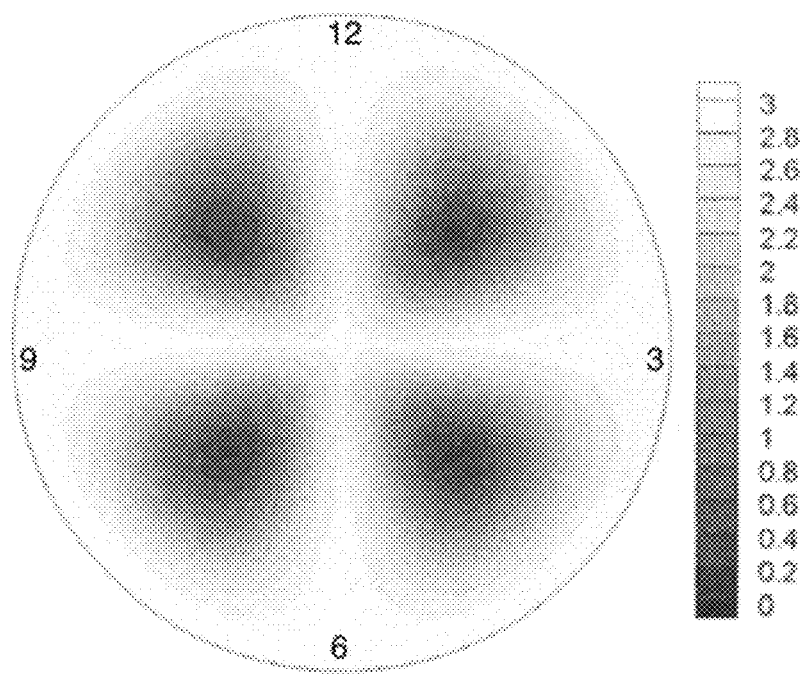
FIG. 22 is an anisotropy map of the cornea with 0 corresponding to isotropy and a value>2 corresponding to high anisotropy.

Some of the exemplary methods and apparatus described herein may reboot a visual system of an eye safely and effectively through a transformation of optical properties of structures on or within the eye. In some instances, the refractive properties may be transformed efficiently and safely by modifying small determinable amounts of anisotropic and/or approximately isotropic structures or portions of structures. For example, the parameter $\kappa(\rho, \theta)$ represents a continuous distribution of the collagen fibrils over the entire cornea of the eye, and exhibits a minimum value of zero where fibrils are perfectly aligned along their preferential orientations, and a maximum value of ⅓ where fibrils are fully dispersed and the cornea behaves nearly isotropically. As (i) fibrils in the cornea are not oriented isotropically everywhere but, in precise locations, (ii) about 60% of the fibrils are uniformly dispersed, leading to an isotropic behavior, and (iii) about 40% of the fibrils are oriented with differing amounts of anisotropy (as illustrated in FIG. 22), some of the exemplary methods and apparatus described herein may reboot the visual system effectively, efficiently and safely by directing laser or non-laser light to portions of the cornea based on the isotropic or anisotropic behavior or properties of the portions and/or modifying the isotropy of portions of the cornea.

Some of the exemplary methods and apparatus described herein for rebooting the visual system and/or improving or restoring vision may include at least one of a light source and one or more components directing light from the light source to at least a plurality of non-contiguous portions of a cornea of an eye. In additional, or alternate, instances, some of the exemplary methods and apparatus described herein, which reboot the visual system and/or improve or restore vision, may also include one or more components directing light from the light source to at least a plurality of non-contiguous portions of at least an anterior acellular layer overlying anterior corneal portions that may be selected based on the degree of isotropy or anisotropy of the corneal portions beneath the anterior acellular layer. For example, the light from the light source may be directed to approximately isotropic portions of a cornea. The light source may include at least one of a laser or a non-laser light source.

Figure 23:
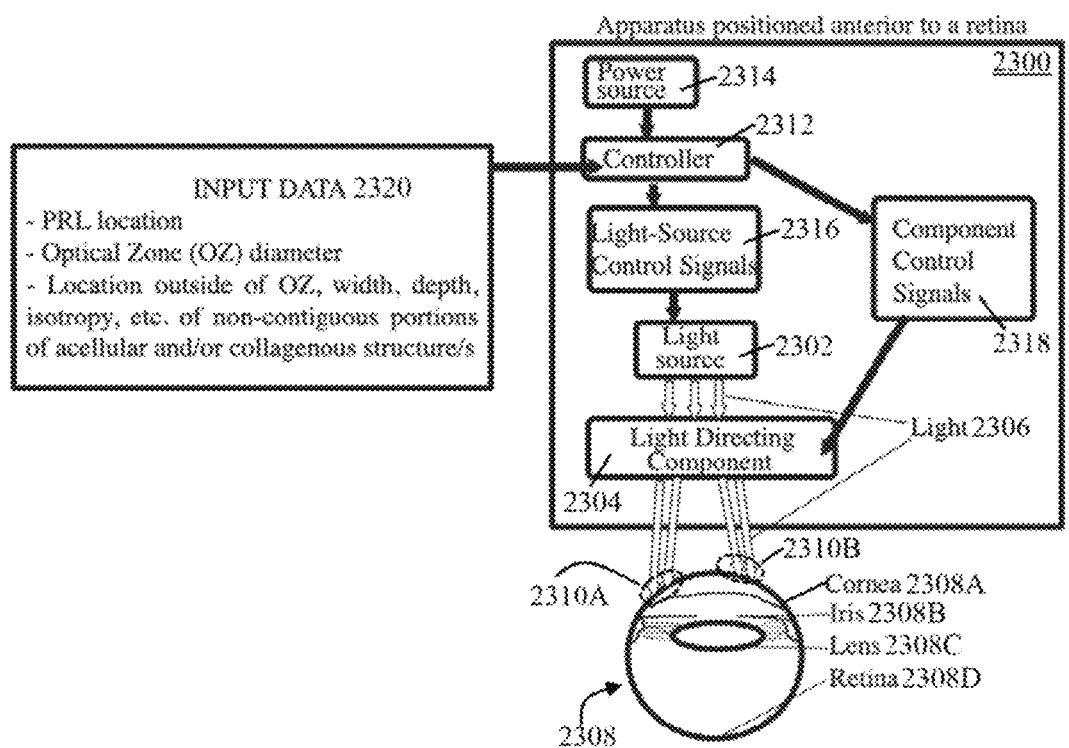
FIG. 23 is a diagram of an exemplary apparatus for improving or restoring vision, in accordance with some exemplary embodiments.

By way of example, and as illustrated in FIG. 23, an exemplary apparatus 2300 for improving or restoring vision includes at least one of a light source 2302 and a light directing component(s) 2304 directing light 2306 from light source 2302 to at least a plurality of non-contiguous portions of a cornea 2308A of an eye 2308, shown generally as non-continuous portions 2310A and 2310B. In some instances, the cornea may be a normal for age-cornea. Light source 2302 may include at least one of a laser or a non-laser light source, and light source 2302 does not produce corneal vitrification. Further, the non-contiguous portions, including non-continuous portions 2310A and 2310B, may be located outside a central optical zone and may include at least an acellular layer of a cornea, such as cornea 2308A. In some instances, and through the redirection of light 2306 from light source 2302 to at least the plurality of non-contiguous portions of a cornea 2308A, apparatus 2300 may modify corneal isotropy outside the central optical zone.

As illustrated in FIG. 23, apparatus 2300 may also include a controller 2312 coupled electrically to a source of electrical energy, such as power source 2314, to light source 2302, and to one or more components, such as light directing component(s) 2304 disposed between the light source 2302 and cornea 2308B. Based on electrical energy received from power source 2314, controller 2312 may be configured to generate and route light-source control signals 2316 to light source 2302, and to generate and route component control signals 2318 to light directing component(s) 2304. For example, controller 2312 may include one or more processors that, upon execution of software instructions (e.g., locally stored by the controller within a tangible, non-transitory memory or included within a received signal), causes controller 2312 to generate and transmit light-source control signals 2316 to light source 2302, and to generate and route component control signals 2318 to light directing component(s) 2304. In some instances, upon receipt of light-source control signals 2316, light source 2302 may be configured to generate light 2306, which may illuminate and fall incident onto light directing component(s) 2304. Further, and responsive to component control signals 2318, light directing component(s) 2304 may perform any of the exemplary processes described herein to direct light 2306 to at least the plurality of non-contiguous portions of cornea 2308A.

In some examples, light source 2302 of apparatus 2300 may include a laser light source, such as an ArF excimer laser emitting ultraviolet radiation at 193 nm (e.g., laser light), and controller 2312 may be configured to direct the laser light to a plurality of non-contiguous portions of at least an anterior acellular layer of the cornea based on input data 2320, which may include, among other things, a location of a PRL of eye 2308, a determinable diameter of the central optical zone (OZ) of cornea 2308A, and determinable locations, depths and surface areas of the non-contiguous corneal portions, which may be based on isotropic behavior or properties of the portions. For example, controller 2312 may be configured (e.g., by the executed software instruction) to control an ablation of four circular corneal portions, including at least the anterior acellular layer overlying the stroma of the cornea and having a diameter of 1 mm, to a depth of 20 microns (if the epithelium is removed manually over the portions) or 80 microns (for transepithelial ablation). In some instances, each of the four circular corneal portions may be centered on a 6 mm OZ centered on the PRL (by patient fixation on a light) and may overlie the most isotropic corneal portions (as illustrated in FIG. 22 and described herein) at the 1:30 o'clock, 4:30 o'clock, 7:30 o'clock and 10:30 o'clock positions.

In some examples, one or more of the exemplary processes described herein may utilize a first apparatus that includes a laser light source and a controller coupled electrically to the laser light source and one or more laser components in conjunction with a separate, second apparatus disposed between the laser light source and a cornea to direct the laser light delivered by the first apparatus to a plurality of non-contiguous portions of at least an anterior acellular layer of the cornea. The central optical zone may, for example, include a circular region of the cornea that is at least 2 mm in diameter. In some instances, the central optical zone is at least 3 mm in diameter, and in other instances, the central optical zone is at least 4 mm in diameter. Some of the exemplary methods and apparatus described herein may include at least one of a light source and a component(s) directing light from a light source, and may perform any of the operations described herein to cause an improvement of vision or a restoration of vision. Some of the exemplary methods and apparatus described herein may include at least one of a light source and a component(s) directing light from a light source, and may perform any of the operations described herein to modify corneal isotropy. In some instances, a modification to corneal isotropy outside the corneal optical zone may include a modification, in at least one direction, of at least one of a mechanical property or a mechanical behavior of the cornea or a portion of the cornea. In additional, or alternate, instances, a modification to corneal isotropy outside the corneal optical zone may include a modification, in at least one direction, of at least one of an optical property or an optical behavior of the cornea or a portion of the cornea.

In some examples, one or more of the exemplary apparatus described herein may include a light source (e.g., light source 2302 of apparatus 2300 in FIG. 23), and the light source may include at least one of a laser and a non-laser light source. The light source may, for instance, emit at least one of ultraviolet radiation or infrared radiation. Further, some of the exemplary methods described herein and the exemplary apparatus described herein, which include at least one of a light source and a component(s) directing light from the light source, may cause corneal surface patterning. The corneal surface patterning may, for example, be at least one of phototunable and approximately reversible. Additionally, in some examples, one or more of the exemplary methods described herein and the exemplary apparatus described herein, which include at least one of a light source and a component(s) directing light from the light source, may also cause mechanical reinforcement of a plurality of non-contiguous corneal portions to which light from the light source is directed. Further, some of the exemplary methods described herein and the exemplary apparatus described herein, which include at least one of a light source and a component(s) directing light from the light source, may cause mechanical reinforcement of multiple portions based on isotropy/anisotropy criteria. In further examples, one or more of the exemplary methods described herein and the exemplary apparatus described herein, which include at least one of a light source and a component(s) directing light from the light source, may also release mechanical reinforcement agents.

Some of the exemplary methods described herein and the exemplary apparatus described herein, which include at least one of a light source and a component(s) directing light from the light source, may cause a defocusing of environmental light from within a field of view of an eye at a PRL and/or a focusing at numerous and non-contiguous retinal locations that are not the PRL. Some of the exemplary methods and apparatus described herein may cause a defocusing of environmental light from within a field of view of an eye at a PRL of the eye and a focusing at the plurality of non-contiguous retinal locations that are not the PRL, and do not require measurement by or input into the apparatus of optical errors at the non-contiguous retinal locations or at the PRL.

Some of the exemplary methods described herein and the exemplary apparatus described herein, which include at least one of a light source and a component(s) directing light from the light source, may improve and/or restore vision in an eye with an impairment and/or a loss of central and/or peripheral vision by causing a defocusing of environmental light from within a field of view at a PRL. Some of the exemplary methods and apparatus described herein may cause a defocusing of environmental light from within a field of view at a PRL by modifying at least a plurality of portions of a cornea outside a central optical zone. For example, the plurality of portions of the cornea may include mechanically active portions of the cornea. Some of the exemplary methods described herein and the exemplary apparatus described herein, which include at least one of a light source and a component(s) directing light from the light source, may cause a defocusing of environmental light from within a field of view at a PRL and may modify an optical property or behavior and/or a mechanical property or behavior in a plurality of portions outside a central optical zone of a structure positioned anterior to a retina. The mechanically active portions of the cornea may be selected based on the amount of their mechanical activity compared to other corneal portions.

Some of the exemplary methods described herein and the exemplary apparatus described herein, which include at least one of a light source and a component(s) directing light from the light source to cause a rebooting of a visual system of an eye, may cause surface patterning of any structure positioned on or within an eye. In some instances, the surface patterning may be at least one of phototunable and approximately reversible. Some of the exemplary methods described herein and the exemplary apparatus described herein, which include at least one of a light source and a component directing light from the light source, may cause mechanical reinforcement of a plurality of non-contiguous portions of any structure positioned on or within an eye to which light from the light source is directed. Further, Some of the exemplary methods described herein and the exemplary apparatus described herein, which include at least one of a light source and a component directing light from the light source, may cause mechanical reinforcement of a plurality of portions of any structure positioned on or within an eye to which light from the light source is directed, which reinforcement may be based on isotropic or anisotropic criteria. Some of the exemplary methods described herein and the exemplary apparatus described herein, which include at least one of a light source and a component directing light from the light source, may release mechanical reinforcement agents for reinforcing any structure positioned on or within an eye.

Some of the exemplary apparatus described herein, or exemplary components within these apparatus, which may direct light from a light source, may be positioned intraocularly, intra-corneally or extraocularly anterior to a retina of an eye, and may be configured to allow transmission from a light source, including at least one of a laser light source and a non-laser light source, to multiple non-contiguous portions of at least one structure anterior to the retina. The at least one structure anterior to the retina may be located intraocularly, intra-corneally or extraocularly and may include, but is not limited to, an acellular structure native to the eye, such as a structure within a cornea or crystalline lens of the eye, or an acellular structure non-native to the eye, such as a contact lens, an intracorneal inlay, an intraocular lens or a donor corneal acellular structure, or another intraocular, intra-corneal or extraocular structure, such as a collagenous structure either native or non-native to the eye, such as corneal stroma, donor corneal stroma or biosynthetic collagen.

Some of the exemplary apparatus described herein, which improve vision in an eye with an impairment of central vision, may cause a defocusing of environmental light from within a field of view of the eye at a PRL and/or a focusing at numerous and non-contiguous retinal locations that are not the PRL, and may direct light from a light source to multiple non-contiguous portions of at least one structure anterior to the retina, The at least one structure anterior to the retina may be located intraocularly, intra-corneally or extraocularly, and may include, but is not limited to, an acellular structure, such as a contact lens, an intracorneal inlay, an intraocular lens or another intraocular, and intracorneal or extraocular acellular or collagenous structure. Some exemplary apparatus may include a component directing light from a light source, and the component may be placed anterior to a retina of the eye. In some instances, one or more of these exemplary apparatus may prevent transmission of light from the light source to at least one portion of at least one structure anterior to the retina, the light source includes at least one of a laser light source and a non-laser light source, and the at least one structure is located anterior to the retina intraocularly, intra-corneally or extraocularly.

Some of the exemplary apparatus described herein, which improve vision in an eye with an impairment of central vision by causing a defocusing of environmental light from within a field of view of the eye at a PRL and/or a focusing at numerous and non-contiguous retinal locations that are not the PRL, may direct light from a light source, may be positioned anterior to a retina of an eye, and may be configured to allow transmission from the light source (including at least one of a laser light source and a non-laser light source) to multiple non-contiguous portions of at least an acellular and/or collagenous structure anterior to the retina. In some instances, the at least one acellular and/or collagenous structure anterior to the retina may be disposed within a cornea or a crystalline lens of the eye. Further, some of the exemplary apparatus described herein, which direct light from a light source, may be positioned anterior to a retina of an eye and may prevent transmission from the light source to a portion or portions of at least one acellular or collagenous structure anterior to the retina. The light source may, for example, include at least one of a laser light source and a non-laser light source, and the at least one acellular and/or collagenous structure anterior to the retina may be disposed within a cornea or a crystalline lens of the eye.

In some instances, one or more of the exemplary methods described herein may include utilizing a laser apparatus, or an apparatus accessory to a laser, to direct light from a light source and to restrict a laser treatment to multiple non-contiguous volumes of at least an acellular structure (e.g. a layer) of a cornea. Further, some of the exemplary apparatus described herein may include a laser apparatus, or an apparatus accessory to a laser, configured to direct light from a light source and to restrict a laser treatment to multiple non-contiguous volumes of at least a structure (e.g. a layer or portion) of a cornea. Additionally, some of the exemplary apparatus described herein, or one or more components of these exemplary apparatus, may direct laser light from a laser light source and may be used for transepithelial laser treatment of the cornea. Some of the exemplary apparatus described herein, or one or more components of these exemplary apparatus, may be used after a non-laser removal of a corneal epithelium, which may be performed manually with a spatula, diamond burr, or any other instrument, and by any determinable method for corneal epithelial removal.

Further, in some instances, one or more of the exemplary apparatus described herein, or one or more components of these exemplary apparatus, may direct light from a light source and may include, but are not limited to, one or more additional components with laser light transmissible-apertures for laser treatment of multiple non-contiguous volumes of at least an acellular layer of a cornea and/or a collagenous layer of a cornea. Some of the exemplary apparatus described herein, or one or more components of these exemplary apparatus, may direct light from a light source and may include, but are not limited to, one or more further components that include laser-light absorbable matter surrounding multiple regions without laser light-absorbable matter located in non-contiguous areas of the one or more components. The further one or more components may, for example, restrict laser treatment to multiple non-contiguous volumes of at least an acellular layer of a cornea or a collagenous layer of the cornea. The laser light absorbable matter may include, for example, polymethylmethacrylate for laser light at 193 nm. In some examples, the portion of the one or more further components with laser light absorbable matter may surround the regions corresponding to the multiple non-contiguous volumes to be removed and may be attached to an underlying portion of the further one or more components with laser light transmissible matter, such as, for example, quartz.

Some of the exemplary methods and apparatus described herein may cause transient and/or safely repeatable redirection of environmental light away from a PRL of an eye to multiple retinal locations that are not the PRL by direction of light from a light source to multiple non-contiguous portions of at least one of an acellular structure and a collagenous structure, For example, the structure may be located anterior to a retina, the light source may include at least one of a non-laser light source and a laser light source. Some of the exemplary apparatus described herein may include a light source and components configured to treat multiple non-contiguous portions that are volumes in or on an eye including at least one of an acellular structure and a collagenous structure and to redirect light from the light source away from the PRL to a plurality of retinal locations that are not the PRL. Further, in some instances, one or more of the exemplary methods described herein may utilize an apparatus, which includes a light source and components, to treat multiple non-contiguous portions that are volumes in an eye including at least one of an acellular ocular structure and a collagenous ocular structure, and to redirect light from the light source away from a PRL to a plurality of retinal locations that are not the PRL. The light source may include at least one of a non-laser light source and a laser light source.

Some of the exemplary apparatus described herein may include a laser and components for corneal ablation that are configured to ablate at least an acellular layer of a cornea. Further, one or more of the exemplary apparatus described herein include a laser and components for corneal ablation that are configured to ablate corneal epithelium and/or corneal stroma. Examples of ablative lasers include, but are not limited to, an argon fluoride excimer laser emitting far ultraviolet light at a wavelength including, but not limited to, 193 nanometers and a solid-state laser. One or more of exemplary apparatus described herein may direct light from laser light sources including, but not limited to, a laser light source emitting infrared or ultraviolet light producing photoablation.

Some of the exemplary apparatus described herein may include a laser light source, a controller coupled electrically to one or more laser components, and at least one component configured to ablate portions of a cornea. The at least one component may, for example, be disposed between the laser light source and a surface of multiple non-contiguous portions to be ablated, and the at least one component may include a laser light directing component, a laser light directing control, a laser light-occluder, a programmable occlusion microarray, and/or a laser light-occlusion control, Some of the exemplary apparatus described herein may include a laser light source and components for corneal ablation, and examples of the components include, but are not limited to, a sensor, a processor, a controller, a video camera, an eye tracker, a display, a lens, a laser beam shaping component, a laser beam aiming component, a laser scanning component, and/or delivery optics.

In some instances, one or more of the exemplary apparatus and methods described herein may produce ablation of a microvolume, of any desired volumetric shape of corneal tissue, including at least a portion of an acellular layer and/or a collagenous layer. The microvolumes may, for example, include corneal epithelium and/or corneal stromal tissue, although in other examples, the microvolumes may include only corneal stromal tissue. Further, in some instances, one or more of the exemplary apparatus and methods described herein may produce ablation of a microvolume, of any determinable volumetric shape, of corneal tissue, including at least a portion of a rigid anterior layer and/or an anterior acellular layer. For example, the ablated microvolumes may be characterized by a depth of any determinable depth no deeper than 200 microns, with or without an anterior surface transition zone, and be characterized by a surface area with a smallest diameter of no less than 0.05 mm and a largest diameter of no more than 5 mm. The surface area may be circular, hexagonal, elliptical, oval, square, rectangular, or of any determinable shape.

Additionally, in some instances, one or more of the exemplary apparatus and methods described herein may produce ablation of a microvolume, of any determinable volumetric shape of a contact lens that includes ablatable material, an intraocular lens that includes ablatable material, or an intraocular lens device that includes ablatable material. The ablated microvolumes may for example, be characterized by a depth of any depth no deeper than 200 microns, with or without an anterior surface transition zone, and may be characterized by a surface area with a smallest diameter of no less than 0.05 mm and a largest diameter of no more than 5 mm. The surface area may be circular, hexagonal, elliptical, oval, square, rectangular, or of any determinable shape.

Some of the exemplary apparatus described herein may include a laser light source and components for corneal ablation that are configured to ablate multiple non-contiguous microvolumes in corneal regions outside a central optical zone having a diameter greater than 2 mm. Examples of ablation centration methods include, but are not limited to, coaxially sighted corneal light reflex, coaxially sighted, corneal light reflex, and the center of entrance pupil.

Some of the exemplary apparatus described herein may include a laser configured to ablate portions of a cornea, and the ablation may be performed while the subject is fixating on a light target, thereby determining the PRL axis.

Some of the exemplary apparatus described herein, which are configured to ablate portions of a cornea, do not require determination of the PRL location or axis prior to or during ablation, such as, for example, during ablation of multiple non-contiguous portions outside a 4 mm or larger central optical zone.

Some of the exemplary apparatus described herein may include at least one or more components configured to direct laser light to multiple non-contiguous portions of a cornea or a crystalline lens in pulses of at least one of a femtosecond duration, a nanosecond duration, or a picosecond duration to cause a rebooting of a visual system of an eye by causing a redirection of light away from a PRL to a plurality of retinal locations that are not the PRL and/or by causing a defocusing of environmental light from within a field of view of the eye to the PRL and/or a focusing at a plurality of non-contiguous retinal locations that are not the PRL. Further, in some instances, one or more of the exemplary apparatus described herein may include one or more components configured to direct laser light to at least one of a corneal epithelium, a corneal acellular layer, or a corneal stroma in pulses of at least one of a femtosecond duration, a nanosecond duration, or a picosecond duration. Additionally, some of the exemplary apparatus described herein may include, but are not limited to, a laser system producing photoablation, photodisruption, photoionization, photodissociation, photochemical effects, or any combination thereof. One or more of exemplary apparatus described herein may include one or more laser light sources, and examples of these laser light sources include, but are not limited to, a laser light source emitting infrared, visible or ultraviolet light. One or more of exemplary apparatus described herein may direct light from laser light sources including, but not limited to, a laser light source emitting infrared, visible or ultraviolet light.

Some of the exemplary apparatus described herein may include one or more components configured to direct laser light to at least one of an acellular layer of a cornea, a corneal epithelium, or a corneal stroma in pulses of at least one of a femtosecond duration, a nanosecond duration, or a picosecond duration. For example, one or more components may include at least one of a laser light directing component, a laser light directing control, an applanation occluder, a contact liquid occluder, an immersion lens, a programmable occlusion microarray, a laser light-occlusion control, a lens, a laser beam shaping element, or a laser beam aiming element. Further, one or more of the exemplary apparatus described herein may produce any determinable spot size. In some instances, one or more of the exemplary apparatus described herein may include components producing any determinable pulse energy, pulse frequency, and/or laser pattern (such as, for example, spiral or raster), and may utilize any determinable contact interface (such as, for example, curved or flat) or centration technique (mechanical or computer). By way of example, any determinable average power up to about 100 W, peak power up to terawatt levels, repetition rate up to 100 megahertz, pulse duration, polarization, and/or wavelength from extreme ultraviolet to mid-infrared may be used for laser-matter interactions, including ultrafast laser-matter interactions. Additionally, some of the exemplary apparatus described herein may produce any ultrafast laser-matter interaction, including with any pulse duration from femtosecond to attosecond.

Some of the exemplary apparatus described herein may be configured to cause transient and repeatable redirection of environmental light away from a PRL of an eye to multiple retinal locations that are not the PRL, and include at least one component configured to direct laser light to at least one of an acellular layer of a cornea, a corneal epithelium, or a corneal stroma in pulses of at least one of a femtosecond duration, a nanosecond duration, or a picosecond duration to modify and/or remove multiple non-contiguous microvolumes.

In some instances, one or more of the exemplary apparatus and methods described herein may modify and/or remove a microvolume of any determinable volumetric shape of corneal tissue. Some of the exemplary apparatus and methods described herein also may modify and/or remove a microvolume, of any determinable volumetric shape, of corneal tissue. Further, some of the exemplary apparatus and methods described herein may modify and/or remove a microvolume, of any determinable volumetric shape, in mechanically active portions of a cornea. In some instances, one or more of the exemplary apparatus described herein may direct light to microvolumes having any depth no deeper than 200 microns and having a surface area with a smallest diameter of no less than 0.05 mm and a largest diameter of no more than 5 mm. The surface area may be circular, hexagonal, elliptical, oval, square, rectangular, of any determinable shape.

Some of the exemplary apparatus described herein may include at least one component configured to direct laser light to at least one of a cornea, a natural crystalline lens, a contact lens, an intracorneal inlay, an intraocular lens, intraocular device or any other structure positioned anterior to a retina of an eye in pulses of at least one of a femtosecond duration, a nanosecond duration, or a picosecond duration. Some of the exemplary apparatus described herein, which improve vision in an eye with an impairment of central vision by causing a defocusing of environmental light from within a field of view of an eye at a PRL and/or a focusing at numerous and non-contiguous retinal locations that are not the PRL, may direct laser light to at least one of a cornea, a natural crystalline lens, a contact lens, an intracorneal inlay, an intraocular lens, an intraocular device or any other structure positioned anterior to a retina of an eye in pulses of at least one of a femtosecond duration, a nanosecond duration, or a picosecond duration. In some instances, one or more of the exemplary apparatus described herein may modify a microvolume of any determinable volumetric shape. The microvolumes may, for example, be characterized by a determinable depth no deeper than 200 microns, and be characterized a surface area with a smallest diameter of no less than 0.05 mm and a largest diameter of no more than 5 mm. The surface area may be circular, hexagonal, elliptical, oval, square, rectangular, or of any shape, Further, in some instances, one or more of the exemplary apparatus and methods described herein may modify an index of refraction or a radius of curvature.

Some of the exemplary apparatus described herein may include lasers producing laser thermal keratoplasty, but not producing corneal photovitrification, to modify multiple non-contiguous volumes of at least an acellular layer a cornea or any other acellular or collagenous structure positioned anterior to a retina of an eye. Some of the exemplary apparatus described herein may include, but are not limited to, lasers, such as holmium and thulium lasers, the producing laser thermal keratoplasty, but not producing corneal photovitrification, to modify multiple non-contiguous volumes of at least an acellular layer a cornea or any other acellular or collagenous structure positioned anterior to a retina of an eye to cause a rebooting of a visual system of an eye by causing a redirection of light away from a PRL to a plurality of retinal locations that are not the PRL and/or by causing a defocusing of environmental light from within a field of view of the eye to the PRL and/or a focusing at a plurality of non-contiguous retinal locations that are not the PRL. Some of the exemplary apparatus described herein may include lasers producing laser thermal keratoplasty to modify multiple non-contiguous volumes of at least one of corneal stroma and corneal epithelium.

Some of the exemplary apparatus described herein may be configured to deliver radiofrequency current (350-400 kHz) to modify multiple non-contiguous volumes of at least an acellular layer of a cornea or any other acellular or collagenous structure positioned anterior to a retina of an eye. Further in some instances, one or more of the exemplary apparatus described herein may be configured to deliver radiofrequency current (350-400 kHz) to modify multiple non-contiguous volumes of at least an acellular layer of a cornea or any other acellular or collagenous structure positioned anterior to a retina of an eye to reboot the visual system of an eye by redirecting light away from a PRL to a plurality of retinal locations that are not the PRL and/or by causing a defocusing of environmental light from within a field of view of the eye to the PRL and/or a focusing at a plurality of non-contiguous retinal locations that are not the PRL. Some of the exemplary apparatus described herein may be configured for conductive keratoplasty and additionally, or alternatively, to configured to deliver radiofrequency current (350-400 kHz) to modify multiple non-contiguous volumes of at least one of corneal stroma and corneal epithelium or any other acellular or collagenous structure positioned anterior to a retina of an eye to redirect light away from a PRL to a plurality of retinal locations that are not the PRL.

Some of the exemplary apparatus described herein, which improve vision in an eye with an impairment of central vision, may cause a defocusing of environmental light from within a field of view of the eye at a preferred retinal locus of fixation of the eye by modifying a mechanical property or behavior in a plurality of portions outside a central optical zone of a structure positioned anterior to a retina. Further, some of the exemplary apparatus described herein, which improve vision in an eye with an impairment of central vision, may cause a defocusing of environmental light from within a field of view of the eye at a PRL of the eye by modifying a mechanical property or behavior in a plurality of portions outside a central optical zone of a cornea. Some of the exemplary apparatus described herein may also modify a mechanical behavior or property in a plurality of portions of a cornea outside a central optical zone. The plurality of portions of the cornea may, for example, include mechanically active portions of the cornea, such as, but not limited to, an anterior acellular layer.

In some instances, one or more of the exemplary apparatus described herein may mechanically reinforce a plurality of portions of a cornea outside a central optical zone. For example, the central optical zone may be characterized by a diameter of at least 2 mm. Further, some of the exemplary apparatus described herein may cause a rebooting of a visual system of an eye by mechanical reinforcement and/or a modification of isotropy of at least an acellular layer or collagenous layer of a cornea or any other acellular or collagenous structure positioned anterior to a retina of an eye, and may include at least one component comprising at least one of a light directing component, an occluder, a programmable occlusion microarray, a light delivery element, a laser beam shaping element, a laser beam pulsing element, a laser beam aiming element, a chemical agent container, a chemical agent releasing component, or a chemical agent delivery element. Some of the exemplary methods and apparatus described herein may perform operations that mechanically reinforce corneal collagen, including but not limited to, increasing bonding within corneal collagen (e.g., using one or more components of the exemplary apparatus described herein).

Some of the exemplary apparatus described herein may include components including, but not limited to, a component for containing and/or releasing a chemical and/or a gas and/or a component for directing light from a light source for photochemical, photodynamic or photoionizing modification of corneal collagen. In some instances, one or more of the exemplary apparatus and methods described herein may mechanically reinforce multiple corneal microvolumes outside a central optical zone greater than 2 mm in diameter. Each microvolume may, for example, be of any determinable volumetric shape of corneal tissue. Further, the microvolumes may also be characterized by a depth of any determinable depth no deeper than 200 microns, and may be characterized by an area with a smallest diameter of no less than 0.05 mm and a largest diameter of no more than 5 mm. The surface area may be circular, hexagonal, elliptical, oval, square, rectangular, or of any determinable shape.

Further, in some instances, one or more of the exemplary methods described herein may utilize an apparatus that includes an ultraviolet light source, a controller coupled electrically to the ultraviolet light source, and a component or a separate apparatus disposed between the ultraviolet light source and a cornea to direct ultraviolet light to, or release a chemical agent onto, a plurality of non-contiguous portions of at least an anterior acellular layer of the cornea based on a determinable diameter of a central optical zone (OZ) and determinable location and volumes of non-contiguous corneal portions based on, among other criteria, isotropic behavior or properties of the portions. For instance, one or more of the exemplary apparatus described herein, which reboot a visual system of an eye, may be configured with occlusion components to direct, transepithelially outside of a central OZ to non-contiguous corneal portions of a determinable depth of at least an anterior acellular layer, one or more of: (i) a commercially available riboflavin formulation of determinable concentration for a determinable amount of time to photosensitize the portions for mechanically reinforcement, with minimal penetration to other portions of the cornea; and (ii) ultraviolet-A (UV-A) radiation for a determinable amount of time at a determinable irradiance for activation of the determinable depth of the anterior cornea.

In some instances, one or more of the exemplary apparatus described herein may include components that facilitate a manual control of one or more of the processes described herein. Further, some of the exemplary apparatus described herein may include a programmable microarray to direct activation light to the non-contiguous corneal portions of at least an anterior acellular layer and/or to contain and release a photosensitizer, such as riboflavin, and a controller programmed to cause controlled transepithelial mechanical reinforcement of, for example, four, 1 mm diameter-circular corneal portions that include at least an anterior acellular layer and having a depth of about 30 microns beneath the epithelium. For example, the four portions may be centered on a 6 mm OZ centered on a PRL (by patient fixation on a light) and overlie approximately isotropic corneal portions (as shown in FIG. 22) of the anterior-most cornea at the 12 o'clock, 3 o'clock, 6 o'clock and 9 o'clock positions.

Implementation examples are described in the following numbered clauses:

1. An apparatus for improving or restoring vision, the apparatus comprising:
    one or more clear components positioned anterior to a retina of an eye;
    one or more transformable components disposed on a surface of, or within, the one or more clear components; and
    a controller coupled to the one or more transformable components via a conductive component, the controller being configured to generate and route control signals to the one or more transformable components,
    wherein, upon receipt of the control signals, the one or more transformable components reorganize at least one pattern of a direction of environmental light from within a field of view of the eye to the retina at a determinable rate up to 50 kilohertz, and
    wherein the at least one pattern causes a defocusing at the preferred retinal locus of fixation of the eye and wherein the at least one pattern does not generate an aperture.
2. The apparatus of clause 1, wherein the at least one pattern of direction of environmental light to the retina causes a focusing at a plurality of non-contiguous retinal locations that are not the preferred retinal locus of fixation.
3. The apparatus of clause 1, further comprising at least one lens.
4. The apparatus of clause 1, wherein the one or more transformable components comprise at least one component with at least one of an isotropic property or an isotropic behavior.
5. The apparatus of clause 1, wherein the pattern of direction of environmental light to the retina is reorganized by at least a modification of isotropy.
6. The apparatus of clause 1, wherein the pattern of direction of environmental light to the retina is reorganized by at least a transformation of one or more optomechanical components.
7. An apparatus, comprising:
    at least one or more transformable components positioned anterior to a retina of an eye; and
    a controller coupled to the one or more transformable components via a conductive component, the controller being configured to generate and route control signals to the one or more transformable components,
    wherein, upon receipt of the control signals, the apparatus causes a weighting of exposure of environmental light from within a field of view of the eye to reduce exposure of environmental light from within the field of view of the eye to a preferred retinal locus of centration of the eye by at least 10% for a determinable interval, and
    wherein the environmental light within the field of view is exposed to the retina at a determinable rate up to 50 kilohertz.
8. An apparatus for improving or restoring vision, the apparatus comprising
    one or more components directing light from a light source to at least a plurality of non-contiguous corneal portions, the light source comprising at least one of a laser or a non-laser light source, wherein the non-contiguous corneal portions are located outside a central optical zone and include at least an acellular layer of a normal for age-cornea,
wherein the light source does not produce corneal vitrification, and
wherein the apparatus causes at least one modification of corneal isotropy outside the central optical zone.

9. The apparatus of clause 8, wherein the apparatus modifies in at least one direction at least one of a mechanical property and a mechanical behavior.

10. The apparatus of clause 8, wherein the apparatus modifies in at least one direction at least one of an optical property and an optical behavior.

11. The apparatus of clause 8, wherein the light source emits at least one of an ultraviolet radiation and an infrared radiation.

12. The apparatus of clause 8, further comprising one or more components configured to cause at least one of a defocusing of environmental light from within a field of view of an eye at a preferred retinal locus of fixation of the eye and a focusing at a plurality of non-contiguous retinal locations that are not the preferred retinal locus of fixation.

13. The apparatus of clause 12, wherein the defocusing of environmental light from within the field of view of an eye at the preferred retinal locus of fixation of the eye and a focusing at the plurality of non-contiguous retinal locations that are not the preferred retinal locus of fixation do not require measurement of optical errors at the non-contiguous retinal locations.

14. The apparatus of clause 8, further comprising one or more components configured to cause corneal surface patterning, and wherein the corneal surface patterning is at least one of phototunable and approximately reversible.

15. The apparatus of clause 8, further comprising one or more components configured to cause mechanical reinforcement of the plurality of non-contiguous portions to which light from the light source is directed.

16. The apparatus of clause 8, further comprising one or more components configured to release mechanical reinforcement agents.

17. A method, comprising weighting, using an apparatus positioned anterior to a retina of an eye, exposure of environmental light from within a field of view of the eye to reduce exposure to a preferred retinal locus of centration of the eye by at least 10% for a determinable interval, wherein the environmental light from within the field of view is exposed to the retina at a determinable rate up to 50 kilohertz.

18. A method for improving vision in an eye with an impairment of central vision, the method comprising causing, using an apparatus, a defocusing of environmental light from within a field of view of the eye at a preferred retinal locus of fixation of the eye.

19. The method of clause 18, further comprising causing, using the apparatus, a focusing of environmental light within at least one of a genetically altered portion of the retina, an epigenetically altered portion of the retina and a neuroregeneratively altered portion of the retina.

20. The method of clause 18, further comprising causing, using the apparatus, a focusing of environmental light within a plurality of portions of a retina that includes at least one of a retinal transplant, an implanted retinal cell, an implanted stem cell, or an implanted prosthesis.

21. The method of clause 18, further comprising modifying, using the apparatus, at least a plurality of corneal portions of a cornea outside a central optical zone, wherein the plurality of corneal portions of the cornea include mechanically active portions of the cornea.

22. The method of clause 18, further comprising modifying, using the apparatus, an optical property or behavior in a plurality of portions outside a central optical zone of a structure positioned anterior to a retina.

23. The method of clause 18, further comprising modifying, using the apparatus, a mechanical property or behavior in a plurality of portions outside a central optical zone of a structure positioned anterior to a retina.

What is claimed is:

1. An apparatus for improving or restoring vision, the apparatus comprising:
one or more clear components configured to be positioned anterior to a retina of an eye;
one or more transformable components disposed on a surface of, or within, the one or more clear components; and
a controller coupled to the one or more transformable components via a conductive component, the controller being configured to generate and route control signals to the one or more transformable components,
wherein, upon receipt of the control signals, the one or more transformable components are configured to reorganize at least one pattern of a direction of environmental light from within a field of view of the eye to the retina at a determinable rate up to 50 kilohertz, and
wherein the at least one pattern causes a defocusing at a preferred retinal locus of fixation of the eye and wherein the at least one pattern does not generate an aperture.

2. The apparatus of claim 1, wherein the at least one pattern of direction of environmental light to the retina causes a focusing at a plurality of non-contiguous retinal locations that are not the preferred retinal locus of fixation.

3. The apparatus of claim 1, further comprising at least one lens.

4. The apparatus of claim 1, wherein the one or more transformable components comprise at least one component with at least one of an isotropic property or an isotropic behavior.

5. The apparatus of claim 1, wherein the pattern of direction of environmental light to the retina is reorganized by at least a modification of isotropy.

6. The apparatus of claim 1, wherein the pattern of direction of environmental light to the retina is reorganized by at least a transformation of one or more optomechanical components.

7. An apparatus, comprising:
at least one or more transformable components configured to be positioned anterior to a retina of an eye; and
a controller coupled to the one or more transformable components via a conductive component, the controller being configured to generate and route control signals to the one or more transformable components,
wherein, upon receipt of the control signals, the apparatus causes a weighting of exposure of environmental light from within a field of view of the eye to reduce exposure of environmental light from within the field of view of the eye to a preferred retinal locus of fixation of the eye by at least 10% for a determinable interval, and wherein the environmental light within the field of view is exposed to the retina at a determinable rate up to 50 kilohertz.

\* \* \* \* \*